United States Patent [19]
Askew et al.

[11] Patent Number: 5,852,045
[45] Date of Patent: Dec. 22, 1998

[54] FIBRINOGEN RECEPTOR ANTAGONISTS

[75] Inventors: Ben C. Askew; George D. Hartman, both of Lansdale; Mark E. Duggan, Schwenksville; Steven D. Young, Lansdale; John H. Hutchinson, Philadelphia; John S. Wai, Harleysville; Melissa S. Egbertson, Ambler; Laura M. Vassallo, Haverton; Laura A. Libby, North Wales; Amy E. Krause, Blue Bell; Wasyl Halczenko, Lansdale, all of Pa.; Nathan C. Ihle, Seattle, Wash.

[73] Assignee: Merck & Co., Inc., Rahway, N.J.

[21] Appl. No.: 729,968

[22] Filed: Oct. 15, 1996

Related U.S. Application Data

[60] Provisional application No. 60/005,602 Oct. 19, 1995.

[51] Int. Cl.$^6$ ............... A61K 31/445; A61K 31/495; C07D 401/06; C07D 401/14
[52] U.S. Cl. ............... 514/318; 514/212; 514/218; 514/256; 514/299; 514/318; 514/341; 514/351; 514/396; 514/397; 514/326; 544/316; 546/112; 546/193; 546/194; 546/210; 546/278.4; 548/314.7
[58] Field of Search ............... 546/112, 193, 546/194, 210, 278.4; 548/314.7; 540/492, 531; 544/316; 514/318, 341, 351, 396, 397, 212, 218, 256, 299, 326

[56] References Cited

U.S. PATENT DOCUMENTS

| | | | |
|---|---|---|---|
| 3,322,631 | 5/1967 | Sprague et al. | 167/65 |
| 4,010,274 | 3/1977 | Giraldi et al. | 514/416 |
| 4,313,947 | 2/1982 | Nakagawa et al. | 424/248.54 |
| 5,030,654 | 7/1991 | Barnish et al. | 514/510 |
| 5,037,808 | 8/1991 | Tjoeng et al. | 514/20 |
| 5,051,405 | 9/1991 | Klein et al. | 514/18 |
| 5,264,420 | 11/1993 | Duggan et al. | 514/19 |
| 5,272,158 | 12/1993 | Hartman et al. | 514/323 |
| 5,281,585 | 1/1994 | Duggan et al. | 514/79 |
| 5,321,034 | 6/1994 | Duggan et al. | 514/323 |
| 5,334,596 | 8/1994 | Hartman et al. | 514/301 |

FOREIGN PATENT DOCUMENTS

| | | |
|---|---|---|
| 0 229 391 | 7/1987 | European Pat. Off. . |
| 0 332 528 | 9/1989 | European Pat. Off. . |
| 0 352 249 | 1/1990 | European Pat. Off. . |
| 0 405 537 | 1/1991 | European Pat. Off. . |
| 0 540 334 | 5/1993 | European Pat. Off. . |
| 94/14776 | 7/1994 | WIPO . |
| 95/25101 | 9/1995 | WIPO . |

OTHER PUBLICATIONS

Sugimoto et al., Journal of Medicinal Chemistry, "7-(Ethoxycarbonyl)-6,8-dimethyl-2-phenyl-" etc., 27, 1300–1305 (1984).

*Primary Examiner*—Evelyn Huang
*Attorney, Agent, or Firm*—Melvin Winokur; Richard S. Parr

[57] ABSTRACT

Fibrinogen receptor antagonists having the structure, for example, of $$X-Y-E \underset{O}{\overset{(\ )_{n'}}{\diagup}} G \underset{O}{\overset{}{\diagdown}} (CH_2)_m CNH(CH_2)_n \underset{R^{10}}{\overset{R^8}{\diagup}} \underset{O}{\overset{O}{\diagdown}} C-R^{12}$$

for example

[chemical structure]

13 Claims, No Drawings

FIBRINOGEN RECEPTOR ANTAGONISTS

This application claims the benefit of U.S. Provisional application No. 60/005,602, filed Oct. 19, 1995.

BACKGROUND OF THE INVENTION

The invention relates generally to modulating cell adhesion and to inhibiting the binding of fibrinogen and other proteins to blood platelets, and inhibiting the aggregation of blood platelets specifically to the gp IIb/IIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothethial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in *Science*, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in *Proc. Nat'l Acad. Sci. U.S.A.*, 84, 6471–6475, (1987), describes an Arg-Gly-Asp directed adhesion receptor expressed by human endothethial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in *J. of Biol. Chem.*, 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the sterochemical conformation of Arg-Gly-Asp as influenced by enantiomeric substitutions or additions to this sequence significantly influenced receptor-ligand interaction. The authors further showed that cyclization of a decapeptide by forming a disulfide bridge between non-terminal residues Pen and Cys, rendered the peptide much less effective at inhibiting attachment to fibronectin.

In *Proc. Nat'l Acad. Sci. U.S.A.*, 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and U.S. Pat. No. 4,578,079.

Ruggeri et al., *Proc. Nat'l Acad. Sci. U.S.A.*, 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., *Biochem.* 23, 1767–1774 (1984); Ginsberg et al., *J. Biol. Chem.* 260(7), 3931–3936 (1985); and Haverstick et al., *Blood* 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gp IIb/IIIa complex. For example, Huang et al., *J. Biol Chem.*, 262, 16157–16163 (1987); Huang et al., *Biochemistry*, 28, 661–666 (1989) describe the primary structure of the venom trigramin which is a 72 amino acid polypeptide that contains the RGD subunit. Echistatin is another compound which has high affinity for the gp IIb/IIIa complex. This polypeptide contains 49 amino acids and has the RGD subunit and various disulfide bridges. Gan et al., *J. Biol. Chem.*, 263, 19827–19832 (1988). See also, Dennis et al., *Proc. Nat'l Acad. Sci. USA*, 87, 2471–2475 (1989). However, these snake venom factors also have high affinity for other members of the adhesive protein receptor family including the vitronectin and fibronectin receptors so are not selective for the gp IIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No. 5,023,233 discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gp IIb/IIIa receptor. U.S. Pat. No. 5,037,808 discloses guanidino peptide mimetic compounds that retain an Asp residue which inhibit platelet aggregation. WO9014103 describes the use of antibody-poly-peptide conjugates wherein said polypeptides contain the Arg-Gly-Asp (RGD) sequence.

WO9111458 discloses the use of large cyclic peptides containing RGD flanked by proline residues which are platelet aggregation inhibitors. WO9101331 discloses small cyclic platelet aggregation inhibitors which are synthetic cyclic pentapeptides containing the tripeptide sequence Arg-Gly-Asp and a thioether linkage in the cycle. U.S. Pat. No. 5,051,405 also discloses the use of peptides and pseudopeptides such as N-amidino-piperidine-3-carboxylglycyl-L-aspartyl-L-valine that inhibit platelet aggregation and thrombus formation in mammalian blood. EP 445 796 discloses linear compounds which can include internal piperazinyl or piperidinyl derivatives. EP437 367 discloses linear polypeptide fibrinogen receptor antagonists. U.S. Pat. No. 5,256,812 discloses compounds of the $R^1$—A—$(W)_a$—X—$(CH_2)_b$—$(Y)_c$—B—Z—COOR wherein $R^1$ is a guandidino or amidino moiety and A and B are chosen from specific monosubstituted aryl or heterocyclic moieties.

While a multitude of compounds or peptide analogs believed to inhibit platelet aggregation by inhibiting binding to a blood platelet by fibrinogen are known, the present invention provides novel fibrinogen receptor antagonists that have significant binding activity and are, therefore, useful for the reasons stated herein. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

Fibrinogen receptor antagonists of this invention have the formula:

and pharmaceutically acceptable salts, e.g.

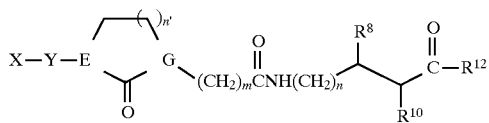

Compounds of the invention are useful for inhibiting the binding of fibrinogen to blood platelets and for inhibiting the aggregation of blood platelets. The above-mentioned compounds can be used in a method of acting upon a fibrinogen receptor which comprises administering a therapeutically effective but non-toxic amount of such compound to a mammal, preferably a human. A pharmaceutical composition comprising a pharmaceutically acceptable carrier and, dispersed therein, an effective but non-toxic amount of such compound is another feature of this invention. The invention also includes the use of a compound of claim 1, or a pharmaceutically acceptable salt thereof, in the manufacture of a medicament for inhibiting the aggregation of blood platelets, preventing platelet thrombosis, preventing thromboembolism or preventing reocclusion, in a mammal.

DETAILED DESCRIPTION OF THE INVENTION

Fibrinogen receptor antagonist compounds of Formula I are useful in a method of inhibiting the binding of fibrinogen to blood platelets and for inhibiting the aggregation of blood platelets.

Fibrinogen receptor antagonists of this invention have the formula:

and pharmaceutically acceptable salts, wherein

X is
  a 5 or 6-membered monocyclic aromatic ring system containing 0, 1, 2, 3 or 4 heteroatoms selected from N, O and S and either unsubstituted or substituted with $R^1$, $R^2$, $R^3$, or $R^4$, or
  a 9 or 10-membered bicyclic aromatic ring system containing 0, 1, 2, 3 or 4 heteroatoms selected from N, O and S and either unsubstituted or substituted with $R^1$, $R^2$, $R^3$, or $R^4$, wherein $R^1$, $R^2$, $R^3$ and $R^4$ are independently selected from the group consisting of hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino $C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, carboxy, carboxy $_{1-6}$ alkyl, $C_{1-3}$ alkoxycarbonyl, $C_{1-3}$ alkoxycarbonyl $C_{1-6}$ alkyl, carboxy $C_{1-6}$ alkyloxy, hydroxy, and hydroxy $C_{1-6}$ alkyl;

Y, optionally present, is
$C_{1-8}$ alkyl,
$C_{4-10}$ cycloalkyl,
$NR^3$—CO—$C_{1-8}$ alkyl,
$NR^3$—CO,
$C_{1-8}$ alkyl-$NR^3$—CO,
$C_{1-8}$ alkyl-$NR^3$—CO—$C_{1-8}$ alkyl,
$CONR^3$—$C_{1-8}$ alkyl,
$CONR^3$,
$C_{1-8}$ alkyl-$CONR^3$,
$C_{1-8}$ alkyl-$CONR^3$—$C_{1-8}$ alkyl,
O—$C_{1-8}$ alkyl,
O,
$C_{1-8}$ alkyl-O,
$C_{1-8}$ alkyl-O—$C_{1-8}$ alkyl,
$S(O)_n$—$C_{1-8}$ alkyl,
$S(O)_n$,
$C_{1-8}$ alkyl-$S(O)_n$,
$C_{1-8}$ alkyl-$S(O)_n$—$C_{1-8}$ alkyl,
aryl$(CH_2)_{1-8}$,
aryl,
$(CH_2)_{1-8}$ aryl,
$(CH_2)_{1-8}$ aryl$(CH_2)_{1-8}$,
aryl-$S(O)_n$,
$(CH_2)_{1-6}$aryl-$S(O)_n$,
aryl-CO—$(CH_2)_{1-8}$,
aryl-CO,
$(CH_2)_{1-8}$aryl-CO,
$(CH_2)_{1-8}$aryl-CO—$(CH_2)_{1-8}$,
aryl-$SO_2$—$(CH_2)_{1-6}$,
aryl-$SO_2$,
$(CH_2)_{1-6}$aryl-$SO_2$,
$(CH_2)_{1-6}$aryl-$SO_2$—$(CH_2)_{1-6}$,
$NR^3$—$(CH_2)_{1-6}$,
$NR_3$,
$(CH_2)_{1-6}$—$NR_3$,
$(CH_2)_{1-6}$—$NR^3$—$(CH_2)_{1-6}$,
aryl-CH(OH)—$(CH_2)_{1-6}$,
aryl-CH(OH),
$(CH_2)_{1-6}$-aryl-CH(OH),
$(CH_2)_{1-6}$-aryl-CH(OH)—$(CH_2)_{1-6}$,
aryl-CONH—$(CH_2)_{1-8}$,
aryl-CONH,
$(CH_2)_{1-8}$aryl-CONH,
$(CH_2)_{1-8}$aryl-CONH—$(CH_2)_{1-8}$,
$SO_2$—$NR^3$—$C_{1-8}$ alkyl-,
$SO_2$—$NR^3$,
$C_{1-8}$ alkyl-$SO_2$—$NR^3$,
$C_{1-8}$ alkyl-$SO_2$—$NR^3$—$C_{1-8}$ alkyl-,
CO—$C_{1-8}$ alkyl,
CO,
$C_{1-8}$ alkyl-CO,
$C_{1-8}$ alkyl-CO—$C_{1-8}$ alkyl,
CH(OH)—$C_{1-8}$-alkyl,
CH(OH),
$C_{1-8}$ alkyl-CH(OH),
$C_{1-8}$ alkyl-CH(OH)—$C_{1-8}$-alkyl,
$CR^1$=$CR^2(CH_2)_{1-6}$,
$CR^1$=$CR^2$,
$(CH_2)_{1-6}$ $CR^1$=$CR^2$,
$(CH_2)_{1-6}$ $CR^1$=$CR^2(CH_2)_{1-6}$,
C≡C$(CH_2)_{1-6}$,
C≡C, $(CH_2)_{1-6} C{\equiv}C$,
$(CH_2)_{1-6} C{\equiv}C(CH_2)_{1-6}$,
$CH(OH)-(CH_2)_{1-6}$,
$CH(OH)$,
$(CH_2)_{1-6}-CH(OH)$, or
$(CH_2)_{1-6}-CH(OH)-(CH_2)_{1-6}$,
where n is an integer from 0–2;
A is

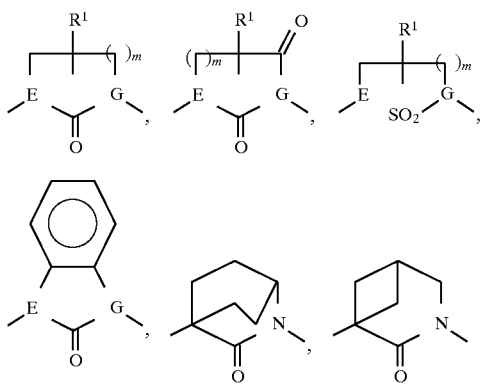

wherein m=0–3, E is —CH— or —N—
G is —CR— or —N—;
B is
$-(CH_2)_p-$, $-(CH_2)_pO(CH_2)_q-$, $-(CH_2)_pNR^3(CH_2)_q-$

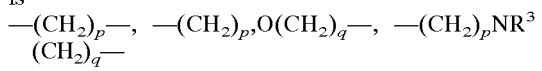

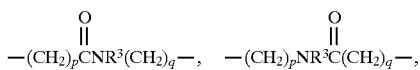

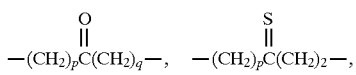

$-(CH_2)_pSO_2(CH_2)_q-$, $-(CH_2)_pS(CH_2)_q-$,
$-(CH_2)_pSO(CH_2)_q-$, $-(CH_2)_pSO_2NR^3(CH_2)_q-$,
$-(CH_2)_pCR^1{=}CR^2(CH_2)_q-$, $-(CH_2)_pC{\equiv}C(CH_2)_q-$,
$-(CH_2)_pC{=}C(CH_2)_q-$, or $-(CH_2)_pCH(OH)(CH_2)_q-$ where p and q are integers independently chosen from 0–6, and wherein methylene units are unsubstituted or substituted with one or more groups chosen from $R^1$ and $R^2$; provided that when B is $(CH_2)_p$, A must contain at least one heteroatom;
J is

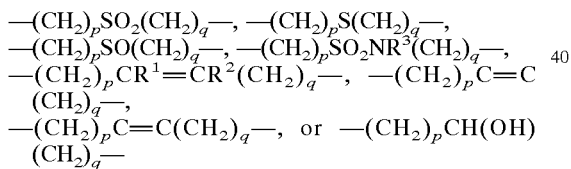

wherein $R^6$, $R^7$, $R^8$, $R^9$, $R^{10}$, and $R^{11}$ are independently chosen from:
hydrogen,
fluorine,
hydroxy $C_{1-6}$ alkyl,
carboxy,
carboxy $C_{1-6}$ alkyl,
$C_{1-8}$ alkyl,
hydroxyl, $C_{1-6}$ alkyloxy,
aryloxy,
aryl-$C_{1-6}$alkyloxy,
$C_{3-8}$ cycloalkyl,
aryl,
aryl $C_{1-6}$ alkyl,
$C_{1-6}$ alkylcarbonyloxy,
amino $C_{1-6}$ alkyl,
amino,
$C_{1-6}$ alkylamino,
$C_{1-6}$ alkylamino $C_{1-6}$ alkyl,
aryl amino $C_{1-6}$alkyl,
aryl $C_{1-6}$ alkylamino,
aryl amino,
aryl $C_{1-6}$ alkylamino $C_{1-6}$alkyl,
amino,
$C_{1-6}$ dialkylamino,
$C_{1-6}$ dialkylamino $C_{1-6}$ alkyl,
aminocarbonyloxy,
$C_{1-6}$ alkylaminocarbonyloxy,
aryl aminocarbonyloxy,
aryl $C_{1-6}$ alkylaminocarbonyloxy,
$C_{1-8}$ alkylsulfonylamino,
$C_{1-8}$ alkylsulfonylamino $C_{1-6}$ alkyl,
aryl sulfonylamino $C_{1-6}$ alkyl,
aryl sulfonylamino,
aryl $C_{1-6}$ alkylsulfonylamino,
aryl $C_{1-6}$ alkylsulfonylamino $C_{1-6}$ alkyl,
$C_{1-8}$ alkloxycarbonylamino,
$C_{1-8}$ alkloxycarbonylamino $C_{1-8}$ alkyl,
aryl oxycarbonylamino $C_{1-8}$ alkyl,
aryl oxycarbonylamino,
aryl $C_{1-8}$ alkyloxycarbonylamino,
aryl $C_{1-8}$ alkyloxycarbonylamino $C_{1-8}$ alkyl,
$C_{1-8}$ alkylcarbonylamino,
$C_{1-8}$ alkylcarbonylamino $C_{1-6}$ alkyl,
aryl carbonylamino $C_{1-6}$ alkyl,
aryl carbonylamino,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
aminocarbonylamino,
$C_{1-8}$ alkylaminocarbonylamino,
$C_{1-8}$ alkylaminocarbonylamino $C_{1-6}$ alkyl,
aryl aminocarbonylamino $C_{1-6}$ alkyl,
aryl aminocarbonylamino,
aryl $C_{1-8}$ alkylaminocarbonylamino,
aryl $C_{1-8}$ alkylaminocarbonylamino $C_{1-6}$ alkyl,
aminosulfonylamino $C_{1-6}$ alkyl,
aminosulfonylamino,
$C_{1-8}$ alkylaminosulfonylamino,
$C_{1-8}$ alkylaminosulfonylamino $C_{1-6}$ alkyl,
aryl aminosulfonylamino $C_{1-6}$ alkyl,
aryl aminosulfonylamino,
aryl $C_{1-8}$ alkylaminosulfonylamino,
aryl $C_{1-8}$ alkylaminosulfonylamino $C_{1-6}$ alkyl,
$C_{1-6}$ alkylsulfonyl,
$C_{1-6}$ alkylsulfonyl $C_{1-6}$ alkyl,
aryl sulfonyl $C_{1-6}$ alkyl,
aryl sulfonyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
aryl carbonyl $C_{1-6}$ alkyl,
aryl carbonyl,
aryl $C_{1-6}$ alkylcarbonyl,
aryl $C_{1-6}$ alkylcarbonyl $C_{1-6}$ alkyl, aminocarbonyl $C_{1-8}$ alkyl,
aminocarbonyl,
$C_{1-8}$alkylaminocarbonyl,
$C_{1-8}$alkylaminocarbonyl $C_{1-8}$ alkyl,
aryl aminocarbonyl $C_{1-8}$ alkyl,
aryl aminocarbonyl,
aryl $C_{1-8}$ alkylaminocarbonyl,
aryl $C_{1-8}$ alkylaminocarbonyl $C_{1-8}$ alkyl,
aminosulfonyl $C_{1-8}$ alkyl,
aminosulfonyl,
$C_{1-8}$ alkylaminosulfonyl,
$C_{1-8}$ alkylaminosulfonyl $C_{1-8}$ alkyl,
aryl aminosulfonyl $C_{1-8}$ alkyl,
aryl aminosulfonyl,
aryl $C_{1-8}$ alkylaminosulfonyl,
aryl $C_{1-8}$ alkylaminosulfonyl $C_{1-8}$ alkyl,
wherein alkyl groups and aryl groups may be unsubstituted or
substituted with one or more substituents selected from $R^1$ and $R^2$; and
$R^{12}$ is
hydroxy,
$C_{1-8}$ alkyloxy,
aryloxy,
aryl $C_{1-6}$ alkyloxy,
$C_{1-8}$ alkylcarbonyloxy $C_{1-4}$ alkyloxy,
aryl $C_{1-8}$ alkylcarbonyloxy $C_{1-4}$ alkyloxy, and
an L- or D-amino acid joined by an amide linkage and wherein the carboxylic acid moiety of said amino acid is as the free acid or is esterified by $C_{1-6}$ alkyl.

A class of these compounds of the invention are those having the following structure

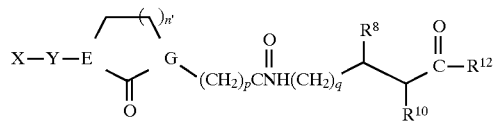

and pharmaceutically acceptable salts thereof, wherein
X is
a 5- to 6- membered monocyclic aromatic ring system containing 1 or 2 nitrogen atoms and either unsubstituted or substituted with —$NH_2$;
Y, optionally present, is
$C_{1-8}$ alkyl;
n' is 1, 2, or 3;
E is —CH— or —N—;
G is —CH— or —N—;
p and q are integers independently chosen from 0–6; and
$R^8$, $R^{10}$, $R^{12}$ and $R^2$ are as previously defined.

In a subclass of this class of compounds of the invention are those having the following structure

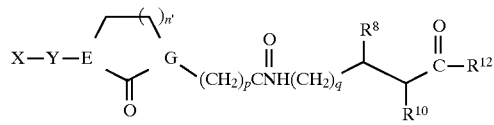

and pharmaceutically acceptable salts thereof, wherein
$R^8$ is
hydrogen,
$C_{1-8}$ alkyl,
aryl,
aryl $C_{1-6}$ alkyl,
hydroxy $C_{1-6}$ alkyl,
$C_{1-6}$ alkylsulfonyl,
$C_{1-6}$ alkylsulfonyl $C_{1-6}$ alkyl,
aryl sulfonyl $C_{1-6}$ alkyl,
aryl sulfonyl,
aryl $C_{1-6}$ alkylsulfonyl, or
aryl $C_{1-6}$ alkylsulfonyl $C_{1-6}$ alkyl;
$R^{10}$ is
hydrogen,
—$NHCOR^2$,
—$NH_2$,
—$NH_2SO_2R^2$, or
—OH;
$R^{12}$ is
hydrogen,
—$OR^2$,
—$OCH_2OCOR^2$, or
—$OCH_2OCON(R^2)_2$; and
$R^2$ is as previously defined.

In a group of this subclass of compounds are those having the following structure

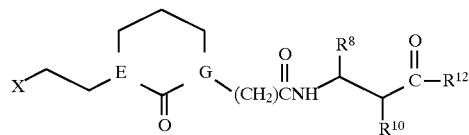

and pharmaceutically acceptable salts thereof, wherein
X is
an aromatic heterocyclic ring selected from the group consisting of:

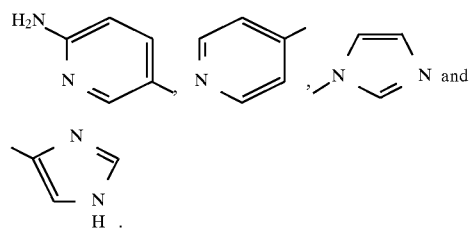

In a subgroup of this group are compounds having the following structure

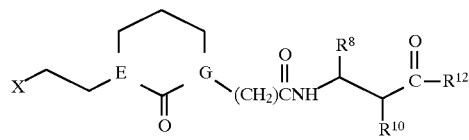

and pharmaceutically acceptable salts thereof, wherein
$R^8$ is

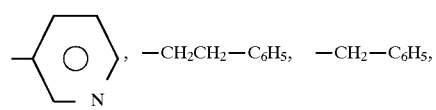

-continued

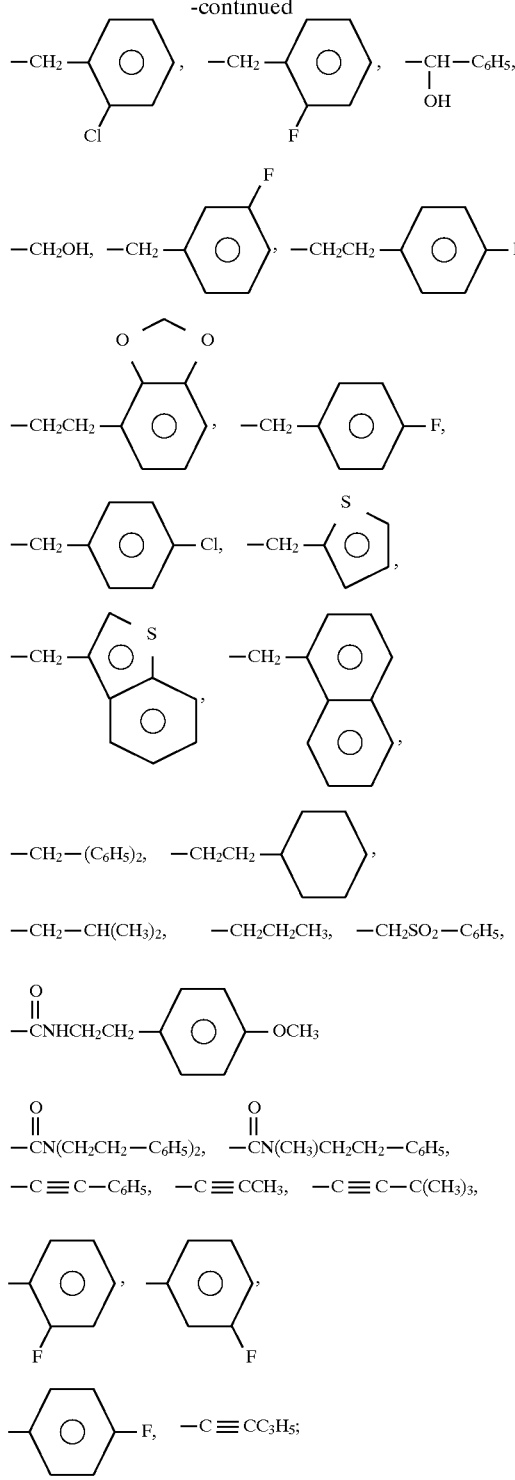

and

R² is
-hydrogen
—CH₂C₆H₅,
—CH₂C(O)N(CH₂CH₃)₂,
—CH₂C(O)N(CH₃)C₆H₁₃,
—CH₂CH₃,
—C(CH₃)₃,
—CH(CH₃)₂OC(O)CH₂CH₃,

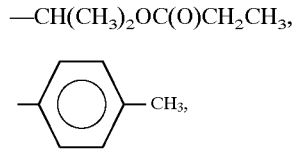

Specific exemplifications of the subclass include:
[3(R)-[1-(2-(Pyridin-4-yl)ethyl)-2-piperidon-3-yl] acetamnido]-3-(3(R)-methyl)propanoic acid benzyl ester (1-9)
[3(R)-[1-(2-(Pyridin-4-yl)ethyl)-2-piperidon-3-yl] acetamido]-3-(3(R)-methyl)propanoic acid (1-10)
[3(R)-[1-(2-(Pyridin-4-yl)ethyl)-2-piperidon-3-yl] acetamido]-3-(3(R)-methyl)propanoic acid dimethylaminoglycolamide ester (1-11)
[3(R)-[1-(2-(Pyridin-4-yl)ethyl)-2-piperidon-3-yl] acetamido]-3-(3(R)-methyl)propanoic acid methylhexylaminoglycolamide ester (1-12)
[3(R)-[1-(3-(Pyridin-4-yl)propyl)-2-piperidon-3-yl] acetamido]-3-(3(R)-methyl)propanoic acid benzyl ester (1-15)
[3(R)-[1-(3-(Pyridin-4-yl)propyl)-2-piperidon-3-yl] acetamido]-3-(3(R)-methyl)propanoic acid (1-16)
[3(R)-[1-(2-(2-Aminopyridin-4-yl)ethyl)-2-piperidon-3-yl] acetamido]-3-(3(S)-(pyridin-3-yl))propanoic acid ethyl ester (1-19)
[3(R)-[1-(2-(2-Aminopyridin-4-yl)ethyl)-2-piperidon-3-yl] acetamido]-3-(3(S)-(pyridin-3-yl))propanoic acid (1-20)
[3(R,S)-[1-(2-(Pyridin-4-yl)ethyl)-2-piperidon-3-yl] acetamido]-3-(3(S)-phenyl)propanoic acid methyl ester (3-9)
[3(R,S)-[1-(2-(Pyridin-4-yl)ethyl)-2-piperidon-3-yl] acetamido]-3-(3(S)-phenyl)propanoic acid (3-10)
[3(R,S)-[1-(2-(Pyridin-4-yl)ethyl)-2-piperidon-3-yl] acetamido]-3-(3(S)- phenyl)propanoic acid pivaloyloxymethyl ester (3-11)
N-[1-[2-(4-Pyridyl)ethyl]-2-piperidone-3-yl]acetyl-3(S)-(3-pyridyl)-β-alanine ethyl ester (3-12)
N-[1-[2-(4-Pyridyl)ethyl]-2-piperidone-3-yl]acetyl-3(S)-3-pyridyl)-β-alanine (3-13)
N-[1-2-(4-Pyridyl)ethyl]-2-piperidone-3-yl]acetyl-3(R)-(2-phenethyl)-β-alanine (3-15),
N-[1-[2-(4-Pyridyl)ethyl]-2-piperidone-3-yl]acetyl-3-ethynyl-β-alanine (3-17)
[[3(R)-(2-(Pyridin-4-yl)ethyl)-2-piperidon-1-yl]acetamido]-3(S)-butyrolactone (6-3)
[[3(R)-(2-(Pyridin-4-yl)ethyl)-2-piperidon-1-yl]acetamido]-3(S)-(4-hydroxy)butanoic acid (6-4)
[[3(R)-(2-(Pyridin-4-yl)ethyl)-2-piperidon-1-yl]acetamido]-3(S)-(4(R,S)-phenyl)butyrolactone (7-5)
[[3(R)-(2-(Pyridin-4-yl)ethyl)-2-piperidon-1-yl]acetamido]-3(S)-(4(R,S)-phenyl4-hydroxy)butanoic acid (7-6)
[3(R)-[2-(4-Pyridyl)ethyl]-2-piperidon-1-yl]acetyl-3(R)-methyl-β-alanine pivyloxymethyl ester
[3(R)-[2-(4-Pyridyl)ethyl]-2-piperidon-1-yl]acetyl-3(R)-methyl-β-alanine diethylaminoglycolamide ester
[3(R)-[2(Pyridin-4-yl)ethyl]-2-piperidone-1]-acetyl-3(R)-methyl-β-alanine isobutyryl propiolate
3(R)-[2-(4-Pyridyl)ethyl]-2-piperidon-1-yl]acetyl-3(R)-methyl-β-alanine (8-2)
[3(R)-[2-(Pyridin-4-yl)ethyl]-2-piperidon-1-yl]acetyl-2(S)-benzyloxycarbonylamino-β-alanine ethyl ester (9-3)
[3(R)-[2-Pyridin-4-yl)ethyl]-2-piperidon-1-yl]acetyl-2(S)-benzyloxy-carbonylamino-β-alanine (9-4)
[3(R)-[2-(Pyridin-4-yl)ethyl]-2-piperidon-1-yl]acetyl-2(S)-amino-β-alanine ethyl ester (9-5)
[3(R)-[2-(Pyridin-4-yl)ethyl]-2-piperidon-1-yl]acetyl-2(S)-amino-β-alanine (9-6)

[3(R)-[2-(Pyridin-4-yl)ethyl]-2-piperidone-1]-acetyl-2(S)-ethylsulfonylamino-β-alanine ethyl ester (9-7)

[3(R)-[2-(Pyridin-4-yl)ethyl]-2-piperidone-1]-acetyl-2(S)-ethylsulfonylamino-β-alanine (9-8)

(3(R)-[(2-Amino-4-pyridyl)ethyl]-2-piperidon-1-yl)acetyl-β-alanine-tert-butyl ester (10-7)

(3(R)-[(2-Amino-4-pyridyl)ethyl]-2-piperidon-1-yl)acetic-β-alanine (10-8)

(3(R)-[(2-Amino-4-pyridyl)ethyl]-2-piperidon-1-yl)acetyl-3(R)-methyl-β-alanine benzyl ester (10-9)

(3(R)-[(2-Amino-4-pyridyl)ethyl]-2-piperidon-1-yl)acetyl-3(R)-methyl-β-alanine (10-10)

(3(R)-[2-(Pyridin-4-yl)ethyl]-2-piperidon-1-yl)acetyl-3(R)-benzyl-β-alanine ethyl ester (11-3)

(3(R)-[2-(Pyridin-4-yl)ethyl]-2-piperidon-1-yl)acetyl-3(R)-benzyl-β-alanine (11-4)

(3(R)-[2-(Pyridin-4-yl)ethyl]-2-piperidon-1-yl)acetyl-3(R)-2-chlorobenzyl-β-alanine (11-5)

(3(R)-[2-(Pyridin-4-yl)ethyl]-2-piperidon-1-yl)acetyl-3(R)-2-fluoro-benzyl-β-alanine (11-6)

[3(R)-[2-(Pyridin-4-yl)ethyl]-2-piperidon-1-yl)acetyl-3(R)-3-fluoro-benzyl-βalanine (11-7)

[3(R)-[2-(Pyridin-4-yl)ethyl]-2-piperidon-1-yl)]acetyl-3(R)-4-fluoro-phenylethyl-β-alanine (11-12)

[3(R)-[2-(Pyridin-4-yl)ethyl]-2-piperidon-1-yl)acetyl-3(R)-3,4-methyl-enedioxyphenylethyl-β-alanine (11-13)

[3(R)-2-(Pyridin-4-yl)ethyl]-2-piperidon-1-yl)acetyl-4-fluorobenzyl-β-alanine (11-14)

[3(R)-2-(Pyridin-4-yl)ethyl]-2-piperidon-1-yl)acetyl-4-chlorobenzyl-β-alanine (11-15)

[3(R)-[2-(Pyridin-4-yl)ethyl]-2-piperidon-1-yl)acetyl-3(R)-3-(2-thienylmethyl)-β-alanine (11-16)

[3(R)-[2-(Pyridin-4-yl)ethyl]-2-piperidon-1-yl)acetyl-3(R)-3-benzylthienyl)-β-alanine (11-17)

[3(R)-[2-(Pyridin-4-yl)ethyl]-2-piperidon-1-yl]acetyl-3(R)-(1-naphthyl)-β-alanine (11-18)

[3(R)-[2-(Pyridin-4-yl)ethyl]-2-piperidon-1-yl)acetyl-3(R)-(1,1-diphenylmethyl)-β-alanine (11-19)

[3(R-(–)-[2-(Pyridin-4-yl)ethyl]-2-piperidon-1-yl)acetyl-3(R)-[2-(phenyl)ethyl]-β-alanine ethyl ester (12-4)

[3(R-(–)-[2-(Pyridin-4-yl)ethyl]-2-piperidon-1-yl)acetyl-3(R)-[2-(phenyl)ethyl]-β-alanine 3(R)-[2-(Pyridin-4-yl)ethyl]-2-piperidon-1-yl)]acetyl-3(R)-[2-(cyclohexyl)ethyl]-β-alanine (12-6)

3(R)-[2-(Pyridin-4-yl)ethyl]-2-piperidon-1-yl)acetyl-3(R)-[2-(methylpropyl]-β-alanine (12-7)

3(R)-[2-(Pyridin-4-yl)ethyl]-2-piperidon-1-yl)acetyl-3(R)-propyl]-β-alanine (12-8)

3-[2-(Pyridin-4-yl)ethyl]-2-piperidon-1-yl)acetyl-3(R)-phenylsulfonyl-methyl)-β-alanine (12-9)

3-(R)-(–)-[2-(Pyridin-4-yl)ethyl]-2-piperidon-1-yl]acetyl-(S)-aspartyl α-[2-(4)-methoxyphenyl)ethyl]amide benzyl ester (13-4)

3-(R)-[2-(Pyridin-4-yl)ethyl]-2-piperidon-1-yl]acetyl-aspartyl α-[2-(4)methoxyphenyl)ethyl]amide (13-5)

3-(R)-[2-(Pyridin-4-yl)ethyl]-2-piperidon-1-yl]acetyl-aspartyl-α-[2-phenyl)ethyl]amide (13-6)

3-(R)-[2-(Pyridin-4-yl)ethyl]-2-piperdinon-1-yl]acetyl-aspartyl-α-[bis-2-phenyl)ethyl]amide (13-7)

3-(R)-[2-(Pyridin-4-yl)ethyl]-2-piperidon-1-yl]acetyl-aspartyl β-[N-methyl-N-2(phenyl)ethyl]amide (13-8)

3-(R-(–)-[2-(Pyridin-4-yl)ethyl]-2-piperdinon-1-yl]acetyl-2(S)-(p-toluenesulfonylamino)-3-amino propionic acid (14-7)

Ethyl-3-(R)-(–)-[2-(Pyridin-4-yl)ethyl]-2-piperdinon-1-yl] acetyl-2(S)-(p-toluene sulfonylamino)-3-amino propionic acid (14-8)

3-(R)-(–)-[2-(Pyridin-4-yl)ethyl]-2-Piperon-1-yl]acetate-2(S)-(p-toluenesulfonylamino)-3-amino Propionic acid benzyl ester (14-9)

Ethyl 3(R,S)-[3(R)-[2-(pyridin-4-yl)ethyl]-2-piperidone-1-yl]acetamido-3-phenylethynylpropanoate (15-4)

3(R,S)-[3(R)-[2-(Pyridin-4-yl)ethyl]-2-piperidone-1-yl]acetamido-3-phenylethynylpropanoic acid (15-5)

3(R,S)-[3(R)-[2-(Pyridin-4-yl)ethyl]-2-piperidone-1-yl]acetamido-3-cyclopropylethynylpropanoic acid (15-6)

3(R,S)-[3(R)-[2-(Pyridin-4-yl)ethyl]-2-piperidone-1-yl]acetamido-3-(1-propynyl)propanoic acid (15-7)

3(R,S)-[3(R)-[2-(Pyridin-4-yl)ethyl]-2-piperidone-1-yl]acetamido-3-(3,3,-dimethyl-1-butynyl)propanoic acid (15-8)

N-[3(R)-[2-(4-Pyridyl)ethyl]-2-piperidone-1-yl]acetyl-3(R,S)-(2-fluorophenyl)-β-alanine ethyl ester (16-2a)

N-[3(R)-[2-(4-Pyridyl)ethyl]-2-piperidone-1-yl]acetyl-3-(2-fluoro-phenyl)-β-alanine: Diasteriomer A (16-4a)

N-[3(R)-[2-(1-Pyridyl)ethyl-2-piperidone-1-yl]acetyl-3-(2-fluoro-phenyl)-β-alanine: Diasteromer B (16-5a)

N-[3(R)-[2-(4-Pyridyl)ethyl]-2-piperidone-1-yl]acetyl-3-(2-fluoro-phenyl-β-alanine ethyl ester: Diasteromer A (16-6a)

N-[3(R)-[2-(4-Pyridyl)ethyl)-2-piperidone-1-yl]acetyl-3-(3-fluoro-phenyl-β-alanine: Diastereomer A (16-4b)

N-[3(R)-[2-(4-Pyridyl)ethyl]-2-piperidone-1-yl]acetyl-3-(3-fluoro-phenyl)-β-alanine: Diastereomer B (16-5b)

N-[3(R)-[2-(4-Pyridyl)ethyl)-2-piperidone-1-yl]acetyl-3-(4-fluoro-phenyl)-β-alanine: Diasteriomer A (16-4c)

N-[3(R)-[2-(4-Pyridyl)ethyl)-2-piperidone-1-yl]acetyl-3-(4-fluoro-phenyl)-β-alanine: Diastereomer B (16-5c)

N-[3(R)-[2-(4-Pyridyl)ethyl)-2-piperidone-1-yl]acetyl-3-(3-fluoro-phenyl)-β-alanine ethyl ester: Diastereomer A (16-6b)

N-[3(R)-[2-(4-Pyridyl)ethyl]-2-piperidone-1-yl]acetyl-3(R,S)-(3-Pyridyl)-β-alanine ethyl ester Dihydrochloride (17-2)

N-[3(R)-[2-(4-Pyridyl)ethyl]-2-piperidone-1-yl]acetyl-3(R,S)-3-Pyridyl)-β-alanine (17-3)

N-[3-R-[2-(4-Pyridyl)ethyl]-2-piperidone-1-yl]acetyl-3(S)-(3-Pyridyl)-β-alanine ethyl ester (17-5)

N-[3(R)-[2-(4-Pyridyl)ethyl]-2-piperidone-1-yl]acetyl-3(S)-(3-Pyridyl)-β-alanine (17-6)

N-[3(R)-[2-(4-Pyridyl)ethyl]-2-piperidone-1-yl]acetyl-3(S)-(3-Pyridyl)-β-alanine pivaloyloxy-methyl ester (17-7)

N-[3(R)-[2-(4-Pyridyl)ethyl]-2-piperidone-1-yl]acetyl-3-(S)-(3-Pyridyl)-β-alanine N,N-diethyl carbonylmethyl ester N-[3(R)-[2-(4-Pyridyl)ethyl]2-piperidone-1-yl]acetyl-3(S)-(3-Pyridyl)-β-alanine N-[3(R)-[2-(4-Pyridyl)ethyl-2-piperidone-1-yl]acetyl-3(R,S)-(3-ethynyl)-β-alanine ethyl ester (17-11)

N-[3(R)-[2-(4-Pyridyl]ethyl]-2-piperidone-1-yl]acetyl-3(R,S)-(3-ethynyl)-β-alanine (17-12)

N-[1-[4-(1-Imidazole)butyl]-2-piperidone-3-yl]acetyl-3(S)-(3-pyridyl)-β-alanine ethyl ester (18-5)

N-[1-[4-(1-imidazol)butyl]-2-piperidone-3-yl]acetyl-3(S)-(3-pyridyl)-β-alanine (18-6)

N-[1-(3-(1-Imidazole)propyl)-2-piperidone-3(R)-yl]acetyl-3(R)-(2-phenethyl)-β-alanine (19-7)

[N'-[N-[2-(Pyridine-4-yl)ethy]benzimidazolone]acetamido]-3-(3(R)-methyl)propanoic acid benzyl ester (20-6)

[N'-[N -[2-(Pyridine-4-yl)ethy]benzimidazolone]acetamido]-3-(3(R)-methyl)propanoic acid (20-7)

[[3(R)-(2-(Pyridin-4-yl)ethyl)-2-piperidon-1-yl]acetamido]-3-(2(R,S)-fluoro)propanoic acid propyl ester (21-3)

[[3(R)-(2-(Pyridin-4-yl)ethyl)-2-piperidon-1-yl]acetamido]-3-(2(R,S)-fluoro)propanoic acid (21-4)

and pharmaceutically acceptable salts thereof.

Specific salts of the above compounds include:

[3(R)-[2-(4-Pyridyl)ethyl]-2-piperidon-1-yl]acetyl-3(R)-methyl-β-alanine pivyloxymethyl ester, p-toluenesulfonate salt (8-3)

[3(R)-[2-(4-Pyridyl)ethyl]-2-piperidon-1-yl]acetyl-3(R)-methyl-β-alanine diethylaminoglycolamide ester p-toluenesulfonate salt (8-4)

[3(R-(−)-[2-(Pyridin-4-yl)ethyl]-2-piperidin-1-yl)acetyl-3(R)-[2-(phenyl)ethyl]-β-alanine trifluoroacetate (12-5)

[3(R)-[2(Pyridin-4-yl)ethyl]-2-piperidone-1]-acetyl-3(R)-methyl-β-alanine isobutyryl propiolate hydrochloride (8-5)

N-[3(R)-[2-(4-Pyridyl)ethyl]-2-piperidone-1-yl]acetyl-3-(S)-(3-Pyridyl)-β-alanine N,N-diethyl carbonylmethyl ester dihydrochloride (17-8)

N-[3(R)-[2-(4-Pyridyl)ethyl]2-piperidone-1-yl]acetyl-3(S)-(3-Pyridyl)-,-alanine dihydrochloride (17-9).

One test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets (2×108 per ml), fibrinogen (100 micrograms per ml (ug/ml)), $Ca^{2+}$(1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

The following representative compounds were tested and found to have $IC_{50}$ values within the range of 0.08 and 64 μM.

[3(R)-[1-(2-(Pyridin-4-yl)ethyl)-2-piperidon-3-yl] acetamido]-3-(3(R)-methyl)propanoic acid (1-10)

[3(R)-[1-(3-(Pyridin-4-yl)propyl)-2-piperidon-3-yl] acetamido]-3-(3(R)-methyl)propanoic acid (1-16)

[3(R)-[1-(2-(2-Aminopyridin-4-yl)ethyl)-2-piperidon-3-yl] acetamido]-3-(3(S)-(pyridin-3-yl))propanoic acid (1-20)

[3(R,S)-[1-(2-(Pyridin-4-yl)ethyl)-2-piperidon-3-yl] acetamido]-3-(3(S)-phenyl)propanoic acid (3-10)

[3(R,S)-[1-(2-(Pyridin-4-yl)ethyl)-2-piperidon-3-yl] acetamido]-3-(3(S)-phenyl)propanoic acid pivaloyloxymethyl ester (3-11)

[[3(R)-(2-(Pyridin-4-yl)ethyl)-2-piperidon-1-yl]acetamido]-3(S)-(4-hydroxy)butanoic acid (6-4)

3(R)-[2-(4-Pyridyl)ethyl]-2-piperidon-1-yl]acetyl-3(R)-methyl-β-alanine (8-2)

[3(R)-[2-(4-Pyridyl)ethyl]-2-piperidon-1-yl]acetyl-3(R)-methyl-β-alanine pivyloxymethyl ester, p-toluenesulfonate salt (8-3)

[3(R)-[2-(4-Pyridyl)ethyl]-2-piperidon-1-yl]acetyl-3(R)-methyl-β-alanine diethylaminoglycolamide ester p-toluenesulfonate salt (8-4)

[3(R)-[2-(Pyridin-4-yl)ethyl]-2-piperidon-1-yl]acetyl-2(S)-amino-β-alanine (9-6)

(3(R)-[(2-Amino-4-pyridyl)ethyl]-2-piperidon-1-yl)acetic-β-alanine (10-8)

[3(R)-[2-(Pyridin-4-yl)ethyl]-2-piperidon-1-yl]acetyl-3(R)-3-fluoro-benzyl-β-alanine (11-7)

[3(R)-[2-(Pyridin-4-yl)ethyl]-2-piperidon-1-yl)acetyl-3(R)-3,4-methyl-enedioxyphenylethyl-β-alanine (11-13)

[3(R)-[2-(Pyridin-4-yl)ethyl]-2-piperidon-1-yl)acetyl-4-chlorobenzyl-β-alanine (11-15)

[3(R)-[2-(Pyridin-4-yl)ethyl]-2-piperidon-1-yl]acetyl-3(R)-(1,1-diphenylmethyl)-β-alanine (11-19)

3-(R)-[2-(Pyridin-4-yl)ethyl]-2-piperidon-1-yl]acetyl-aspartyl α-[2-(4)methoxyphenyl)ethyl]amide (13-5)

3-(R)-[2-(Pyridin-4-yl)ethyl]-2-piperdinon-1-yl]acetyl-aspartyl-α-[bis-2-phenyl)ethyl]amide (13-7)

3(R,S)-[3(R)-[2-(pyridin-4-yl)ethyl]-2-piperidone-1-yl] acetamido-3-(3,3,-dimethyl-1-butynyl)propanoic acid (15-8)

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Compounds of the present invention are chiral; included within the scope of the present invention are racemic mixtures and separated enantiomers of the general formula. Furthermore, all diastereomers, including E, Z isomers, of the general formula are included in the present scope. Furthermore, hydrates as well as anhydrous compositions and polymorphs of the general formula are within the present invention.

Prodrugs, such as ester derivatives of described compounds, are compound derivatives which, when absorbed into the bloodstream of a warm-blooded animal, cleave in such a manner as to release the drug form and permit the drug to afford improved therapeutic efficacy.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

The term "alkyl" means straight or branched alkane containing 1 to about 10 carbon atoms, e.g., methyl, ethyl, n-propyl, isopropyl, n-butyl, isobutyl, sec-butyl, tert-butyl, pentyl, iso-amyl, hexy, octyl radicals and the like, straight or branched alkene containing 2 to about 10 carbon atoms, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like, or straight or branched alkyne containing 2 to about 10 carbon atoms, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "aryl" means a 5- or 6-membered aromatic ring containing 0, 1, or 2 heteroatoms selected from O, N, and S, e.g., phenyl, pyridine, pyrimidine, imidazole, thiophene, oxazole, isoxazole, thiazole, and amino- and halogen- substituted derivatives thereof.

The terms "alkyloxy" or "alkoxy" include an alkyl portion where alkyl is as defined above, e.g., methyloxy, propyloxy, and butyloxy.

The terms "arylalkyl" and "alkylaryl" include an alkyl portion where alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit. Examples of arylalkyl include benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include toluene, ethylbenzene, propylbenzene, methylpyridine, ethylpyridine, propylpyridine, butylpyridine, butenylpyridine, and pentenylpyridine.

The term "halogen" includes fluorine, chlorine, iodine and bromine.

The term "oxy" means an oxygen (O) atom. The term "thio" means a sulfur (S) atom. Under standard nomenclature used throughout this disclosure, the terminal portion of the designated side chain is described first followed by the adjacent functionality toward the point of attachment. For example, a $C_{1-6}$ alkyl substituted with $C_{1-5}$ alkylcarbonylamino is equivalent to

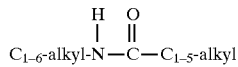

Amino acids suitable for compounds of the present invention include naturally occurring L- or D-amino acids include, for example, those naturally occurring L-amino acids present in humans, e.g., protein amino acids, including L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine, and those naturally occurring D-amino acids which are non-protein amino acids, such as those found, for example, in antibiotic substances produced by bacteria and fungi, including D-valine, D-asparagine, D-glutamate, D-ornithine, D-phenylalanine, D-leucine, D-cysteine, and D-aspartate. (see Zubay "BIOCHEMISTRY" Addison-Wesley Publishing Company, Inc. (Reading, Mass.) 1983 pp. 867–870 and Stryer "BIOCHEMISTRY" W.H. Freeman and Company (New York, N.Y.) 3rd Edition 1988 pp. 16–21).

In the schemes and examples below, various reagent symbols have the following meanings:

BOC (or Boc): t-butyloxycarbonyl

Pd-C: Palladium on activated carbon catalyst

DMF: Dimethylformamide

DMSO: Dimethylsulfoxide

CBZ: Carbobenzyloxy $CH_2Cl_2$: Methylene chloride $CHCl_3$: chloroform

BOP: Benzotriazol-1-yloxytris(dimethylamino) phosphonium, hexafluorophosphate

EDC: 1-(3-Dimethylaminopropyl)-3-ethylcarbodiimide hydrochloride

Oxone: potassium peroxymonosulfate

LDA: Lithium diisopropylamide

The compounds of the present invention can be administered in such oral forms as tablets, capsules (each of which includes sustained release or timed release formulations), pills, powders, granules, elixirs, tinctures, suspensions, syrups, and emulsions. Likewise, they may be administered in intravenous (bolus or infusion), intraperitoneal, subcutaneous, or intramusculsar form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gp IIb/IIIa on the platelet membranes and fibrinogen adsorbed to the surface of the circuit. (Gluszko et al., Amer. J. Physiol., 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty or coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.01–100 mg/kg/day and most preferably 0.01–20 mg/kg/day. Typically, oral dosages for an adult patient are, for example, 1 mg, 10 mg or 100 mg. Intravenously, the most preferred doses will range from about 1 to about 10 mg/kg/minute during a constant rate infusion. Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be coadministered with suitable anticoagulation agents or thrombolytic agents such as plasminogen activators or streptokinase in the treatment of various vascular pathologies. They may also be combined with heparin, aspirin, or warfarin. Coadministration includes administration together or separately in order to achieve beneficial thrombosis prevention or thrombolysis.

The novel compounds of the present invention were prepared according to the procedure of the following examples. The most preferred compounds of the invention are any or all of those specifically set forth in these examples. These compounds are not, however, to be construed as forming the only genus that is considered as the invention, and any combination of the compounds or their moieties may itself form a genus.

The examples which follow illustrate procedures for preparing compounds of the invention where X is a 5- or 6-membered monocyclic aromatic ring system, using starting materials such as vinyl pyridine, imidazole, etc.

Compounds of the invention where X is a 9-membered polycyclic aromatic fused ring system can be prepared by reacting a substituted 5-membered ring starting material such as 2-amino-3-bromothiophene, 2-nitro-3-bromothiophene, 2-amino-3-bromopyrrole, and 2-amino-3-bromofuran, with an appropriate compound under suitable ring closure conditions to effect formation of the 9-membered fused ring system.

Compounds of the invention where X is a 10-membered polycyclic aromatic ring system can be prepared using a starting material such as naphthyridin (Hamada, Y. et al., *Chem. Pharm. Bull. Soc.*, 1971, 19(9), 1857–1862), or by reacting an aminoaldehyde pyridine with a suitable ketone under suitable ring closure conditions to effect formation of the 10-membered fused ring system.

The examples also illustrate procedures for preparing compounds of the invention where B is —$(CH_2)_m C(O)NR^3 (CH_2)_n$—, e.g. —$CH_2C(O)NH$—.

To make compounds where B is —$(CH_2)_m NR^3 C(O) (CH_2)_n$—, e.g. —$CH_2NHC(O)CH_2$—, an acid such as compound 1–8 can be subjected to a Curtius reaction to form the amine, and subsequent condensation to give the final product. To make compounds where B is —$(CH_2)_m NR^3 (CH_2)_n$—, e.g. —$CH_2NHCH_2$—, an acid such as compound 1–8 can be reduced to its corresponding alcohol with borane, the alcohol converted to a bromide with carbon tetrabromide/phosphorous tribromide, and the bromide alkylated to form the final product.

The examples also illustrate procedures for preparing compounds of the invention where A is

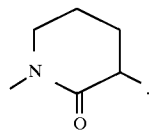

To make compounds where A is

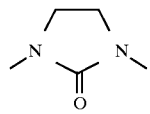

the commercially available starting material

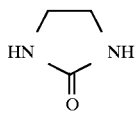

can be used and alkylated to produce the final product.

To make compounds where A is

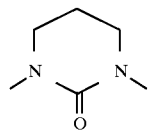

the commercially available starting material tetrahydropyrimidin-2-one

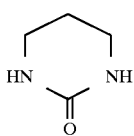

can be used and alkylated to produce the final product.

To prepare compounds where A is

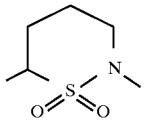

starting materials such as

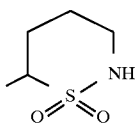

prepared according to E. H. White et al., *J.O.C.* 52 p. 2162 (1987) can be used.

To prepare compounds where A is

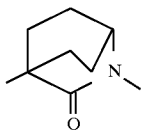

starting materials such as compound 124 in U.S. Pat. No. 5,281,585, col. 53, line 25, and col. 79, lines 50–61, can be used.

To prepare compounds where A is

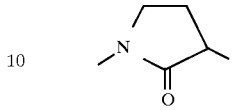

starting materials such as compound 19 in U.S. Pat. No. 5,281,585, col. 26, line 5, and col. 58, lines 5–24, can be used.

The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

3(R)-[2-(4-Pyridyl)ethyl]-2-piperidon-1-yl]acetyl-3(R)-methyl-β-alanine (compound 8-2) and (R)-Quininium [3(R)-[2-(pyridin-4-yl)ethyl]-2-piperidon-1-yl]acetate (compound 9-1) are prepared as follows:

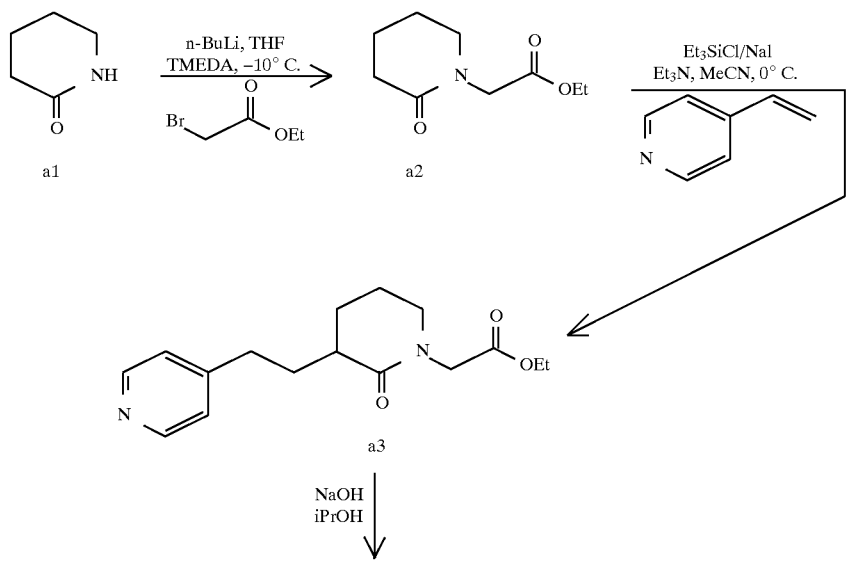

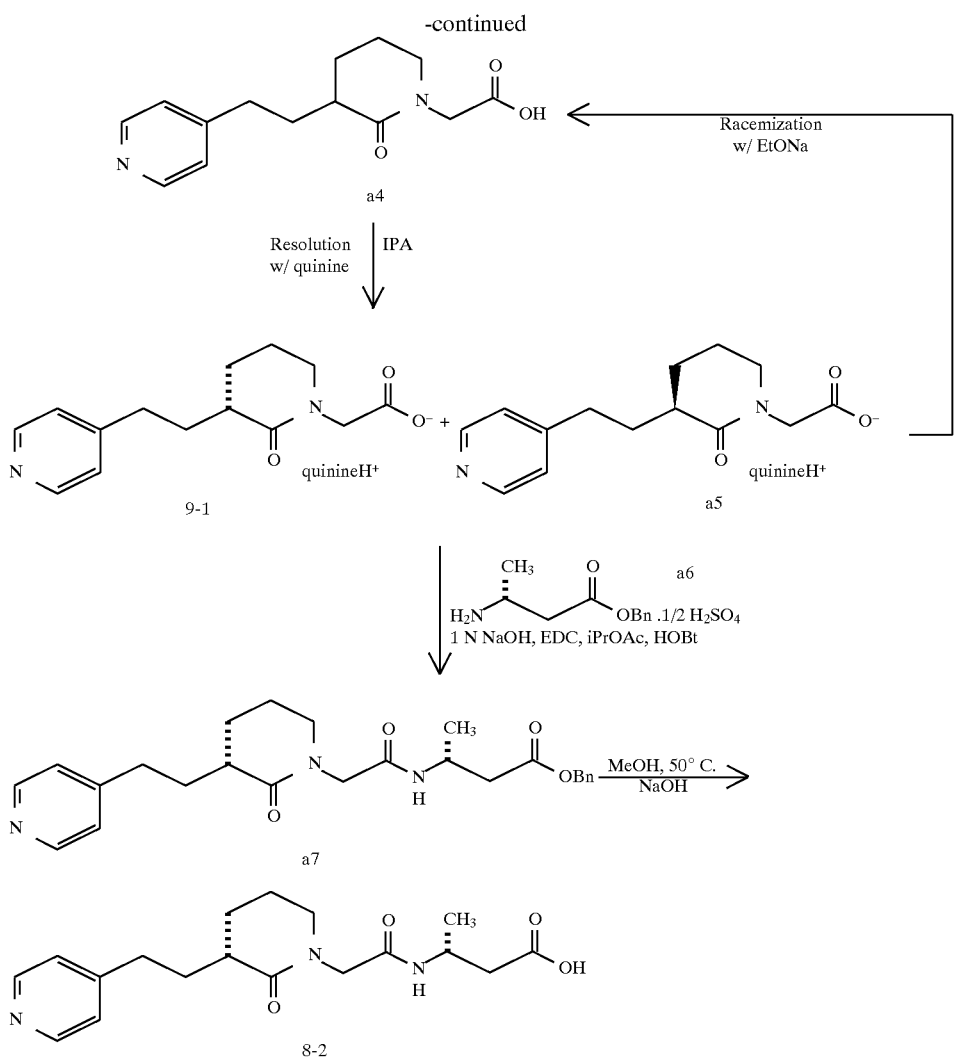

Preparation of ethyl (2-piperidon-1-yl]acetate (a2)

A 5 L four-necked round bottom flask was charged with 2-piperidone al (160.00 g, 1.614 mol), THF (1.44 L) and TMEDA (206.3 g, 1.775 mol). The mixture was stirred until all the solid dissolved, then 3 Å molecular sieves (26 g) were added. After stirring overnight, the mixture was filtered and the molecular sieves were washed with THF (0.48 L).

The combined filtrate was transferred to a dry 5 L four-necked round bottom flask equipped with a mechanical stirrer, an addition funnel, nitrogen inlet, cooling unit and a thermometer probe. The solution was cooled to −10° C. and n-butyllithium (1.6M in hexane, 1.06 L, 1.695 mol) was slowly added over a 60 min period, keeping the internal temperature less than 0° C. The mixture turned milky when ~50% of n-BuLi was charged. n-Butyllithium could be charged over 2–4 h while maintaining the internal temperature <5° C. without deterioration on the final yield. The only drawback was the slight increase in viscosity of the milky mixture.

After the addition, the reaction mixture was stirred at 0°-5° C. for 1 h. The reaction mixture was cooled to −10° C., and ethyl bromoacetate (283.1 g, 1.695 mol) was added over 15 min while maintaining the internal temperature less than 0° C. Ethyl bromoacetate could be charged over 0.5–1 h while maintaining the internal temperature <20° C. without deterioration on the final yield. The reaction mixture was stirred at 0° C. for 15 min and then allowed to warm to 23° C. and aged at this temperature for a 2 h period (or overnight if needed).

The reaction mixture was cooled to between −5° and 0° C. and quenched into a solution of NaCl (170 g) in 2N HCl (1.78 L), keeping the internal temperature less than 20° C. The resulting aqueous phase had a pH of 6.

The mixture was transferred to a 12 L separatory funnel and the two layers were separated. The aqueous layer was extracted with i-propyl acetate (3×1 L).

The combined organic layers were concentrated to near dryness and then azeotropically dried with acetonitrile (3×600 mL) (50° C., house vacuum). The mixture was filtered to remove a small amount of NaCl after the azeotropic distillation. The filter cake was washed with 500 mL acetonitrile. The brown solution was used as is in the next step. Pure solid product was isolated by crystallization from isopropyl acetate/hexane.

mp: 70°–71° C.

$^1$HNMR (CDCl$_3$, 250 MHz) δ: 1.27 (t, J=7.1 Hz, 3H), 1.85 (br m, 4H), 2.42 (br m, 2H), 3.35 (br m, 2H), 4.10 (s, 2H), 4.19 (q, J=7.1 Hz, 2H).

$^{13}$C NMR (CDCl$_3$, 63 mHz) δ: 14.1, 21.3, 23.1, 32.1, 48.6, 49.2, 61.1, 169.1, 170.4.

Preparation of ethyl [(±)3-[2-(pyridin-4-yl)ethyl]-2-piperidon-1-yl]acetate (a3)

A 250 mL three-necked round bottom flask equipped with a stirrer, nitrogen inlet, cooling unit and a thermometer probe was charged with piperidone-ester a2 (55.6 g, 108.0 mmol; 36 wt %; from step 1), acetonitrile (63.0 mL), anhydrous sodium iodide (17.81 g, 118.8 mmol) and triethylamine (13.11 g, 129.6 mmol). The mixture was stirred until all the solid dissolved.

The solution was cooled to 0° C. and chlorotriethylsilane (17.91 g, 19.94 mmol) was added over 5 min, keeping the internal temperature below +5° C., and then stirred at 20° C. for 1–2 h.

The resulting mixture was cooled to −5°–0° C., and 4-vinylpyridine (13.09 g, 124.2 mmol) was added dropwise over a 2 h period, while keeping the internal temperature below 0° C. The reaction was aged at 0° C. for 1–2 h, then quenched by slow addition (10 minutes) into a cold (0° C.) solution of 1N HCl (140 mL), while keeping the internal temperature <20° C. The final pH was 1.5–2.5.

The acidic solution (pH ~2) was extracted with 50% IPAC/Hexane (2×160 mL). Piperidone-ester a2 (5–7%), triethylsiloxane and residual neutral species were removed during the extractions.

To the aqueous solution was added IPAC (1×120 mL) and the mixture was cooled to 5°–10° C. With vigorous stirring, it was then basified to pH 9.5–10 by the slow addition of solid sodium bicarbonate (10 g; to pH 6) and 5N NaOH (~22 mL; to pH 9.7). The layers were separated.

The aqueous solution was extracted with toluene (2×150 mL). About 0.1% product remained in the aqueous layer after the extractions.

The combined organic layers were washed with saturated aqueous sodium bicarbonate (3×50 mL). Three washes were required to remove 95+% of $Et_3N \cdot HI/NaI$. Less than 0.5% of product was lost to the bicarbonate washes. The resulting organics has a total volume of 460 mL and a KF of 5.1 mg/mL.

The organic layer was azeotropically dried by distillation at 60° C. under reduce pressure. After 450 mL distilled out (final KF=<100 mg/mL), distillation was terminated and 150 mL dry toluene (total volume=200 mL) and 12 g of silica (60–200 mesh) were added. After stirring for 1 h, the mixture was filtered and the filter cake was washed with 100 mL toluene. Significant amounts of colored, polar, gummy impurities were removed by the silica treatment.

The combined filtrate was assayed to contain product a3. It was concentrated in vacuo (50° C., 100 mBar). After distilling most of the solvent, the batch was flushed with IPA (3×100 mL) to give a final concentration of 25 wt % (86 g) in IPA. This solution was used as is in the next step.

MS(EI) m/z 290 ($M^+$).

$^1$H NMR (CDCl$_3$) δ1.09 (t, J=7.1 Hz, 3H), 1.50 (m, 1H), 1.60–1.90 (m, 2H), 2.04 (m, 1H), 2.20 (m, 1H), 2.54 (m, 2H), 3.10–3.30 (m, 2H), 3.77 (A of AB, J=17.2 Hz, 1H), 4.01 (q, J=7.1 Hz, 2H), 4.03 (B of AB, J=17.2 Hz, 1H), 6.99 (d, J=6.0 Hz, 2H), 8.30 (d, K=6.0 Hz, 2H).

$^{13}$C NMR (CDCl$_3$) δ9.7, 17.3, 22.2, 27.9, 28.0, 36.2, 44.6, 44.9, 56.6, 119.5, 145.2, 146.6, 164.7, 168.2.

Preparation of [(±)3-[2-(pyridin-4-yl)ethyl]-2-piperidon-1-yl]acetic acid (a4)

To a 25 wt % solution of the pyridine-ethyl ester a3 (21.3 g, 73.35 mmol) in isopropyl alcohol was added 48.8% aqueous sodium hydroxide (7.82 g, 95.36 mmol) at 20° C. under nitrogen over a 5 min period.

The reaction mixture was stirred for 2 h until complete consumption of a3 was observed as monitored by HPLC.

The mixture was cooled to 5°–10° C., seeded with 50 mg of NaCl and then quenched by the slow addition of 36.6% aqueous hydrochloric acid (9.50 g, 95.36 mmol) over a 10 min period, while maintaining the internal temperature <15° C. The final pH was 5.45.

To the resulting mixture was added MeOH (20 mL), THF (40 mL) and Solka-Floc (5 g). After stirring for 30 min at ambient temperature, the mixture was filtered through a pad of Solka-Floc (5 g, wetted with 10 mL EPA) in a 150 mL sintered glass funnel (10–15 mm).

The filter cake was washed with a mixture of IPA/THF/MeOH (50 mL:20 mL:10 mL). Filtration of the wash took about 3 min.

The combined filtrate contained acid a4 in quantitative yield as determined by HPLC analysis.

The filtrate was dried by azeotropic distillation under vacuum at 50° C. After distilling most of the solvents, the mixture was flushed several times with IPA (3×50 mL) to give a final concentration of 30 wt % (final weight=60 g) and a KF of <1000 mg/mL.

The mixture was seeded with 9 and stirred until a seed bed was formed. Hexane (20 g, 30.5 mL) was then added over a 1 h period and then aged for 12 h. After cooling to 10° C. and stirring for 0.5 h, the solid was collected by filtration through a sintered glass funnel. The filter cake was washed with 40:60 IPA:hexanes (50 mL) and vacuum-dried under a stream of nitrogen to give a4 as a light beige crystalline solid.

mp 144°–145° C.

MS(EI) m/z 263 ($MH^+$).

$^1$H NMR (CDCl$_3$) δ1.70 (m, 1H), 1.80–2.05 (m, 4H), 2.20 (m, 1H), 2.40 (m, 1H), 2.78 (t, J=8.0 Hz, 2H), 3.35 (m, 1H), 3.47 (m, 1H), 3.90 (A of AB, J=17.1 Hz, 1H), 4.32 (B of AB, J=17.1 Hz, 1H), 7.27 (d, J=6.2 Hz, 2H), 8.49 (d, J=6.0 Hz, 2H).

$^{13}$C NMR (CDCl$_3$) δ17.4, 22.4, 28.1, 28.4, 36.3, 44.9, 45.1, 120.4, 142.7, 149.8, 167.7, 168.3.

Anal. Calcd for $C_{14}H_{18}O_3N_2$: C, 64.11; H, 6.92; N, 10.68. Found: C, 64.15; H, 7.16; N, 10.66.

Preparation of Quininium [3(R)-(−)-[2-(pyridin-4-yl)ethyl]-2-piperidon-1-yl]acetate (9-1) via resolution of [(±)3-[2-(pyridin-4-yl)ethyl]-2-piperidon-1-yl]acetic acid (a4) with quinine In a 250 mL round bottom flask, pyridine acid a4 (12.04 g, 96.6% pure, 44.34 mmol), quinine (14.89 g, 45.90 mmol) and isopropyl alcohol (80.8 mL; KF <0.1 mg/mL) were combined. The mixture was heated at 65° C. for 15 min under a nitrogen atmosphere to dissolve all the solid. The resulting solution was allowed to cool to 20° C. When the solution reached 45° C., it was seeded with ~10 mg of 99.5% ee quinine salt 9-1. After stirring overnight, the mixture was cooled to 5°–6° C. and aged for 0.5–1 h.

The solid was collected on a medium porosity fritted funnel under a nitrogen blanket. The filter cake was washed with 50 mL cold (5°–10° C.) THF:hexane (50:50) and then dried under vacuum with a nitrogen sweep to give 12.72 g of 9-1 as a white solid.

Preparation of (R)-Quininium [3(R)-[2-(pyridin-4-yl)ethyl]-2-piperidon-1-yl]acetate (9-1)

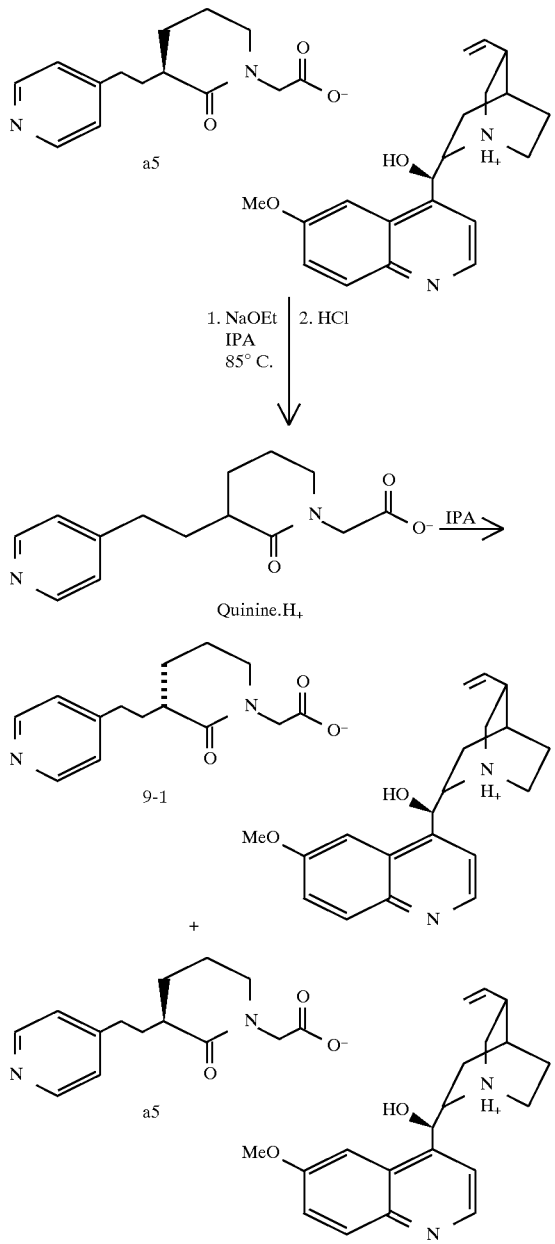

A three-necked 3 L round bottom flask equipped with a mechanical stirrer, condenser, nitrogen gas inlet and thermometer probe was charged with pyridine acid quinine salt mother liqour from the resolution step (1.84 L, 77.7 g/L, 545 mmol) and solid sodium ethoxide (67 g, 981 mmol).

The mixture was heated at reflux (83°–85° C.) for 5 h.

The resulting mixture was cooled to 15° C. and 37% hydrochloric acid (56 mL) was slowly added until pH 8.1–8.3 (at 23° C.).

To the batch was added THF (1.84 L) and Solka-Floc (80 g). After stirring for 1 h, the mixture was filtered through a layer of Solka-Floc (40 g, prewetted with THF) in a sintered glass funnel (medium porosity) to remove NaCl and then washed with THF (300 mL).

The filtrate was concentrated under vacuum at 45° C. and flushed with toluene (3×300 mL) to remove water, followed by isopropyl alcohol (3×300 mL) to remove toluene. The KF of the mixture should be less than 500 mg/mL after the flushes. Isopropyl alcohol (750 mL) was added to the batch to give a final concentration of 3 mL EPA per gram of quinine salt.

The mixture was heated at 70°–75° C. for 15–30 min under a nitrogen atmosphere to dissolve all the solid. The resulting solution was allowed to cool gradually to ambient. When the batch temperature reached 45° C., the mixture was seeded with 0.1 g of quinine salt 9-1.

After stirring overnight at 22° C., the mixture was cooled to 5°–10° C. and aged for 0.5 h. The batch was filtered through a sintered glass funnel (medium porosity) and the wet cake was washed with cold hexane/THF (1:1, 10° C., 2×350 mL) and then dried under vacuum under a nitrogen blanket.

Preparation of [3(R)-(–)-[2-(Pyridin-4-yl)ethyl]-2-piperidon-1-yl]acetyl-3-(R)-methyl-β-alanine benzyl ester (a7)

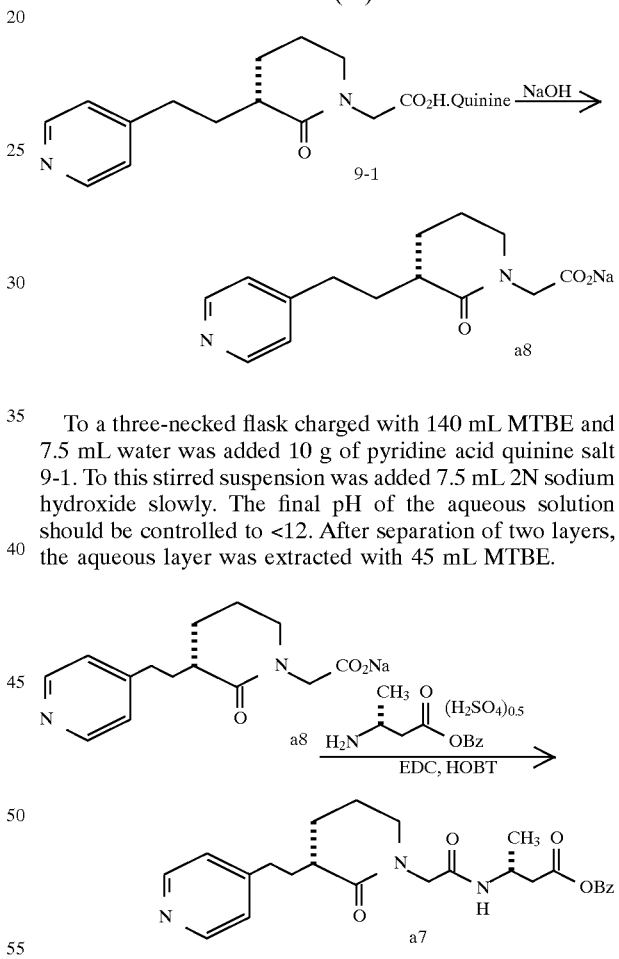

To a three-necked flask charged with 140 mL MTBE and 7.5 mL water was added 10 g of pyridine acid quinine salt 9-1. To this stirred suspension was added 7.5 mL 2N sodium hydroxide slowly. The final pH of the aqueous solution should be controlled to <12. After separation of two layers, the aqueous layer was extracted with 45 mL MTBE.

The pH of the aqueous solution of pyridine acid sodium salt a8 (14 mmol) from the last step was adjust with 1N HCl if necessary to 9–11.5. To this stirred solution of pyridine acid sodium salt was added benzyl 3(R) aminobutyrate hemisulfate (Celgene; 3.48 g, 14.36 mmol), isopropyl acetate (59 mL), HOBT (0.14 g, 1 mmol) and EDC (3.29 g, 17.16 mmol). The mixture was stirred at room temperature for 2–3 hrs until all the pyridine acid was consumed as judged by HPLC.

After the reaction was complete, the two layers were separated. The aqueous layer was extracted with another

Preparation of 3(R)-[2-(4-Pyridyl)ethyl]-2-piperidon-1-yl]acetyl-3(R)-methyl-β-alanine (8-2)

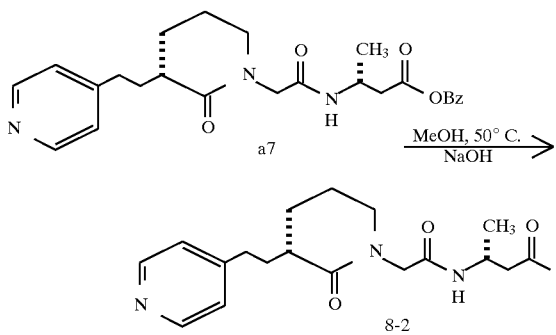

The pyridine amide benzyl ester a7 solution in isopropyl acetate from last step was concentrated under vacuum (40° C. pot temperature) to a volume of 8 L and then 10 L methanol was added and the solution concentrated again to 8 L (KF <500 mg/mL). The methanol flush (temperature ≦50° C., 10 cm Hg) was repeated four times until all the isopropyl acetate was replaced with methanol (maximum IPAC content=50 mol % relative to benzyl ester). The ester is hydrolyzed to form the corresponding acid 8-2.

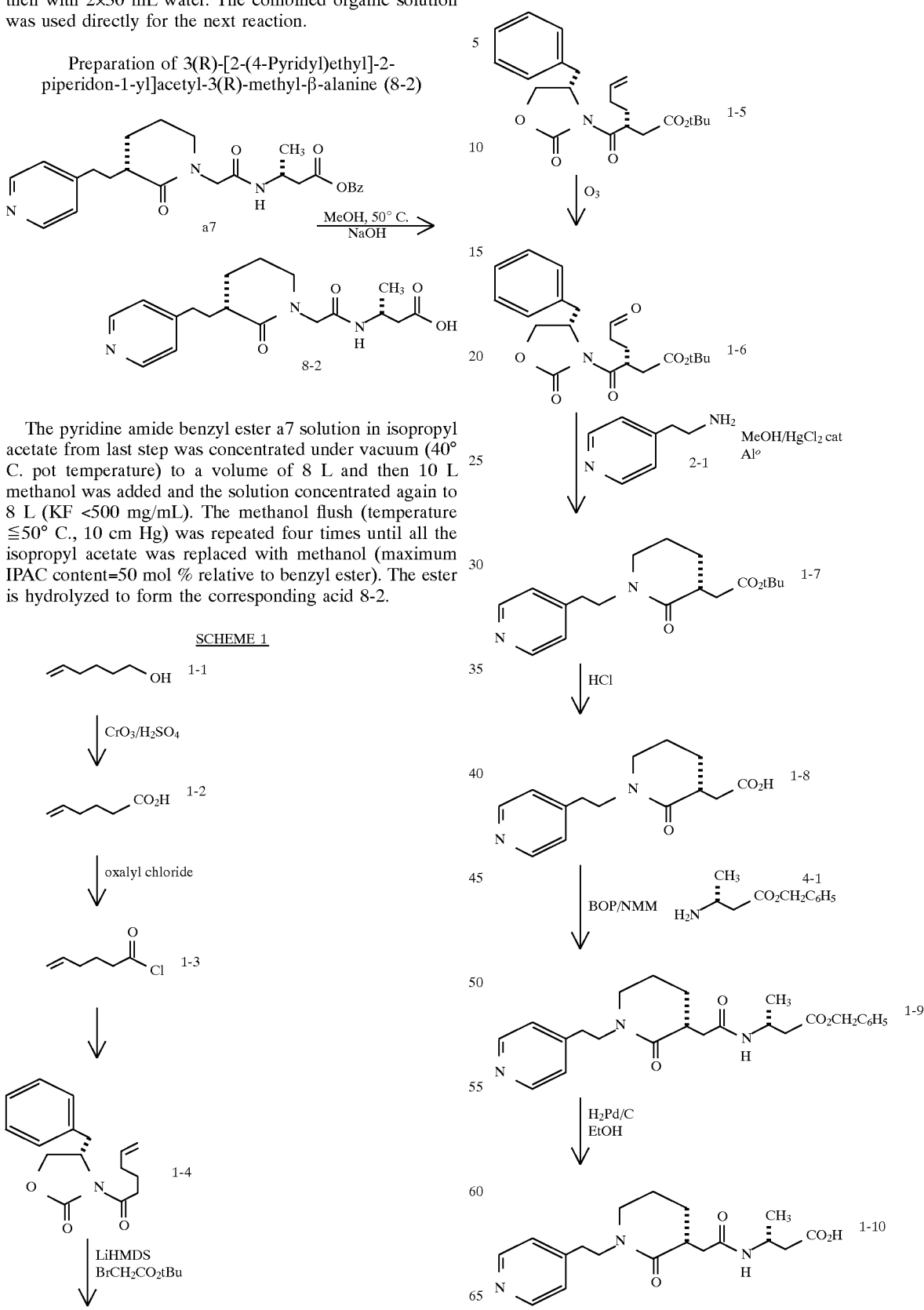

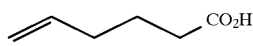

5-Hexenoic acid (1-2)

A solution of 5-hexene-1-ol (Aldrich, 25 g, 0.25 mol) in acetone (1 L) was cooled to 0° C. and treated with a quantity of Jones reagent sufficient to obtain a persistent orange solution (~150 mL). The excess reagent was quenched with isopropyl alcohol and the solvents were removed in vacuo. The greenish residue was dissolved in $H_2O$ and extracted with EtOAc. The EtOAc layer was washed with 10% $KHSO_4$ solution, brine, dried with $MgSO_4$, filtered and carefully evaporated in the absence of external heat to give 1-2 as a clear oil.

$^1$H NMR (400 MHz, $CDCl_3$) δ5.8 (m, 1H), 5.0 (m, 2H), 2.38 (t, 2H), 2.10 (m, 2H), 1.75 (m, 2H).

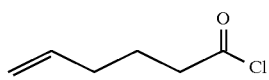

5-Hexenoyl chloride (1-3)

A solution of 1-2 (6.5 g, 57 mmol) in $CHCl_3$ (25 mL) was treated with oxalyl chloride (12.4 mL), then with a single drop of DMF. The reaction bubbled vigorously and became pale yellow. After 1.5 h, the solvents were removed via rotoevaporator without applying external heat to the flask. $CHCl_3$ was added to the oil and the resulting solution was evaporated in the same manner as before to give 1-3 as a clear oil.

$^1$H NMR (400 MHz, $CDCl_3$) δ5.8 (m, 1H), 5.05 (m, 2H), 2.9 (t, 2H), 2.15 (m, 2H), 1.8 (m, 2H).

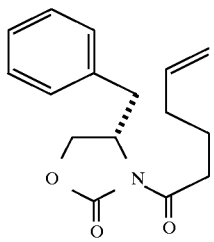

N-(5-Hexenoyl)-4-(S) benzyl oxazolidinone (1-4)

A solution of 4-(S)-benzyl oxazolidinone (10 g, 57 mmol) in THF (100 mL) was cooled to -78° under argon. A 2.1M solution of n-butyllithium (27.1 mL) was added dropwise, while the temperature of the reaction was maintained at -78° C. The oxazolidinone anion was treated dropwise with 1-3 (7.5 g, 57 mmol), then warmed to room temperature over 30 min. The reaction was quenched with 50 mL pH7 phosphate buffer and diluted with 150 mL EtOAc. The layers were separated. The aqueous layer was acidified to pH7 with 10% $KHSO_4$ solution, and extracted with EtOAc. The EtOAc layers were combined, washed with pH7 buffer, saturated $NaHCO_3$ solution, and brine, then dried over $MgSO_4$, filtered and evaporated. Column chromatography of the residue (silica gel, 20–40% EtOAc/Hexanes) gave 1-4 as a clear, colorless oil.

$R_f$ (20% EtOAc/Hexanes) 0.41.

$^1$H NMR (400 MHz, $CDCl_3$) δ7.25–7.2 (m, 5H), 5.8 (m, 1H), 5.0 (2d, 2H), 4.65 (m, 1H), 4.2 (m, 2H), 3.3 (dd, 1H), 2.95 (m, 2H), 2.75 (dd, 1H), 2.15 (m, 2H), 1.8 (m, 2H).

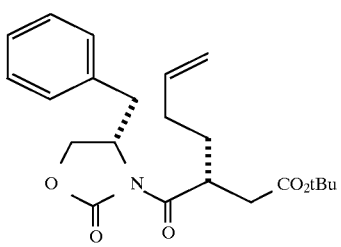

N-[5-Hexen-2-(R)-(t-butyl acetate)-oyl]-4-(S) benzyl oxazolidinone (1-5)

A solution of 1-4 (3.16 g, 11.6 mmol) in THF (50 mL) was placed under argon and cooled to -78° C. A 1M solution of $NaN(TMS)_2$ (13.9 mL, 13.9 mmol) was added via syringe while the temperature of the reaction was maintained below -60° C. The clear red solution was re-cooled to -78° C. and t-butyl bromoacetate (5.14 mL, 34.8 mmol) was added. After stirring for 0.5 h at -78° C., the reaction was allowed to warm to -30° C. over 0.5 h, then was re-cooled to -50° C., quenched with 10% $KHSO_4$ solution and diluted with EtOAc. The layers were separated and the organic layer was washed with $H_2O$, brine, dried over $MgSO_4$, filtered and evaporated. The crude product was chromatographed (silica gel, 20% EtOAc/Hexanes) to give 1-5 as a clear oil.

$R_f$ (30% EtOAc/Hexanes) 0.57.

$^1$H NMR (400 MHz, $CDCl_3$) δ7.3 (m, 5H), 5.8 (m, 1H), 5.0 (2d, 2H), 4.63 (m, 1H), 4.2 (m, 3H), 3.35 (dd, 1H), 2.8 (m, 2H), 2.5 (dd, 1H), 2.15 (m, 2H), 1.8 (m, 1H), 1.6 (m, 1H), 1.41 (s, 9H).

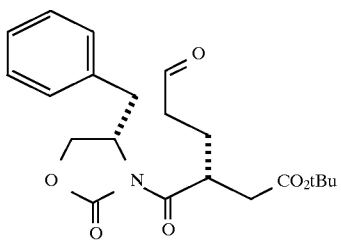

N-[5-Pentanal-2(R)(t-butyl acetate)-oyl]-4-(S) benzyl oxazolidinone (1-6)

A solution of 1-5 (3.4 g, 8.8 mmol) in $CH_2Cl_2$/MeOH (50 mL/50 mL) was cooled to -78° C. Pyridine (10 drops) was added and ozone was bubbled through the solution until it turned blue. After stirring for 10 minutes, argon was bubbled through the solution until it was colorless and Dimethylsulfide (1.3 mL, 17.6 mmol) was added. The cold bath was removed and the solution was warmed to room temperature. After stirring for 0.5 h the reaction was concentrated under vacuum and the residue was dissolved in EtOAc and washed with water five times to remove excess DMSO. The organic layer was dried ($MgSO_4$), filtered and evaporated to give 1-6 as a tan oil.

$R_f$ (20% EtOAc/Hexanes) 0.15.

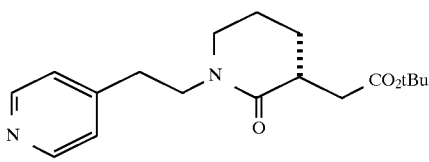

3(R)-[1-(2-(Pyridin-4-yl)ethyl)-2-piperidon-3-yl] acetate t-butyl ester (1-7)

A solution of 1-6 (3.3 g, 8.5 mmol) in MeOH (50 mL), in which was suspended finely chopped aluminum foil (2.3 g, 85 mmol), was treated with 2-1 (1.2 g, 10.2 mmol) and HgCl$_2$ (0.2 g). After 15 minutes a fine grey percipitate was formed and the reaction became warm. After stirring for 18 h the reaction was filtered through Solka-Floc and the cake was agitated and rinsed with MeOH (150 mL). The solution was evaporated to give a brown oil which was heated without solvent at 100° C. for 6 h. The oil was dissolved in EtOAc, and washed with 10% KHSO$_4$. The acidic aqueous layer was basified to pH 7 and extracted with EtOAc, and the organic layer was concentrated. The residue was chromatographed (silica gel, 10% EtOAc/Hexanes) to give 1-7 as a clear oil.

$R_f$ (10% MeOH/EtOAc) 0.28.

$^1$H NMR (400 MHz, CDCl$_3$) δ8.5 (d, 2H), 7.18 (d, 2H), 3.65–3.5 (m, 2H), 3.21 (m, 1H), 3.12 (m, 1H), 2.87 (t, 2H), 2.7 (dd, 1H), 2.65 (m, 1H), 2.45 (dd, 1H), 1.95 (m, 1H), 1.8 (m, 1H), 1.7 (m, 1H), 1.6 (m, 1H), 1.45 (s, 9H).

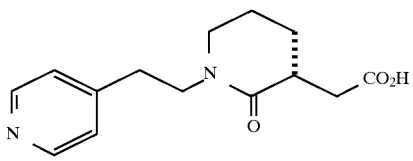

3(R)-[1-(2-(Pyridin-4-yl)ethyl)-2-piperidon-3-yl] acetate (1-8)

A solution of 1-7 (0.62 g, 1.9 mmol) in EtOAc (10 mL) was cooled to −78° C., saturated with HCl gas, then warmed to 0° C. Gas evolution was observed. After 20 minutes the solution was concentrated to give 1-8 as a tan solid.

$R_f$ (10:1:1 EtOH/H$_2$O/NH$_4$OH) 0.5.

$^1$H NMR (400 MHz, CD$_3$OD) δ8.75 (d, 2H), 8.1 (d, 2H), 3.8 (m, 1H), 3.65 (m, 1H), 3.4 (m, 2H), 3.2 (m, 2H), 2.6 (m, 3H), 1.95 (m, 2H), 1.8 (m, 1H), 1.75 (m, 1H).

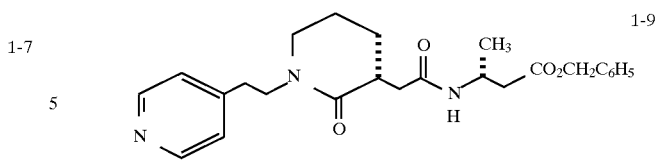

[3(R)-[1-(2-(Pyridin-4-yl)ethyl)-2-piperidon-3-yl] acetamido]-3-(3(R)-methyl)propanoic acid benzyl ester (1-9)

A slurry of 1-8 (0.56 g, 1.9 mmol) in acetonitrile (10 mL) was treated with benzyl 3-(R)-aminobutanoic acid (4-1) (prepared as described for compound 54 in U.S. Pat. No. 5,281,585), 0.46 g, 1.9 mmol), BOP reagent (1.0 g, 2.5 mmol), and NMM (0.73 mL, 6.6 mmol). After 20 minutes the reaction became homogenous. After 2 h the reaction was diluted with EtOAc and H$_2$O and the layers were separated. The organic layer was washed with brine, dried over MgSO$_4$, filtered and concentrated. The residue was chromatographed (silica gel, 10% MeOH/EtOAc) to give impure 1-9 which was further purified by dissolving in EtOAc and washing with 10% KHSO$_4$. The aqueous layer was neutralized to pH7 and extracted with EtOAc. The organic layers were combined, washed with brine, dried (MgSO$_4$), filtered and evaporated to give 1-9.

$R_f$ (10% MeOH/EtOAc) 0.37.

$^1$H NMR (400 MHz, CDCl$_3$) δ8.5 (d, 2H), 7.35 (m, 5H), 7.2 (d, 2H), 6.7 (m, 1H), 5.1 (s, 2H), 4.38 (m, 1H), 3.58 (m, 2H), 3.21 (m, 1H), 3.15 (m, 1H), 2.95 (m, 2H), 2.6 (m, 4H), 2.48 (m, 2H), 1.95 (m, 1H), 1.8 (m, 1H), 1.7 (m, 1H), 1.56 (m, 1H), 1.2 (d, 3H).

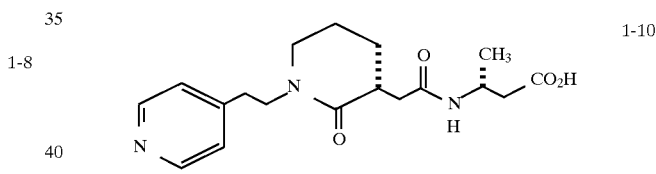

[3(R)-[1-(2-(Pyridin-4-yl)ethyl)-2-piperidon-3-yl] acetamido]-3-(3(R)-methyl)propanoic acid (1-10)

A solution of 1-9 (0.5 g, 1.14 mmol) in EtOH (10 mL) was treated with a slurry of 10% Pd/C in EtOH and placed under balloon pressure hydrogen atmosphere. The reaction was stirred for 1 h, then filtered through celite. The filter cake was rinsed with MeOH, the filtrate was concentrated to give a residue which was purified by chromatography (silica gel, 10/0.25/0.25 EtOH/NH$_4$OH/H$_2$O) to give 1-10 as a white solid.

$^1$H NMR (400 MHz, CD$_3$OD) δ8.42 (d, 2H), 7.38 (d, 2H), 4.22 (m, 1H), 3.6 (m, 3H), 3.3 (buried), 2.95 (t, 2H), 2.65 (m, 3H), 2.51 (dd, 1H), 2.4 (dd, 1H), 2.3 (dd, 1H), 1.9 (m, 1H), 1.85 (m, 1H), 1.7 (m, 1H), 1.55 (m, 1H), 1.4 (d, 3H).

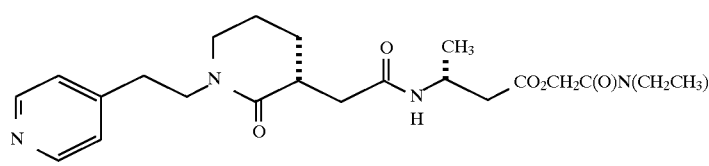

[3(R)-[1-(2-(Pyridin-4-yl)ethyl)-2-piperidon-3-yl]acetamido]-3-(3(R)-methyl)propanoic acid dimethylaminoglycolamide ester (1-11)

A slurry of 1-10 (0.083 g, 0.18 mmol) in DMF (2 mL) was treated with CsCO$_3$ (0.041 g, 0.126 mmol) and dimethylamino bromoacetamide (0.035 g, 0.18 mmol), prepared from bromoacetylbromide and diethyl amine as described for the preparation of methylhexylaminobromoacetamide used to prepare 1-2). After 18 h the reaction was diluted with EtOAc and washed with H$_2$O. The aqueous layer was concentrated and the residue was suspended in CH$_3$CN and filtered. The filtrate was concentrated to give 1-11 as a brown solid.

$^1$H NMR (400 MHz, CD$_3$OD) δ8.75 (d, 2H), 8.05 (d, 2H), 5.7 (s, 2H), 4.2 (m, 1H), 3.8 (m, 1H), 3.65 (m, 1H), 3.5–3.3 (m, 8H), 3.2 (t, 2H), 2.6 (m, 1H), 2.54 (m, 2H), 2.4 (m, 2H), 1.9 (m, 2H), 1.8 (m, 1H), 2.6 (m, 1H), 1.1 (m, 6H).

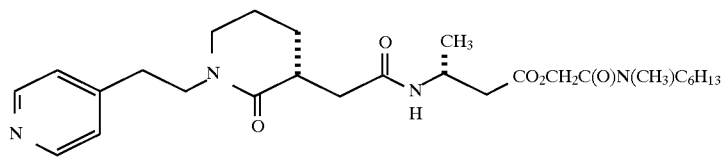

[3(R)-[1-(2-(Pyridin-4-yl)ethyl)-2-piperidon-3-yl]acetamido]-3-(3(R)-methyl)propanoic acid methylhexylaminoglycolamide ester (1-12)

A solution of methylhexylamine (Aldrich, 5 mL, 33 mmol) in CH$_2$Cl$_2$ was treated with triethylamine (5.5 mL, 39.6 mmol) and bromoacetylbromide (Aldrich, 2.9 mL, 33 mmol) for 1 h. The solution was washed with H$_2$O and brine, dried over MgSO$_4$, filtered and evaporated. Chromatography of the residue (silica gel, 30% EtOAc/Hexanes, R$_f$ 0.31) gave methylhexylaminobromoacetamide as a brown oil.

$^1$H NMR (400 MHz, CD$_3$Cl$_3$) δ3.83 (s, 2H), 3.35 (m, 2H), 3.0 (2s, 3H), 1.6 (2m, 2H), 1.3 (m, 6H), 0.9 (m, 3H).

A solution of 1-10 (0.083 g, 0.18 mmol) in DMF (2 mL) was treated with CsCO$_3$ (0.0041 g, 0.126 mmol) and methylhexylaminobromoacetamide (0.047 g, 0.18 mmol) as described for 1-11 to give 1-12 as a sticky solid.

$^1$H NMR (400 MHz, CD$_3$OD) δ8.7 (m, 2H), 8.05 (m, 2H), 5.65 (d, 2H), 4.2 (m, 1H), 3.8 (m, 1H), 3.7 (m, 1H), 3.4 (m, 4H), 3.25 (t, 2H), 2.6 (m, 1H), 2.5 (m, 2H), 2.4 (m, 2H), 1.9 (m, 2H), 1.9 (m, 2H), 2.6 (m, 2H), 1.4 (m, 2H), 1.3 (bs, 4H), 1.2 (d, 3H), 0.9 (m, 3H).

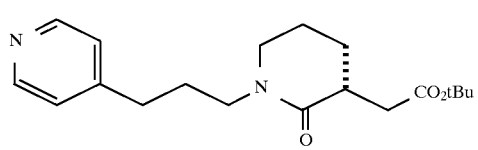

3(R)-[1-(3-(Pyridin-4-yl)propyl)-2-piperidon-3-yl]acetate t-butyl ester (1-13)

Compound 1-13 was prepared from 1-6 and 2-5 as described for the preparation of 1-7.

R$_f$ (10% MeOH/EtOAc) 0.25.

$^1$H NMR (400 MHz, CDCl$_3$) δ8.45 (d, 2H), 7.1 (d, 2H), 3.4 (m, 2H), 3.3 (m, 1H), 3.23 (m, 1H), 2.76 (dd, 1H), 2.62 (m, 2H), 2.45 (dd, 1H), 2.0–1.9 (m, 4H), 1.75 (m, 1H), 1.6 (m, 1H), 1.42 (s, 9H).

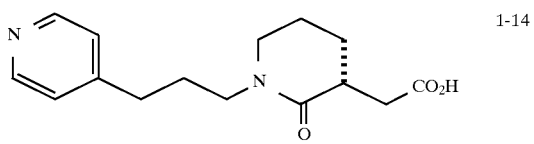

3(R)-[1-(3-(Pyridin-4-yl)propyl)-2-piperidon-3-yl]acetate (1-14)

Compound 1-13 was treated with HCl/EtOAc as described for the preparation of 1-8 to give 1-14 as a white solid.

R$_f$ (10:0.5:0.5 EtOH/NH$_4$OH/H$_2$O) 0.26.

$^1$H NMR (400 MHz, CD$_3$OD) δ8.75 (d, 2H), 8.0 (d, 2H), 3.55 (m, 1H), 3.45 (m, 1H), 3.35 (m, 2H), 3.0 (t, 2H), 2.65 (m, 3H), 2.01 (m, 2H), 1.95 (m, 2H), 1.8 (m, 2H).

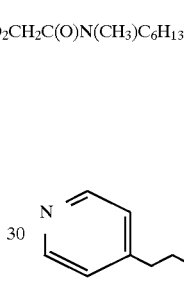
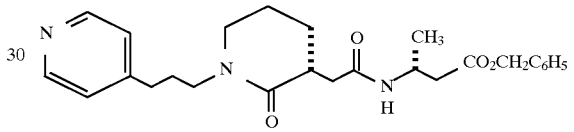

[3(R)-[1-(3-(Pyridin-4-yl)propyl)-2-piperidon-3-yl]acetamido]-3-(3(R)-methyl)propanoic acid benzyl ester (1-15)

Compound 1-14 was coupled with 4-1 (prepared as described for compound 54 in U.S. Pat. No. 5,281,585) as described for the preparation of 1-9 to give 1-15 as a yellow oil.

R$_f$ (10% MeOH/EtOAc) 0.33.

$^1$H NMR (400 MHz, CDCl$_3$) δ8.45 (d, 2H), 7.35 (m, 5H), 7.15 (d, 2H), 6.7 (d, 1H), 5.1 (s, 2H), 4.32 (m, 1H), 3.5–3.2 (m, 6H), 2.6–2.5 (m, 6H), 2.4 (m, 1H), 1.9 (m, 1H), 1.75 (m, 2H), 1.73 (m, 1H), 1.6 (m, 1H), 1.4 (d, 3H).

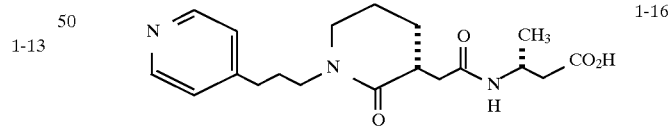

[3(R)-[1-(3-(Pyridin-4-yl)propyl)-2-piperidon-3-yl]acetamido]-3-(3(R)-methyl)propanoic acid (1-16)

Compound 1-15 was treated with H$_2$ and 10% Pd/Carbon as described for the preparation of 1-10 to give 1-16 as a white solid.

R$_f$ (10:1:1 EtOH/H$_2$O/NH$_4$OH) 0.76.

$^1$H NMR (400 MHz, CD$_3$OD) δ8.4 (d, 2H), 7.3 (d, 2H), 4.21 (m, 1H), 3.4 (m, 2H), 3.35 (m, 1H), 2.64 (m, 4H), 2.5 (dd, 1H), 2.35 (m, 2H), 1.9 (m, 4H), 1.75 (m, 1H), 1.6 (m, 1H), 1.18 (d, 3H).

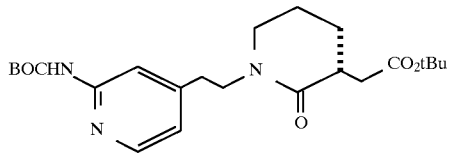

3(R)-[1-(2-(2-Aminopyridin-4-yl)ethyl)-2-piperidon-3-yl]acetate t-butyl ester (1-17)

Compounds 1-6 and 5-5 were treated as described for the preparation of 1-7 to give a mixture of 1-17 and uncyclized material as a solid. The solid was dissolved in a small amount of MeOH and heated to 80° C. After 4 h the crude product was absorbed to silica and chromatographed (silica gel, 10–20% Acetone/Hexanes) to give 1-17.

$R_f$ (20% EtOAc/Hexanes) 0.21.

$^1$H NMR (400 MHz, CDCl$_3$) δ8.85 (s, 1H), 8.2 (d, 1H), 7.84 (s, 1H), 6.85 (d, 1H), 3.7–3.5 (m, 2H), 3.2 (m, 1H), 3.15 (m, 1H), 2.9–2.8 (m, 2H), 2.78 (m, 1H), 2.65 (m, 1H), 2.42 (dd, 1H), 1.95 (m, 1H), 1.8 (m, 1H), 1.73 (m, 1H), 1.55 (m, 1H), 1.51 (s, 9H), 1.41 (s, 9H).

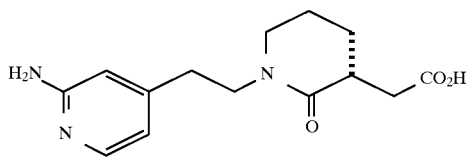

3(R)-[1-(2-(2-Aminopyridin-4-yl)ethyl)-2-piperidon-3-yl]acetate (1-18)

Compound 1-17 was treated as described for the preparation of 1-8 to give 1-18 as a pink solid.

$^1$H NMR (400 MHz, CD$_3$OD) δ7.71 (d, 1H), 6.84 (m, 2H), 3.7–3.5 (m, 2H), 3.4 (m, 1H), 3.35 (m, 1H), 2.9 (t, 2H), 2.62 (m, 3H), 1.95 (m, 1H), 1.9 (m, 1H), 1.8 (m, 1H), 1.7 (m, 1H).

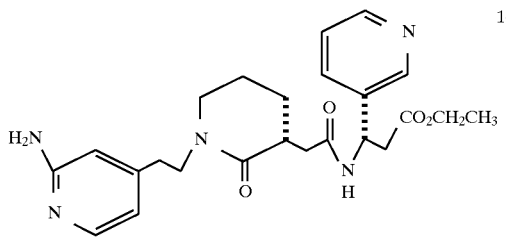

[3(R)-[1-(2-(2-Aminopyridin-4-yl)ethyl)-2-piperidon-3-yl]acetamido]-3-(3(S)-(pyridin-3-yl)) propanoic acid ethyl ester (1-19)

A solution of 1-18 (0.465 g, 1.48 mmol) and Ethyl 3-(S)-(3-pyridyl)propanoate (*J. Org. Chem.* 1993, 58, 7948. 0.3 g, 1.59 mmol) in DMF (14 mL) was treated with Hydroxybenztriazole (0.42 g, 3.1 mmol) and Dicyclohexyldicarboxamide (0.61 g, 2.96 mmol) and the pH of the solution was adjusted to 6 with NMM. After 4 h the solvent was removed in vacuo and the residue was chromatographed (silica gel, 2% CH$_3$OH/CHCl$_3$ saturated with ammonia) to give 1-19 as a yellow oil.

$R_f$ (10% CH$_3$OH/CHCl$_3$ saturated with ammonia) 0.47.

$^1$H NMR (400 MHz, CDCl$_3$) δ8.58 (s, 1H), 8.48 (d, 1H), 7.95 (d, 1H), 7.65 (d, 1H), 7.23 (dd, 1H), 6.48 (d, 1H), 6.34 (s, 1H), 5.45 (t, 1H), 4.05 (q, 2H), 3.53 (m, 1H), 3.4 (m, 1H), 3.1 (m, 2H), 2.86 (m, 2H), 2.65 (m, 3H), 2.55 (m, 2H), 1.9 (m, 1H), 1.76 (m, 1H), 1.7 (m, 1H), 1.55 (m, 1H), 1.17 (t, 2H).

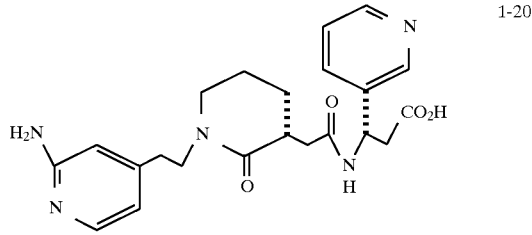

[3(R)-[1-(2-(2-Aminopyridin-4-yl)ethyl)-2-piperidon-3-yl]acetamido]-3-(3(S)-(pyridin-3-yl)) propanoic acid (1-20)

A solution of 1-19 (0.378 g, 0.768 mmol) in dioxane (5 mL) was treated with 1N NaOH (2 mL, 2 mmol) for 20 minutes. The solution was concentrated and chromatographed (silica gel, 9:1:1 EtOH/H$_2$O/NH$_4$OH) to give 1-20 as a white solid.

$R_f$ (9:1:1 EtOH/H$_2$O/NH$_4$OH) 0.61.

$^1$H NMR (400 MHz, D$_2$O) δ8.4 (s, 1H), 8.3 (d, 1H), 7.75 (d, 1H), 7.62 (d, 1H), 7.45 (m, 1H), 6.65 (m, 2H), 5.1 (t, 1H), 3.48 (t, 2H), 3.15 (m, 2H), 2.72 (t, 2H), 2.6 (m, 2H), 2.52 (m, 2H), 2.45 (m, 1H), 1.7–1.5 (m, 3H), 1.4 (m, 1H).

SCHEME 2

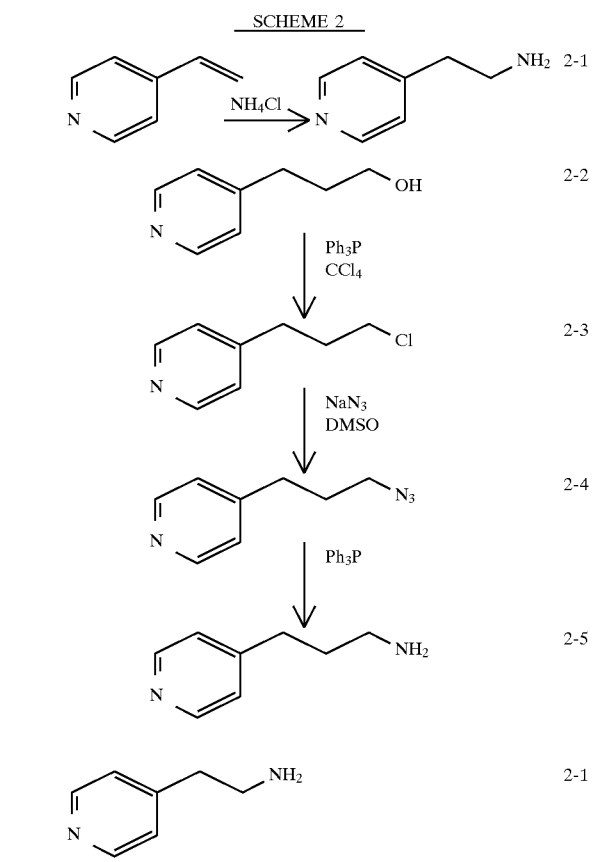

4-Pyridyl-2-ethylamine (2-1)

A slurry of vinyl pyridine (161.4 mL, 1.5 mol) and ammonium chloride (240.7 g, 4.5 mol) in 1:1 MeOH/H$_2$O (1.2 L) was heated to reflux for 18 h. The resulting homogenous solution was basified to pH13 with 3N NaOH and extracted repeatedly with $CH_2Cl_2$. The organic extracts were combined and concentrated to give a green oil, which was fractionally distilled to give 2-1 as an amber liquid.

$R_f$ (5% $MeOH/CHCl_3$ saturated with $NH_3$) 0.74.

$^1H$ NMR (400 MHz, $CDCl_3$) δ8.5 (d, 2H), 7.15 (d, 2H), 3.0 (t, 2H), 2.75 (t, 2H), 1.5 (bs, 2H).

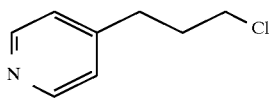

2-3

3-(4-Pyridyl) 1-chloropropane (2-3)

A solution of 3-pyridylpropanol (2-2) (ICN Biochemicals, 14.2 g, 0.1 mol) in THF (200 mL) was treated successively with triphenylphosphine (47.2 g, 0.18 mol) and carbontetrachloride (17.4 mL, 0.18 mol) and stirred for 24 h. The reaction was filtered and the solids washed with $Et_2O$. The filtrate was concentrated to give a yellow solid which was triturated with $Et_2O$. Chromatography (silica gel, 30% EtOAc/Hexanes) gave 2-3 as yellow oil.

$R_f$ (50% Acetone/Hexanes) 0.51.

$^1H$ NMR (400 MHz, $CDCl_3$) δ8.54 (d, 2H), 7.15 (d, 2H), 3.55 (t, 2H), 2.8 (t, 2H), 2.1 (m, 2H).

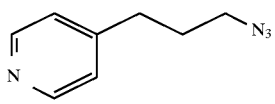

2-4

3-(4-Pyridyl)-1-propylazide (2-4)

A solution of 2-3 (7 g, 41.2 mmol) in DMSO (150 mL) was treated with sodium azide (2 g, 45.3 mmol) and heated to 65° C. for 72 h. The solution was diluted with EtOAc, washed with $H_2O$ and saturated $NaHCO_3$. The $H_2O$ washing was basified to pH11 and extracted with EtOAc. The organic layers were combined, dried with brine and $MgSO_4$, filtered and evaporated to give 2-4 as a yellow oil.

$^1H$ NMR (400 MHz, $CDCl_3$) δ8.5 (d, 2H), 7.15 (d, 2H), 3.3 (t, 2H), 2.7 (t, 2H), 1.92 (m, 2H).

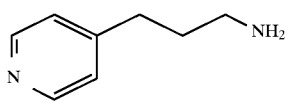

2-5

3-(4-Pyridyl)-1-propylamine (2-5)

A solution of 2-4 (7.3 g, 41.2 mmol) in $H_2O$ (100 mL) and THF (200 mL) was treated with triphenylphosphine (43.3 g, 165 mmol) and the resulting slurry was stirred vigorously for 24 h. The solution was diluted with EtOAc and washed with 10% $KHSO_4$. The aqueous layers were combined and basified to pH13 with 1N NaOH and extracted repeatedly with $CH_2Cl_2$. The $CH_2Cl_2$ layers were combined, dried with brine and concentrated to give 2-5 as a yellow oil.

$^1H$ NMR (400 MHz, $CD_3OD$) δ8.4 (d, 2H), 7.3 (d, 2H), 2.65 (m, 4H), 1.8 (m, 2H).

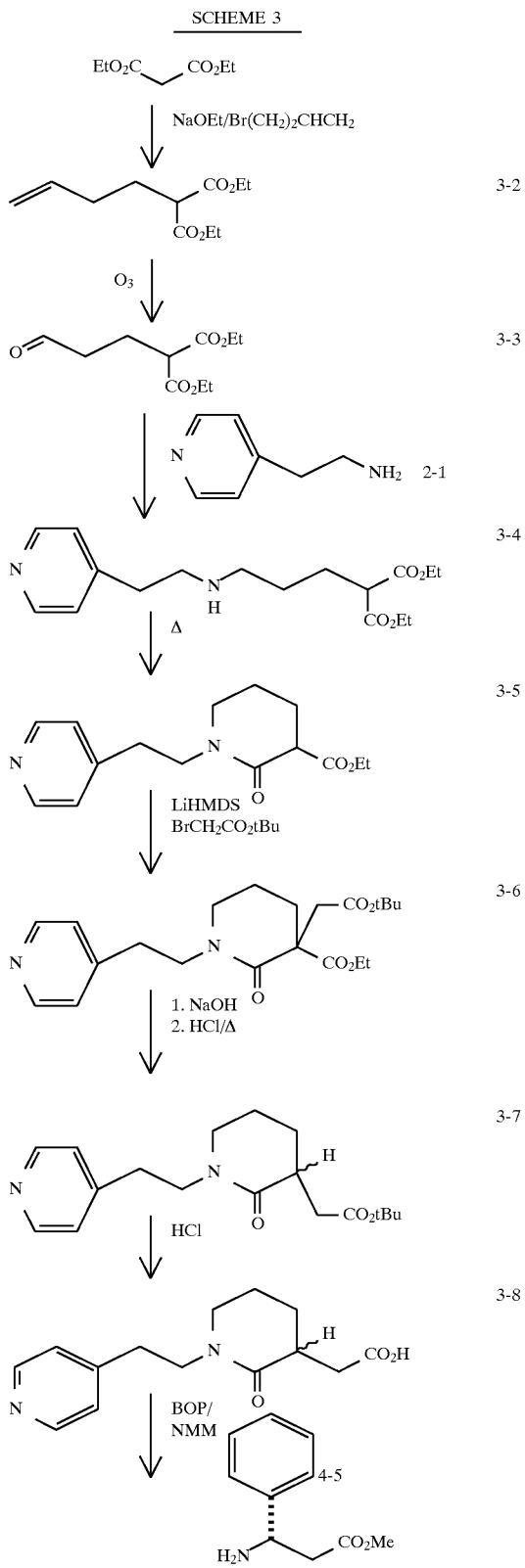

-continued
SCHEME 3

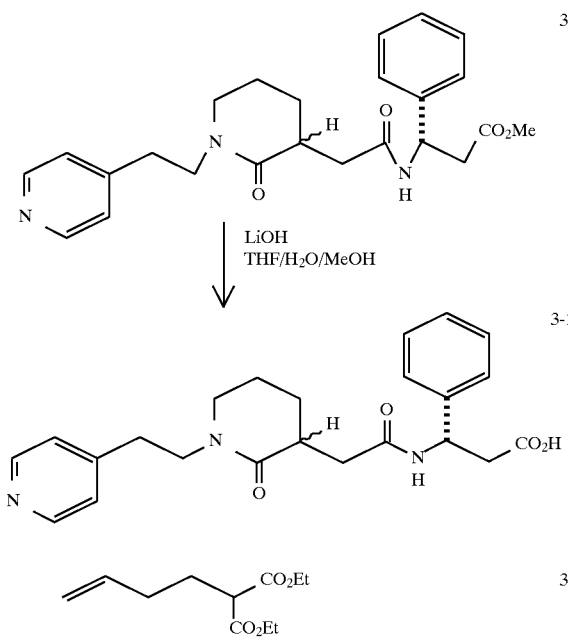

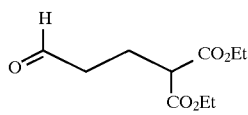

Diethyl 2-(3-butenyl)malonate (3-2)

A solution of NaOEt, prepared from the treatment of 1 L EtOH with sodium metal (19.5 g, 0.813 mol), was cooled to 0° C. and diethyl malonate (3-1, 100 g, 0.625 mol) was added dropwise over 0.5 h. After the addition was complete, the reaction was stirred for an additional 0.5 h, then a solution of 1-bromo-3-butene (76.1 mL, 0.75 mol) in 100 mL EtOH was added dropwise over forty-five minutes. The reaction was heated to reflux for 18 h, cooled and the solvent was removed in vacuo. The residue was dissolved in H$_2$O and washed with EtOAc. The organic layer was dried with brine and MgSO$_4$, filtered and evaporated. Fractional distillation of the residue (0.25–0.4 mm Hg, 70°–80° C.) gave 3-2 as a clear liquid.

R$_f$ (20% EtOAc/Hexanes) 0.73.

$^1$H NMR (400 MHz, CDCl$_3$) δ5.8 (m, 1H), 5.0 (2d, 2H), 4.2 (2q, 4H), 3.36 (t, 1H), 2.1 (m, 2H), 2.0 (m, 2H), 1.25 (2t, 6H).

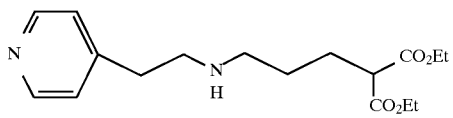

Diethyl 2-(3-propanal)malonate (3-3)

A solution of 3-2 (20 g, 93.4 mmol) in 1:1 CHCl$_3$/MeOH (500 mL) was cooled to −78° C. under argon and ozone was bubbled through the solution until it turned blue. The solution was purged with argon until it became colorless, then treated with dimethylsulfide (137 mL) and warmed. After stirring for 2 h at room temperature the solvent was removed in vacuo and the residue was diluted with 150 mL of EtOAc and washed with H$_2$O, brine, dried over MgSO$_4$, filtered and evaporated to give 3-3 as a clear oil.

R$_f$ (20% EtOAc/Hexanes) 0.31.

$^1$H NMR (400 MHz, CDCl$_3$) δ9.9 (s, 1H), 4.2 (2q, 4H), 3.4 (t, 1H), 2.6 (t, 2H), 2.2 (q, 2H), 1.3 (2t, 6H).

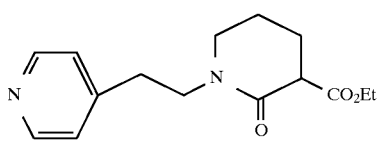

Diethyl 2-(3-(4-aminoethylpyridine)propyl)malonate (3-4)

To a solution of 3-3 (20 g, 93.4 mmol) in CH$_3$OH (600 mL) was added finely chopped aluminum foil (12.6 g, 0.47 mol), 2-1 (12 g, 98 mmol), and HgCl$_2$ (0.1 g, catalytic). After 15 minutes a grey percipitate formed. After stirring for 18 h the grey suspension was filtered through Solka Floc and the filter cake was rinsed with 1 L of MeOH. The solvent was evaporated to give 3-4 as an amber oil.

R$_f$ (4% MeOH/CHCl$_3$ saturated with NH$_3$) 0.34.

$^1$H NMR (400 MHz, CDCl$_3$) δ8.5 (d, 2H), 7.13 (d, 2H), 4.2 (2q, 4H), 3.32 (t, 1H), 2.9 (m, 2H), 2.8 (m, 2H), 2.65 (t, 2H), 1.9 (m, 2H), 1.5 (m, 2H), 1.26 (2t, 6H).

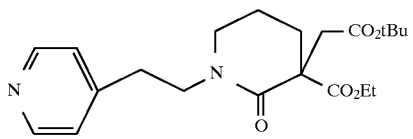

3(R,S)-[1-(2-(Pyridin-4-yl)ethyl)-2-piperidon-3-yl] formic acid ethyl ester (3-5)

Neat 3-4 was heated to 100° C. for 6 h under vacuum. The dark brown residue was chromatographed (silica gel, 10–20% CH$_3$OH/EtOAc) to give 3-5.

R$_f$ (4% MeOH/CHCl$_3$ saturated with NH$_3$) 0.44

$^1$H NMR (400 MHz, CDCl$_3$) δ8.5 (d, 2H), 7.18 (d, 2H), 4.2 (m, 2H), 3.68 (m, 1H), 3.5 (m, 1H), 3.4 (t, 1H), 3.14 (m, 2H), 2.9 (m, 2H), 2.05 (m, 2H), 1.9 (m, 1H), 1.7 (m, 1H), 1.3 (t, 3H).

3(R,S)-(Ethyl formyl)-[1-(2-(pyridin-4-yl)ethyl)-2-piperidon-3-yl]acetic acid t-butyl ester (3-6)

A solution of 3-5 (5.5 g, 20 mmol) in THF (100 mL) was cooled to 0° C. LiN(TMS)$_2$ (1N solution in hexanes, 22 mL, 22 mmol) was added dropwise and the solution was stirred for 0.5 h, then treated with t-butyl bromoacetate (2.9 mL, 20 mmol) and stirred for 1 h. The reaction was diluted with EtOAc and H$_2$O, the layers were separated, and the aqueous layer was extracted with EtOAc. The organic layers were combined, dried with brine and MgSO$_4$, filtered and evaporated and the residue was chromatographed (silica gel, 10% MeOH/EtOAc) to give 3-6 as a yellow oil.

R$_f$ (10% MeOH/EtOAc) 0.32.

$^1$H NMR (400 MHz, CDCl$_3$) δ8.5 (d, 2H), 7.2 (d, 2H), 4.2 (m, 2H), 3.7 (m, 1H), 3.45 (m, 1H), 3.35 (m, 1H), 3.15 (m, 2H), 2.9 (m, 2H), 2.7 (d, 1H), 2.1 (m, 2H), 1.95 (m, 1H), 1.7 (m, 1H), 1.4 (s, 9H), 1.23 (t, 3H).

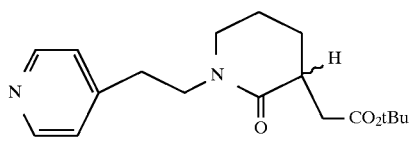

3-7

3(R,S)-[1-(2-(Pyridin-4-yl)ethyl)-2-piperidon-3-yl] acetic acid t-butyl ester (3-7)

A solution of 3-6 (5.6 g, 15.6 mmol) in EtOH (150 mL) was treated with 1N NaOH (156 mL, 156 mmol) and heated to 60° C. After 1 h the reaction is acidified with 1N HCl (156 mL, 156 mmol) to pH 5.5 and the reaction was heated to 100° C. for 48 h. The reaction was concentrated to yield a white solid which was suspended in CH$_3$CN, then filtered. The solid was rinsed with CH$_3$CN and the filtrate was concentrated to give a tan oil, which was a mixture of 3-7 and 3-8.

R$_f$ 3-7 (97:13:1 CHCl$_3$/MeOH/HOAc) 0.82.

R$_f$ 3-8 (97:13:1 CHCl$_3$/MeOH/HOAc) 0.14.

$^1$H NMR for 3-7 (400 MHz, CD$_3$OD) δ 8.5 (d, 2H), 7.5 (d, 2H), 3.6 (m, 2H), 3.3 (m, 2H), 3.0 (m, 4H), 2.6 (m, 3H), 2.15 (m, 1H), 1.95 (m, 1H), 1.8 (m, 1H), 1.65 (m, 1H), 1.45 (s, 9H).

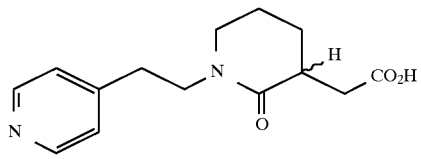

3-8

3(R,S)-[1-(2-(Pyridin-4-yl)ethyl)-2-piperidon-3-yl] acetic acid (3-8)

A solution of the mixture of 3-7 and 3-8 (4.5 g) in EtOAc (100 mL) was cooled to −78° C. and saturated with HCl gas. The reaction was warmed to 0° C. for 0.5 h, then concentrated to give a tan solid that was chromatographed (silica gel, 10:0.5:0.5 EtOH/NH$_4$OH/H$_2$O) to give 3-8 as a tan solid.

R$_f$ (97:13:1 CHCl$_3$/MeOH/HOAc) 0.14

$^1$H NMR (400 MHz, CD$_3$OD) δ 8.42 (d, 2H), 7.38 (d, 2H), 3.6 (m, 2H), 3.3 (m, 2H), 2.95 (t, 2H), 2.65 (m, 2H), 2.45 (m, 1H), 1.98 (m, 1H), 1.85 (m, 1H), 1.75 (m, 1H), 1.65 (m, 1H).

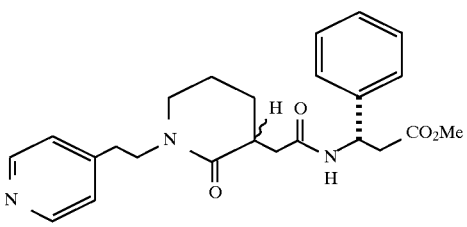

3-9

[3(R,S)-[1-(2-(Pyridin-4-yl)ethyl)-2-piperidon-3-yl] acetamido]-3-(3(S)-phenyl)propanoic acid methyl ester (3-9)

A solution of 3-8 (0.6 g, 2.3 mmol) in CH$_3$CN (10 mL) was treated with 4-5 (0.495 g, 2.3 mmol), BOP reagent (1.0 g, 2.3 mmol), and NMM (0.51 mL, 4.6 mmol). After stirring for 18 h the reaction was diluted with EtOAc and washed with H$_2$O, saturated NaHCO$_3$ and brine, dried (MgSO$_4$) filtered and evaporated. Column chromatography (silica gel, 10% MeOH/EtOAc) gave 3-9 as a white solid. The mixture of diastereomers was characterized:

R$_f$ (10% MeOH/EtOAc) 0.27

$^1$H NMR (400 MHz, CD$_3$OD) δ 8.5 (d, 4H), 7.25–7.15 (m, 10H), 7.1 (2d, 4H)g, 5.4 (m, 2H), 4.65 (m, 1H), 3.45 (m, 1H), 3.4 (m, 1H), 3.25 (m, 1H), 3.15 (m, 3H), 2.9–2.85 (m, 12H), 2.65 (m, buried), 1.95 (m, 4H), 1.8 (m, 4H), 1.7 (m, 4H), 1.6 (m, 6H).

3-10

[3(R,S)-[1-(2-(Pyridin-4-yl)ethyl)-2-piperidon-3-yl] acetamido]-3-(3(S)-phenyl)propanoic acid (3-10)

A solution of 3-9 (0.6 g, 1.4 mmol) in 1:1:1 THF/MeOH/H$_2$O (4 ml/4 mL/4 mL) was treated with LiOH (0.388 mg, 0.25 mmol). After 1 h, the reaction was concentrated. Chromatography (silica gel, 10/0.5/0.5 EtOH/NH$_4$OH/H$_2$O) gave 3-10 as a mixture of diastereomers.

R$_f$ (10/1/1 EtOH/NH$_4$OH/H$_2$O) 0.46

$^1$H NMR (400 MHz, CD$_3$OD) δ 8.4 (d, 4H), 7.3–7.15 (m, 14H), 5.3 (m, 2H), 3.6 (m, 4H), 3.25 (buried), 2.9 (m, 4H), 2.65 (m, 8H), 2.4 (m, 4H), 1.9 (m, 2H), 1.8 (m, 2H), 1.7 (m, 2H), 1.5 (m, 2H).

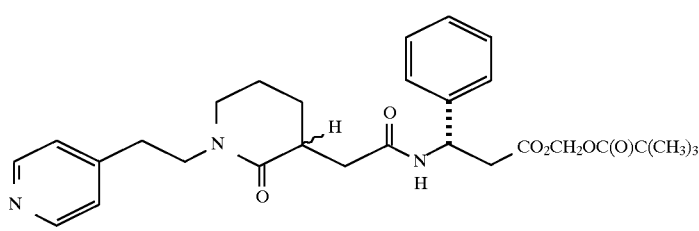

3-11

[3(R,S)-[1-(2-(Pyridin-4-yl)ethyl)-2-piperidon-3-yl]acetamido]-3-(3(S)-phenyl)propanoic acid pivaloyloxymethyl ester (3-11)

A solution of 3-10 (1.0 g, 2.4 mmol) in DMF (10 mL) was treated with CsCO₃ (0.78 g, 2.4 mmol) and chloromethylpivalate (Aldrich, 0.32 mL, 2.4 mmol). After 18 h the green solution was diluted with H₂O and EtOAc. The layers were separated and the aqueous layer was washed with EtOAc. The organic layers were combined, washed with brine, dried over MgSO₄, filtered and evaporated. Chromatography of the residue (silica gel, 100% EtOAc 5% MeOH/EtOAc gradient) gave 3-11 as a sticky solid. The mixture of diastereomers was characterized:

$R_f$ (5% MeOH/EtOAc) 0.29.

¹H NMR (400 MHz, CD₃OD) δ8.4 (d, 4H), 7.4–7.2 (m, 14H), 5.7 (m, 4H), 5.38 (m, 2H), 3.6 (m, 4H), 3.3 (buried) 2.9 (m, 8H), 2.65 (m, 4H), 2.4 (m, 2H), 1.9–1.8 (m), 1.75 (m), 1.5 (m), 1.18 (s, 18H).

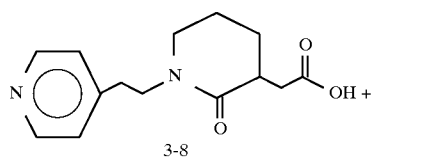

3-8

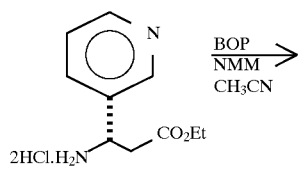

17-4

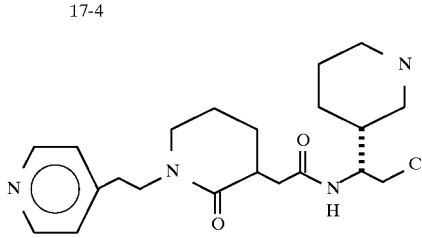

3-12

| 1 N NaOH
MeOH/THF

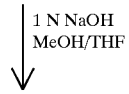

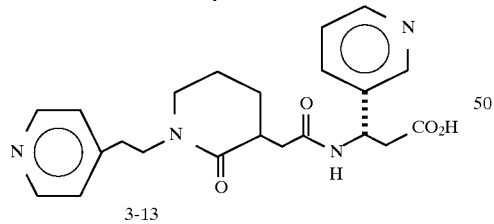

3-13

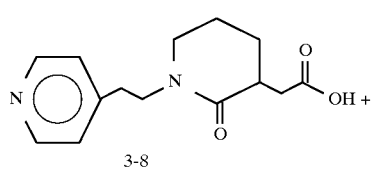

3-8

-continued

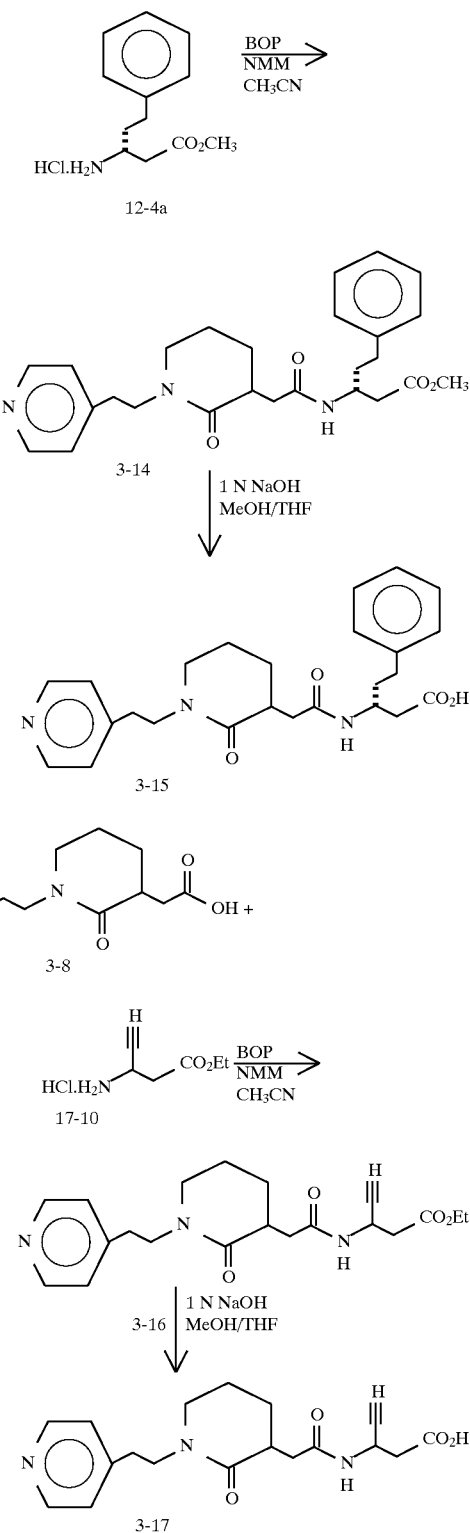

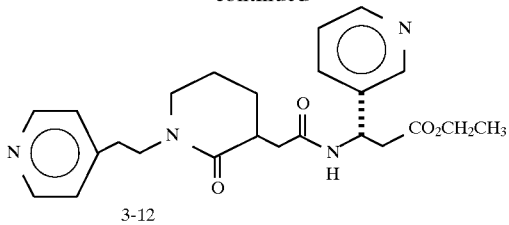

3-12

N-[1-[2-(4-Pyridyl)ethyl]-2-piperidone-3-yl]acetyl-3 (S)-(3-pyridyl)-β-alanine ethyl ester (3-12)

To a stirred solution of 3-8 (300 mg, 1.15 mmol), 17-4 (1.0 eq, 306 mmol), N-methyl morpholine (3.0 eq, 0.38, mL) in $CH_3CN$ (6 mL) was added BOP reagent (1 eq, 508 mg). The mixture was stirred for 20 hours at room temperature. $CH_3CN$ was removed in vacuo, and the crude product was purified by column chromatography ($SiO_2$, 5% MeOH in $CH_2Cl_2$). 350 mg of 3-12 was collected as a solid.

TLC: $R_f$=0.35 (silica, 10% MeOH in $CH_2Cl_2$).

$^1$H NMR ($CDCl_3$) δ1.18 (3H, t), 1.51–1.67 (1H, m), 1.67–1.87 (2H, m), 1.89–2.02 (1H, m), 2.55–2.66 (2H, m), 2.76–2.89 (4H, m), 3.08–3.21 (2H, m), 3.41–3.62 (2H, m), 4.02–4.12 (2H, q), 5.39–5.49 (1H, m), 7.18 (1H, t), 7.24–7.39 (2H, m), 7.60–7.70 (2H, m), 7.86 (1H, d), 8.48 (2H, m), 8.55–8.61 (1H, m).

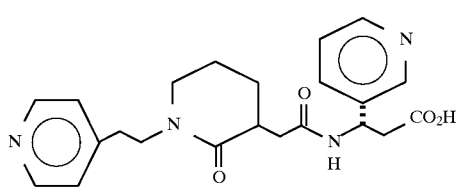

3-13

N-[1-[2-(4-Pyridyl)ethyl]-2-piperidone-3-yl]acetyl-3 (S)-3-pyridyl)-β-alanine (3-13)

To a stirred solution of 3-12 (350 mg, 0.80 mmol) in MeOH/THF (1:3, 4 mL) was added 1N NaOH (3.0 eq, 2.4 mL). The reaction mixture was stirred at room temperature for 65 hours. Solvent was removed in vacuo, and the crude product was purified by reverse phase HPLC [Delta-Pak C-18 column, $CH_3CN/H_2O$ with 0.1% TFA gradient). 135 mg of 3-13 was collected as the trifluoroacetate salt.

TLC: $R_f$=0.37 (silica, 10:0.5:0.5 EtOH:$NH_4OH$:$H_2O$)

$^1$H NMR ($CD_3OD$) δ1.48–1.69 (1H, m), 1.69–1.98 (3H, m), 2.38–2.50 (1H, m), 2.51–2.71 (2H, m), 2.91–2.99 (2H, m), 3.08–3.21 (2H, m), 3.30–3.42 (2H, m), 3.58–3.83 (2H, m), 5.37–5.43 (1H, m), 7.82–7.97 (1H, m), 7.98 (2H, d), 8.38–8.50 (1H, m), 8.63–8.75 (3H, m), 8.84 (1H, d).

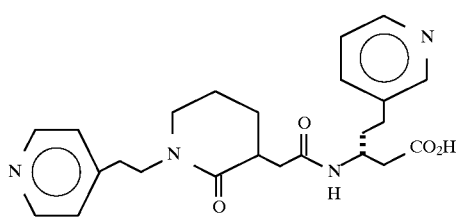

3-15A

N-[1-2-(4-Pyridyl)ethyl]-2-piperidone-3-yl]acetyl-3 (R)-(2-phenethyl)-β-alanine, DIASTEREOMER A (3-15A)

[1(2-(4-Pyridyl)ethyl]-2-piperidone-3-yl]acetic acid 3-8 and 3(R,S)-(4-phenethyl)-β-alanine methyl ester hydrochloride 12-4a were coupled using standard peptide procedures (BOP). The methyl ester product was hydrolyzed and purified using the procedure of 3-13 to give the title compound as the trifluoroacetate salt.

TLC: $R_f$=0.55 (silica, 10:0.5:0.5 $EtOH.NH_4OH.H_2O$)

Anal. Calcd. for $C_{25}H_{31}N_3O_4$.2.45 TFA C, 50.10; H, 4.70; N, 5.86 found: C, 50.07; H, 4.74; N, 5.46

FAB MS m/z=438 (m+1)

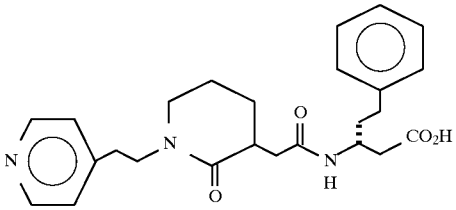

3-15B

N-[1-[2-(4-Pyridyl)ethyl]-2-piperidone-3-yl]acetyl-3 (R)-(2-phenethyl)-β-alanine DIASTEREOMER B (3-15B)

[1[2-(4-pyridyl)ethyl]-2-piperidone-3-yl]acetic acid 3-8 and 3(R,S)-(4-phenethyl)-β-alanine methyl ester hydrochloride 12-4a were coupled using standard peptide procedures (BOP). The methyl ester product was hydrolyzed and purified using the procedure of 3-13 to give the title compound as the trifluoroacetic salt.

TLC: $R_f$=0.55 (silica, 10:0.5:0.5 $EtOH.NH_4OH.H_2O$)

$^1$H NMR ($CD_3OD$) δ1.54–1.69 (1H, m), 1.72–1.98 (5H, m), 2.34–2.45 (1H, m), 2.47 (2H, m), 2.57–2.74 (4H, m), 3.18 (2H, t), 3.35–3.43 (2H, m), 3.62–3.84 (2H, m), 4.16–4.27 (1H, m), 7.12–7.28 (5H, m), 7.99 (2H, d), 8.68 (2H, d).

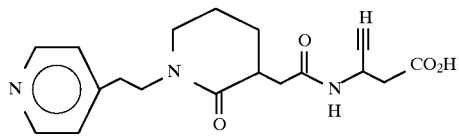

3-17A

N-[1-[2-(4-Pyridyl)ethyl]-2-piperidone-3-yl]acetyl-3-ethynyl-β-alanine DIASTEREOMERS A (3-17A)

[1-[2-(4-pyridyl)ethyl]-2-piperidone-3-yl]acetic acid 3-8 and 3-ethynyl-β-alanine ethyl ester hydrochloride (7-10) were coupled using standard peptide procedures (BOP). The ethyl ester product was hydrolyzed and purified using the procedure of 3-13 to give the title compound as the trifluoroacetate salt 3-17A.

TLC: $R_f$=0.59 (silica, 10:0.5:0.5 $EtOH.NH_4OH.H_2O$)

Anal. calcd. for $C_9H_{23}N_3O_4$.0.85 $H_2O$.1.95 TFA C, 46.22; H, 4.51; N, 7.06 found: C, 46.22; H, 4.50; N, 7.46

FAB MS m/z=358 (m+1)

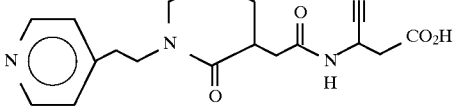

3-17B

N-[1-[2-(4-Pyridyl)ethyl]-2-piperidone-3-yl]acetyl-3-ethynyl-β-alanine DIASTEREOMERS B (3-17B)

[1-[2-(4-pyridyl)ethyl]-2-piperidone-3-yl]acetic acid and 3-ethynyl-β-alanine ethyl ester hydrochloride were coupled using standard peptide procedures (BOP). The ethyl ester product was hydrolyzed and purified to give the title compound as the trifluoroacetate salt 3-17B.

TLC: $R_f$=0.59 (SiO$_2$, 10:0.5:0.5 EtOH.NH$_4$OH.H$_2$O)

$^1$H NMR (CD$_3$OD) δ1.53–1.69 (1H, m), 1.72–1.84 (1H, m), 1.84–1.95 (2H, m), 2.37–2.49 (1H, m), 2.52 (1H, d), 2.55–2.64 (1H, m), 2.64–2.74 (3H, m), 3.19 (2H, t), 3.33–3.43 (2H, m), 3.63–3.84 (2H, m), 4.94–5.04 (1H, m), 7.97 (2H, d), 8.71 (2H, d).

SCHEME 4

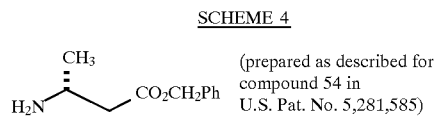

(prepared as described for compound 54 in U.S. Pat. No. 5,281,585)

re-adjust the pH of the solution to 10. After 18 h the pH of the solution was adjusted once again to 10 with 1N NaOH and an additional 3.9 g of di-t-butyldicarbonate was added. After 1 h the solution was diluted with EtOAc and the layers were separated. The aqueous layer is acidified with 10% KHSO$_4$ to pH4 and extracted with EtOAc. The EtOAc layers were combined, dried with brine and MgSO$_4$, filtered and evaporated to give 4-3 as a hygroscopic white solid.

$R_f$ (97:3:1 CHCl$_3$/MeOH/HOAc) 0.28

$^1$H NMR (400 MHz, CDCl$_3$) δ8.05 (bs, 1H), 7.4–7.3 (m, 5H), 5.1 (d, 1H), 1.1 (s, 9H).

Methyl 3-(S)-N-t-butyloxycarbonylamino-3-phenylpropionate (4-4)

A solution of 4-3 (3.0 g, 1.2 mmol) in EtOAc (60 mL) was cooled to −15° C. and treated with NMM (1.32 mL, 12 mmol) and isobutylchloroformate (1.56 mL, 12 mmol). A white percipitate formed. The reaction was treated with a solution of diazomethane until a homogenous yellow solution resulted. The reaction was warmed to room temperature for 20 minutes, purged with argon and concentrated. The residue was dissolved with MeOH (65 mL) and treated with a solution of silver acetate in triethylamine (0.904 g in 5 mL). The reaction was concentrated and the residue chromatographed (10% EtOAc/Hexanes) to give 4-4 as an oil.

$R_f$ (30% EtOAc/Hexanes) 0.68.

$^1$H NMR (400 MHz, CDCl$_3$) δ7.25 (m, 5H), 5.4 (bs, 1H), 5.1 (bs, 1H), 3.6 (s, 3H), 2.85 (m, 2H), 1.4 (s, 9H).

Methyl 3-(S)-amino-3-phenylpropionate hydrochloride (4-5)

A solution of 4-4 (0.7 g, 2.5 mmol) in EtOAc (10 mL) was cooled to −78° C. and saturated with HCl gas. The solution was warmed to 0° C. for 0.5 h, then concentrated in vacuo to give 4-5 as a yellow solid.

$R_f$ (10% MeOH/CHCl$_3$ saturated with NH$_3$) 0.41.

$^1$H NMR (400 MHz, CD$_3$OD) δ7.42 (s, 5H), 4.75 (t, 1H), 3.7 (s, 3H), 3.1 (m, 2H).

(R)-N-t-Butyloxycarbonyl phenylglycine (4-3)

A slurry of (R)-phenylglycine (5 g, 33 mmol) in dioxane (30 mL), H$_2$O (15 mL), and 1N NaOH (15 mL) was cooled to 0° C. and treated with di-t-butyldicarbonate (7.9 g, 36.3 mmol). The reaction was warmed to room temperature and after 0.5 h additional 1N NaOH (7.5 mL) was added to

SCHEME 5

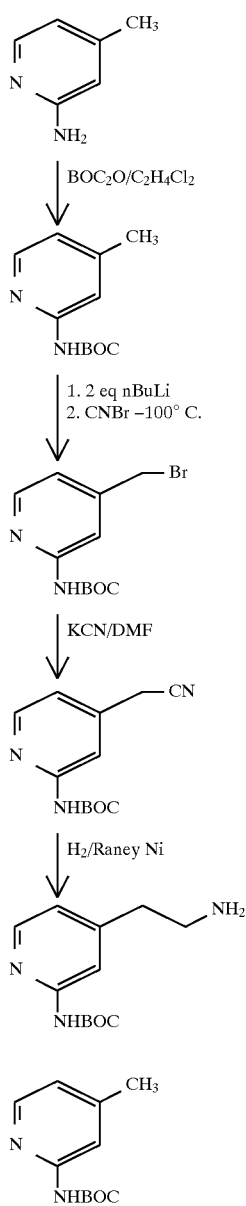

2-N-BOC-amino-4-picoline (5-2)

A solution of 2-amino-4-picoline 5-1 (Aldrich, 20 g, 0.195 mol) in dichloroethane (250 mL) was added dropwise over 3 h to a refluxing solution of di-t-butyldicarbonate (44 g, 0.2 mol) in dichloroethane (100 mL). The reaction was refluxed for an additional 2 h after the addition was completed, then cooled to room temperature and stirred for 18 h. The resolution solution was evaporated and the residue was absorbed to silica gel using $CHCl_3$ and MeOH and added to the top of a pad of silica gel. The column was flushed with 1 L of Hexanes and the compound was then eluted with 10% EtOAc/Hexanes to give 5-2 as a white solid.

$R_f$ (10% EtOAc/Hexanes) 0.3.

$^1H$ NMR (400 MHz, $CDCl_3$) δ10.05 (s, 1H), 8.23 (d, 1H), 7.88 (s, 1H), 6.78 (d, 1H), 2.34 (s, 3H), 1.54 (s, 9H).

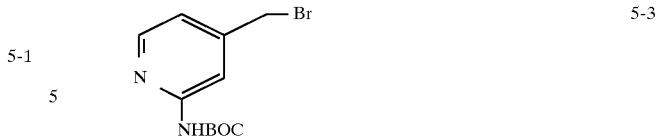

2-N-Boc-Amino-4-bromomethyl pyridine (5-3)

A solution of 5-2 (12 g, 57.6 mmol) in THF (100 mL) was cooled to −78° C. and treated with n-butyllithium (2.1M in hexanes, 55 mL, 115 mmol) to give a yellow solution. The solution was warmed to 0° C. for 0.5 h to give a yellow suspension which was re-cooled to −78° C. and transferred via a wide-bore cannulla to a jacketed dropping funnel that had been pre-cooled to −78° C. The suspension was added dropwise to a rapidly stirred solution of Cyanogenbromide (49 g, 460 mmol) in THF (300 mL) that had been cooled to −100° C. The resulting yellow-orange solution was stirred for 0.5 h, then poured into 300 mL of $H_2O$ and extracted with EtOAc (300 mL). The layers were separated and the aqueous layer was extracted twice more with EtOAc. The organic layers were combined and washed with 2×30 mL 10% $KHSO_4$ and brine and evaporated. The residue was absorbed to silica gel with $CHCl_3$ and MeOH and chromatographed with a gradient of 10–40% EtOAc/Hexanes to give 5-3 as a white solid.

$R_f$ (20% EtOAc/Hexanes) 0.43.

$^1H$ NMR (400 MHz, $CDCl_3$) δ8.4 (d, 1H), 7.97 (s, 1H), 7.48 (s, 1H), 6.98 (d, 1H), 4.36 (s, 2H), 1.51 (s, 9H).

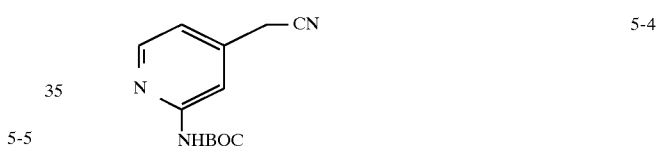

2-N-Boc Amino-4-cyanomethyl pyridine (5-4)

A solution of 5-3 (7.0 g, 24.6 mmol) in DMF (240 mL) was treated with a solution of potassium cyanide (16.2 g, 249 mmol) in $H_2O$ (60 mL) that was added all in one portion. The bright red solution was stirred for 0.5 h and the solvent removed under vacuum. The residue was partitioned between dilute $NaHCO_3$ and $CH_2Cl_2$ and the layers separated. The aqueous layer was washed with $CH_2Cl_2$, dried ($Na_2SO_4$), filtered and evaporated. The red residue was chromatographed (silica gel, 20–30% EtOAc/Hexanes) to give 5-4 as an off-white solid.

$R_f$ (30% EtOAc/Hexanes) 0.21.

$^1H$ NMR (400 MHz, $CDCl_3$) δ9.03 (s, 1H), 8.44 (d, 1H), 8.0 (s, 1H), 7.02 (d, 1H), 3.75 (s, 2H), 1.54 (s, 9H).

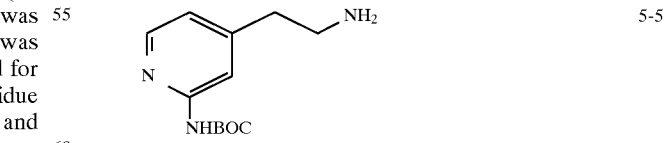

2-N-Boc Amino-4-(2-amino ethyl)pyridine (5-5)

A slurry of 5-4 (3.9 g, 16.7 mmol) in $CH_3OH$ (140 mL) and concentrated ammonium hydroxide (70 mL) was treated with Raney Nickel (50% in $H_2O$, 3 mL) and hydrogenated on a Parr apparatus at 60 psi. After 6 h the solution was purged with argon, filtered through Solka-Floc and concentrated to give a green oil. The oil was azeotroped with benzene and heptane, then chromatographed (silica gel, 2% CH₃OH/CHCl₃ saturated with ammonia) to give 5-5 as a bright yellow oil.

$R_f$ (20% CH₃OH/CHCl₃ saturated with ammonia) 0.67.
¹H NMR (400 MHz, CD₃OD) δ8.1 (d, 1H), 7.72 (s, 1H), 6.9 (d, 1H), 2.9 (m, 2H), 2.75 (m, 2H), 1.51 (s, 9H).

SCHEME 6

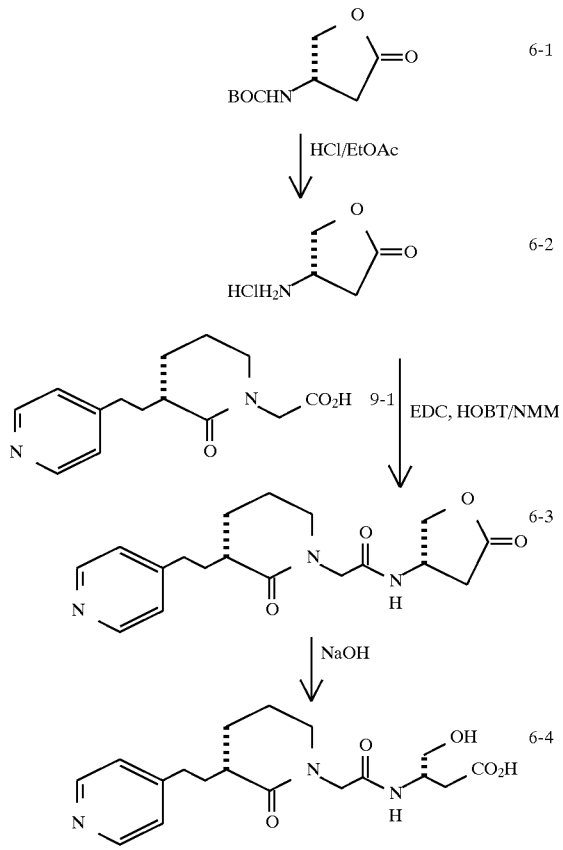

3-(S)-Amino-butyrolactone hydrochloride (6-2)

A solution of 6-1 (*J. Chem. Soc. Chem. Comm.* 1987, p 51, 0.92 g, 4.6 mmol) in EtOAc (15 mL) was cooled to −78° C. and saturated with HCl gas. The reaction was warmed to 0° C. for 1 h, then evaporated to give 6-2 as a white solid.

¹H NMR (400 MHz, DMSO) δ8.5 (bs, 2H), 4.45 (m, 2H), 4.3 (m, 2H), 4.15 (bs, 1H), 2.9 (dd, 1H), 2.5 (m, 1H).

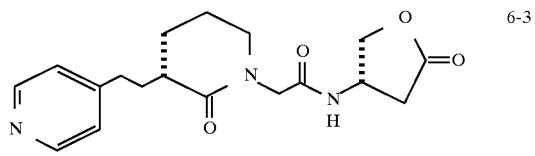

[[3(R)-(2-(Pyridin-4-yl)ethyl)-2-piperidon-1-yl] acetamido]-3(S)-butyrolactone (6-3)

A solution of 9-1 (1.25 g, 1.93 mmol) and 6-2 (0.264 g, 1.93 mmol) in DMF (10 mL) was treated with EDC (0.43 g, 2.25 mmol), HOBT (0.29 g, 2.1 mmol) and di-isopropylethylamine (1.0 mL, 5.7 mmol) for 18 h. The reaction was concentrated and the residue was chromatographed (silica gel, 10% HOAc/EtOAc to elute HOBT followed by EtOAc, then 97:10:1 CHCl₃/MeOH/HOAc). The impure product was purified by preparative HPLC (reverse phase, 95:5 0.1% TFA in H₂O/0.1% TFA in CH₃CN to 80–20 gradient) followed by column chromatography (25–35% isopropanol/CH₂Cl₂) to give 6-3 as a white solid.

¹H NMR (400 MHz, D₂O) δ8.55 (d, 2H), 7.4 (d, 2H), 4.5 (m, 2H), 4.18 (m, 1H), 3.84 (s, 2H), 3.3–3.15 (m, 2H), 2.9 (dd, 1H), 2.6 (m, 2H), 2.4 (dd, 1H), 2.26 (m, 1H), 1.9 (m, 1H), 1.9–1.5 (m, 5H).

[[3(R)-(2-(Pyridin-4-yl)ethyl)-2-piperidon-1-yl] acetamido]-3(S)-(4-hydroxy)butanoic acid (6-4)

A suspension of 6-3 (0.155 g, 0.337 mmol) in dioxane (2 mL) and 1N NaOH (2 mL) was stirred for 2 h, then treated with 1N HCl (2 mL) and evaporated. The residue was chromatographed (silica gel, 90:1:1 EtOH/H₂O/NH₄OH) to give 6-4 as a hygroscopic white solid.

¹H NMR (400 MHz, D₂O) δ8.42 (d, 2H), 7.66 (d, 2H), 4.1 (m, 1H), 3.94 (d, 1H), 3.85 (d, 1H), 3.48 (dd, 1H), 3.24 (m, 1H), 2.8 (t, 2H), 2.32 (m, 1H), 2.25 (m, 2H), 2.02 (m, 1H), 1.9–1.75 (m, 3H), 1.7 (m, 1H), 1.6 (m, 1H).

SCHEME 7

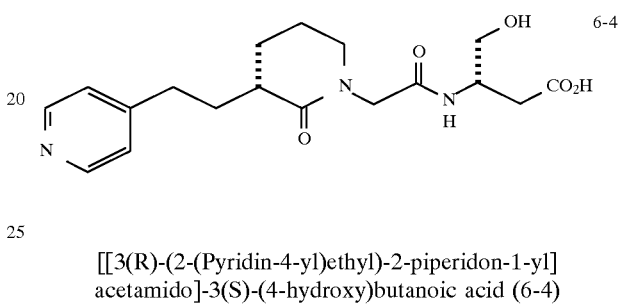

-continued
SCHEME 7

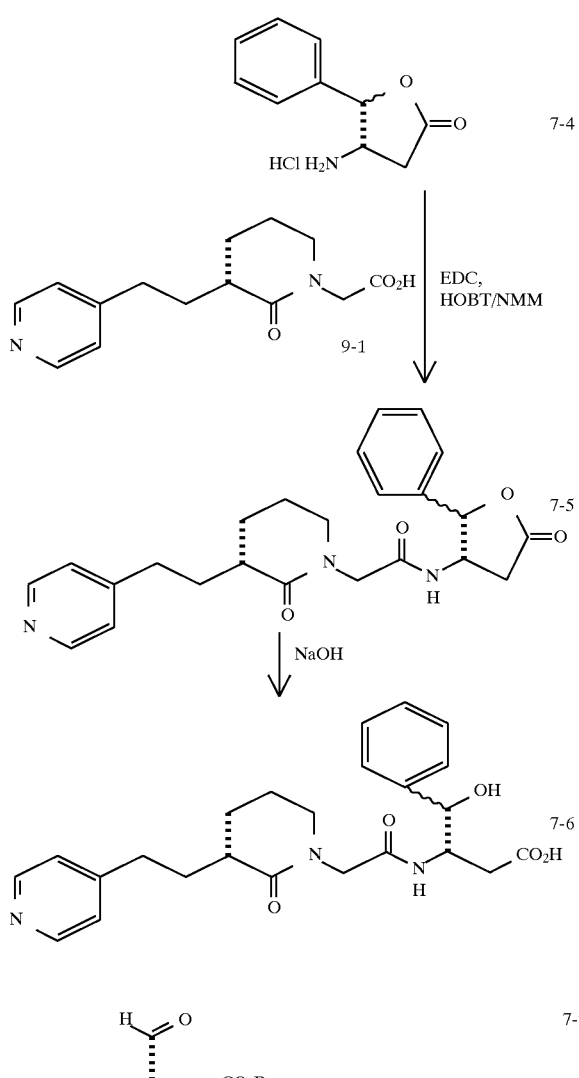

S-3-Benzylcarboxy-3-BOC-aminopropanal (7-2)

A solution of 7-1 (*Tet. Lett.* 1991, 32(7) 923, 7.07 g, 22.8 mmol) in CH$_2$Cl$_2$ (20 mL) was added dropwise to a −78° C. solution of oxalyl chloride (2.9 mL, 33 mmol) and DMSO (2.8 mL, 39.5 mmol) in CH$_2$Cl$_2$ (175 mL). After stirring for 15 minutes triethylamine (3.5 mL, 25 mmol) was added dropwise and the solution was allowed to warm to room temperature and diluted with H$_2$O and CH$_2$Cl$_2$. The layers were separated and the organic layer was washed with 10% KHSO$_4$ and brine, dried over Na$_2$SO$_4$, filtered and evaporated. The residue was chromatographed (silica gel, 30% EtOAc/Hexanes) to give 7-2 as a colorless oil.

R$_f$ (30% EtOAc/Hexanes) 0.33.

$^1$H NMR (400 MHz, CDCl$_3$) δ9.63 (s, 1H), 7.35 (m, 5H), 5.63 (bd, 1H), 5.12 (s, 2H), 4.36 (m, 1H), 3.02 (dd, 1H), 2.9 (dd, 1H), 1.45 (s, 9H).

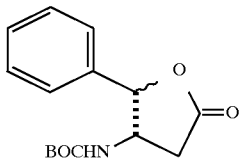

3-(S)-BOC-Amino-4-(R,S)-phenyl-butyrolactone (7-3)

A solution of 7-2 (2.96 g, 9.63 mmol) in THF (100 mL) was cooled to −20° C. and treated with phenyl lithium (3M in Et$_2$O, 3.9 mL, 12 mmol). The reaction was warmed to room temperature and stirred for 18 h, quenched with 10% HCl, diluted with H$_2$O, and neutralized in 1N NaOH. The solution was concentrated and extracted with EtOAc. The organic layer was dried with brine and Na$_2$SO$_4$, filtered and evaporated. The residue was chromatographed (silica gel, 15% EtOAc/Hexanes) to give crude product as a solid, which was triturated with hexanes to give 7-3 as a white solid contaminated with benzyl alcohol.

$^1$H NMR (400 MHz, CDCl$_3$) δ7.25 (m, 5H), 5.5 (bs, 1H), 4.95 (bs, 1H), 4.25 (bs, 1H), 2.9 (dd, 1H), 2.5 (dd, 1H), 1.45 (s, 9H).

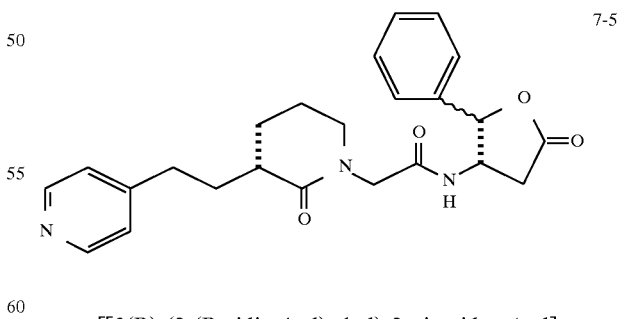

3-(S)-Amino-4-(R,S)-phenyl-butyralactone hydrochloride (7-4)

A solution of 7-3 (0.3 g, 1.1 mmol) in EtOAc (10 mL) was cooled to −78° C. and saturated with HCl gas, then warmed to 0° C. for 0.5 h and concentrated to give 7-4 as a white solid.

$^1$H NMR (400 MHz, DMSO) δ8.7 (bs, 2H), 7.4 (m, 5H), 5.67 (s, 1H), 4.02 (m, 1H), 3.23 (dd, 1H), 2.73 (dd, 1H).

[[3(R)-(2-(Pyridin-4-yl)ethyl)-2-piperidon-1-yl] acetamido]-3(S)-(4(R,S)-phenyl)butyrolactone (7-5)

Compound 7-4 was coupled to 8-1 as described for the formation of 6-3 to give 7-5 as a hygroscopic white solid.

R$_f$ (80% Acetone/Hexanes) 0.23.

55

$^1$H NMR (400 MHz, D$_2$O) δ8.3 (d, 2H), 7.43–7.3 (m, 5H), 7.23 (m, 2H), 5.39 (d, 1H), 4.58 (m, 1H), 3.9 (m, 2H), 1.3–1.15 (m, 2H), 3.05 (dd, 1H), 2.73 (dd, 1H), 2.63 (m, 2H), 2.3 (m, 1H), 2.0–1.5 (m, 6H).

56

[[3(R)-(2-(Pyridin-4-yl)ethyl)-2-piperidon-1-yl] acetamido]-3(S)-(4(R,S)-phenyl-4-hydroxy)butanoic acid (7-6)

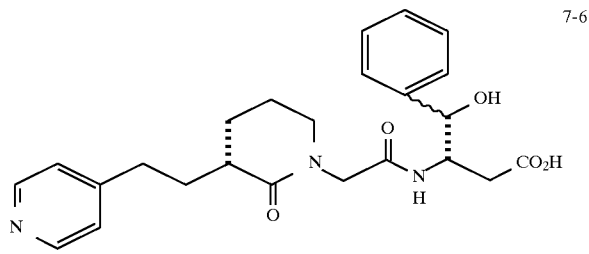

A solution of 7-5 (0.05 g, 0.12 mmol) in 1:1:1 THF/H$_2$O/MeOH was treated with LiOH (0.025 g, 0.6 mmol) for 0.5 h. The reaction was concentrated and the residue was chromatographed (silica gel, 9:1:1 EtOH/H$_2$O/NH$_4$OH) to give 7-6 as a white solid. R$_f$ (9:1:1 EtOH/H$_2$O/NH$_4$OH) 0.72.

$^1$H NMR (400 MHz, D$_2$O) δ8.4 (d, 2H), 7.55 (d, 2H), 7.2 (m, 5H), 4.56 (t, 1H), 4.3 (m, 1H), 3.8 (t, 1H), 3.6 (t, 1H), 2.9 (m, 1H), 2.73 (m, 2H), 2.45 (m, 1H), 2.26 (m, 2H), 1.98 (m, 1H), 1.83–1.7 (m, 3H), 1.53 (m, 2H).

SCHEME 8

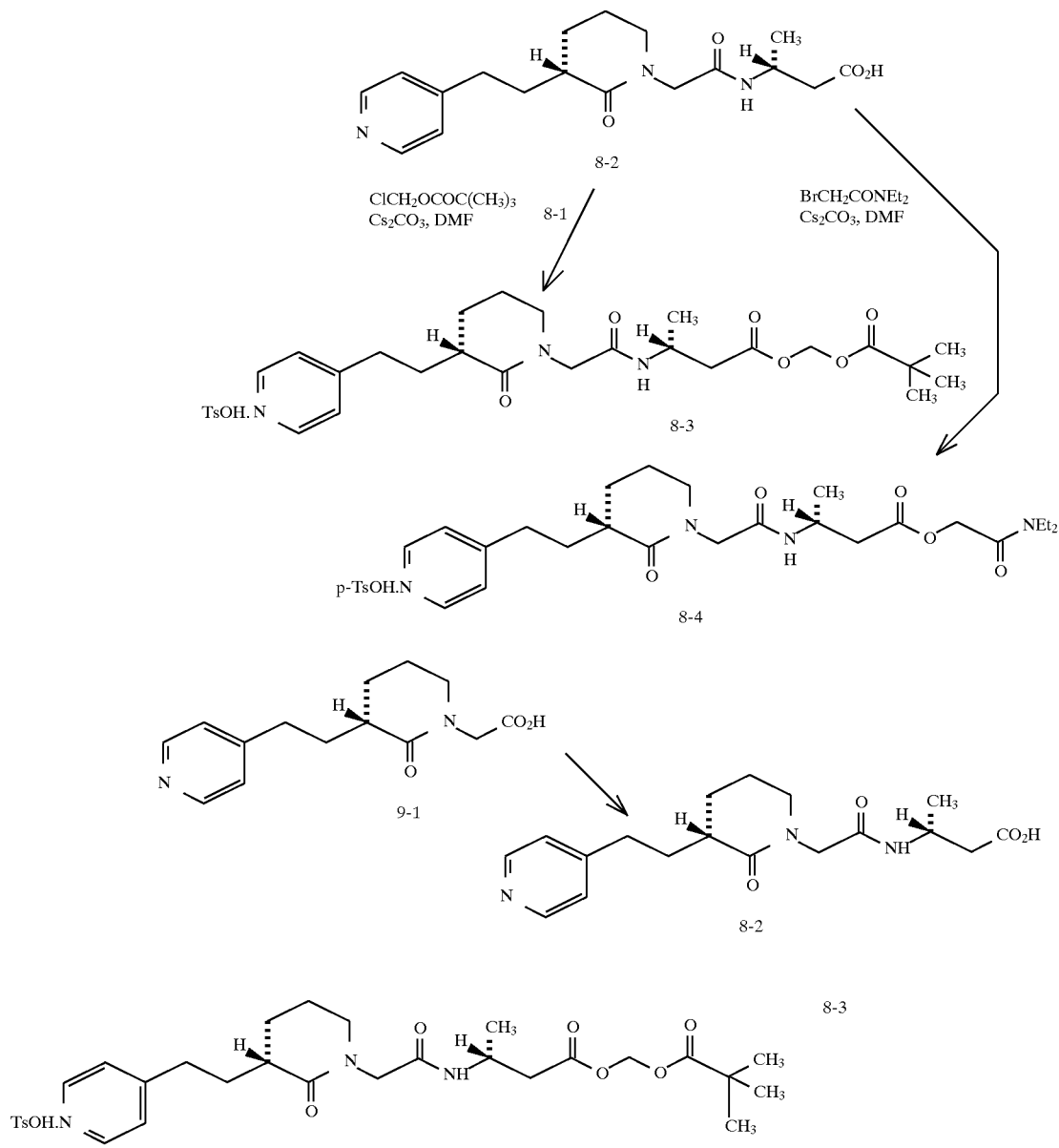

[3(R)-[2-(4-Pyridyl)ethyl]-2-piperidon-1-yl]acetyl-3 (R)-methyl-β-alanine pivaloyloxymethyl ester, p-toluenesulfonate salt (8-3)

3(R)-[2-(4-Pyridyl)ethyl]-2-piperidon-1-yl]acetyl-3(R)-methyl-β-alanine (8-2, 1.10 g, 3.17 mmol) was dissolved in 10 mL DMF, then Cs$_2$CO$_3$ (1.03 g, 3.17 mmol) and chloromethyl pivalate (0.41 mL, 3.8 mmol) were added. After stirring the suspension overnight additional chloromethyl pivalate (0.41 mL, 3.8 mmol) was added and the reaction continued 2 h longer. The mixture was diluted with water, extracted with EtOAc (2×), and the combined organic extracts were washed with water then brine, dried (MgSO$_4$), filtered and concentrated. Flash chromatography (alumina, EtOAc then 5% EtOH/EtOAc) provided an oil which was dissolved in Et$_2$O. TsOH was added until an acidic pH was achieved, the ether layer was decanted from the oily residue, the residue was rinsed with additional ether, then dried in vacuo providing the salt 8-3 as a white, hygroscopic solid.

$^1$H NMR (400 MHz, CDCl$_3$) δ8.76 (t, J=6 Hz, 2H), 8.0 (br s), 7.83 (d, J=6 Hz, 2H), 7.76 (d, J=8 Hz, 2H), 7.20 (d, J=8 Hz, 2H), 7.11 (br m, 1H), 5.72 (AB d, J=121 Hz, 1H), 5.71 (AB d, J=12 Hz, 1H), 4.31 (m, 1H), 4.14 (AB d, J=16 Hz, 1H), 4.04 (AB d, J=16 Hz, 1H), 3.46 (m, 2H), 3.10–2.96 (m, 2H), 2.65 (m, 1H), 2.55 (dd, J=6, 2 Hz, 2H), 2.37 (s, 3H), 2.25 (m, 1H), 2.17–1.85 (m), 1.72 (m, 1H), 1.20 (s, 9H).

rediluted with EtOAc, washed with water, sat. NaHCO$_3$, and brine, dried (MgSO$_4$), filtered and concentrated. After flash chromatography (silica, 10% MeOH/EtOAc) the resulting oil was dissolved in EtOAc, treated with 1.1 eq p-TsOH.H$_2$O, and concentrated, providing 8-4 as a hygroscopic white solid.

TLC R$_f$0.35 (silica, 20% MeOH/EtOAc).

$^1$H NMR (400 MHz, D$_2$O ) δ8.53 (d, J=7 Hz, 2H), 7.84 (d, J=7 Hz, 2H), 7.58 (d, J=8 Hz, 2H), 7.26 (d, J=8 Hz, 2H), 4.76 (s, 2H), 4.21 (hex, J=7 Hz, 1H), 3.94 (AB d, J=16 Hz, 1H), 3.85 (AB d, J=16 Hz, 1H), 3.35–3.20 (m), 2.91 (t, J=8 Hz, 2H), 2.60 (m, 2H), 2.39 (m, 1H), 2.29 (s, 3H), 2.08 (m, 1H), 2.00–1.55 (m), 1.13 (d, J=7 Hz, 3H), 1.09 (t, J=7 Hz, 3H), 1.00 (t, J=7 Hz, 3H).

N,N-diethylbromoacetamide was prepared as follows: Diethylamine (1.54 mL, 14.9 mmol) and TEA (2.49 mL, 17.9 mmol) were dissolved in 75 mL CH$_2$Cl$_2$, then bromoacetyl bromide (1.29 mL, 14.9 mmol) was added dropwise. After 2 h, the reaction was diluted with CH$_2$Cl$_2$, washed with water (2×), and brine, dried (MgSO$_4$), filtered and concentrated. Flash chromatography (silica, 45% EtOAc/hexanes) provided N,N-diethylbromoacetamide as a lachrymatory yellow oil.

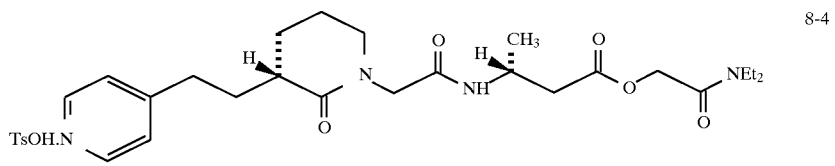

8-4

[3(R)-[2-(4-Pyridyl)ethyl]-2-piperidon-1-yl]acetyl-3 (R)-methyl-β-alanine diethylaminoglycolamide ester p-toluenesulfonate salt (8-4)

Acid 8-2 (2.0 g, 5.9 mmol) was dissolved in 30 mL DMF, then Cs$_2$CO$_3$ (959 mg, 2.95 mmol) and N,N-diethylbromoacetamide (1.25 g, 6.4 mmol) were added. After stirring overnight, the reaction was concentrated, TLC R$_f$0.30 (silica, 40% EtOAc/hexanes).

$^1$H NMR (300 MHz, CDCl$_3$) δ3.84 (s, 2H), 3.40 (q, J=7 Hz, 2H), 3.39 (q, J=7 Hz, 2H), 1.26 (t, J=7 Hz, 3H), 1.14 (t, J=7 Hz, 3H).

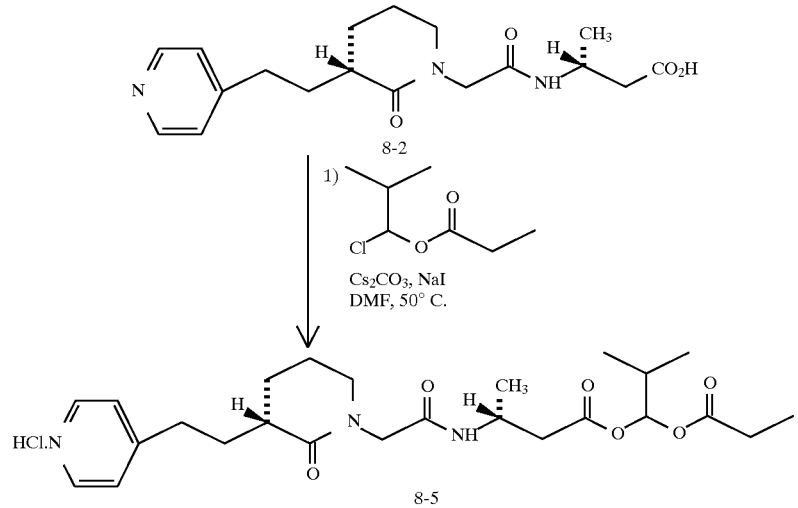

[3(R)-[2-(Pyridin-4-yl)ethyl]-2-piperidone-1-yl]-acetyl-3(R)-methyl-β-alanine isobutyryl propiolate hydrochloride (8-5)

Acid 8-2 (500 mg, 1.44 mmol), isobutyl chloroformate (355 mg, 2.16 mmole), Cs$_2$CO$_3$ (234 mg, 0.72 mmole), and NaI (5 mg, 0.03 mmole) were combined in 10 ml DMF. After heating at 50° C. for 16 hours, the reaction was diluted with EtOAc, washed with water, sat. NaHCO$_3$ and brine, dried, concentrated and purified by flash chromatography (silica, EtOAc→2% MeOH/EtOAc); concentrated, dissolved in 5 mL Et$_2$O, added 1 ml 1M HCl/Et$_2$O, concentrated, triturated with hexanes providing 8-5 as a white solid.

TLC R$_f$ 0.22 (silica, 2% MeOH/EtOAc)

$^1$H NMR (400 MHz, D$_2$O) 8.63 (d, J=7 Hz, 2H), 7.94 (d, J=7 Hz, 2H), 6.58 (q, J=5 Hz, 1H), 4.29 (m, 1H), 4.00 (m, 2H), 3.38 (m, 2H), 3.02 (t, J=8 Hz, 2H), 2.63 (m, 2H), 2.45 (m, 3H), 2.18 (m, 1H), 2.00 (m, 4H), 1.73 (m, 2H), 1.18 (d, J=7 Hz, 3H), 1.09 (t, J=8 Hz, 3H), 0.94 (m, 6H).

SCHEME 9

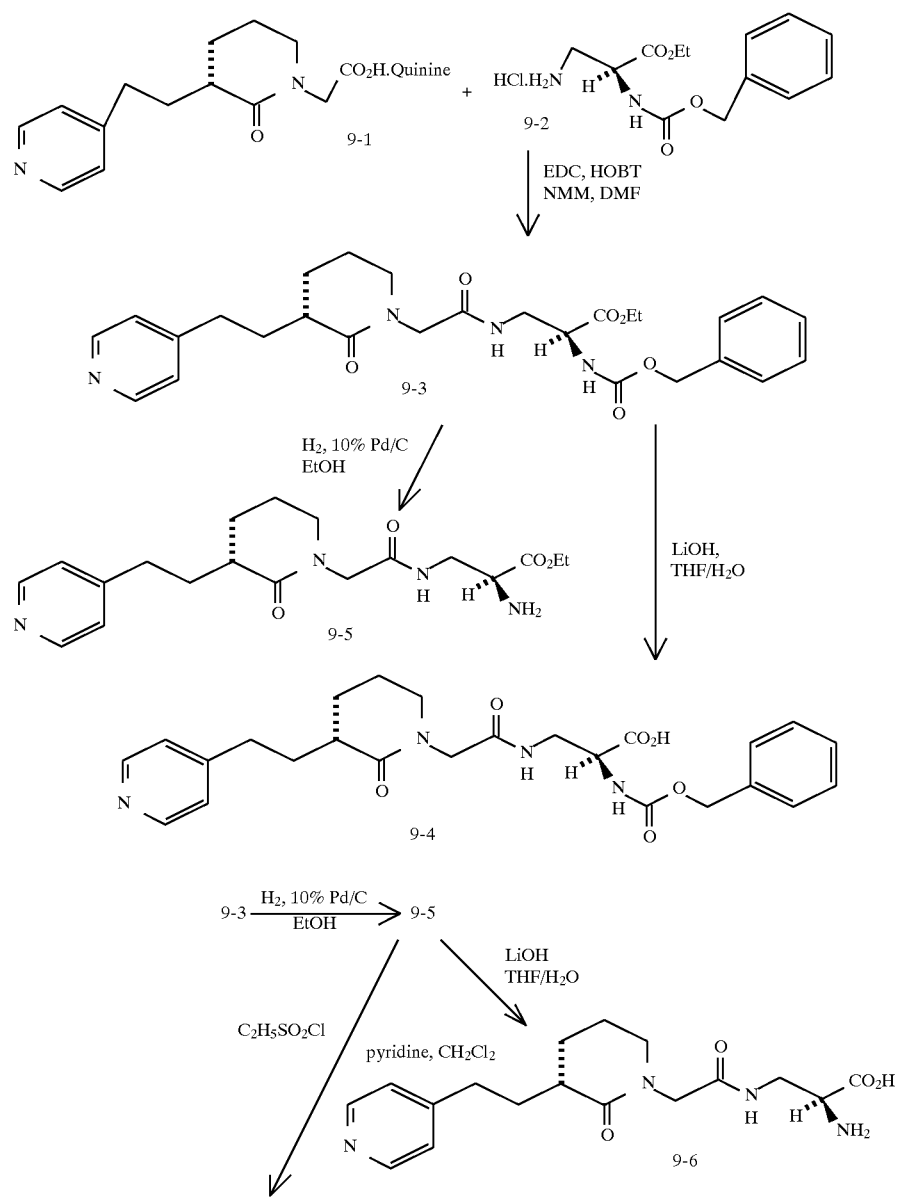

-continued
SCHEME 9

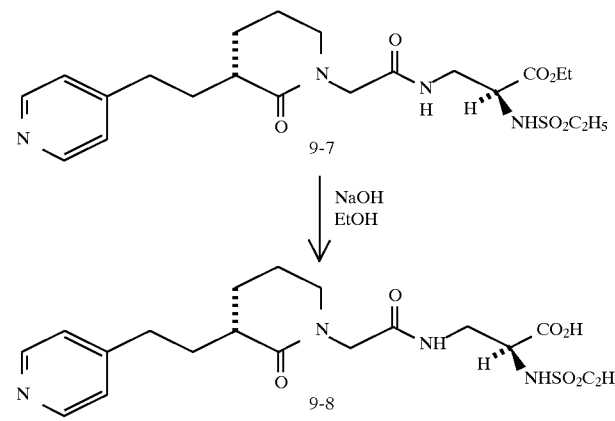

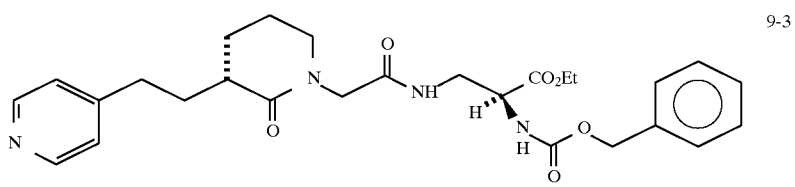

[3(R)-[2-(Pyridin-4-yl)ethyl]-2-piperidon-1-yl]acetyl-2(S)-benzyloxycarbonylamino-β-alanine ethyl ester (9-3)

(R)-Quininium [3(R)-[2-(pyridin-4-yl)ethyl]-2-piperidon-1-yl]acetate (described in PCT/US94/12671, U.S. Ser. No. 08/391,851) (9-1) 517 g, 8.0 mmol), 2(S)-benzyloxycarbonylamino-β-alanine ethyl ester hydrochloride (9-2). (2.4 g, 7.9 mmol), HOBT (1.3 g, 9.6 mmol) and NMM (3.1 mL, 28 mmol) were combined in 40 mL DMF, at −10° C., then EDC (1.84 g, 9.6 mmol) was added and the cooling bath was removed. After stirring overnight the mixture was concentrated, redissolved in EtOAc, washed with sat. NaHCO$_3$, water (3×), and brine, dried (MgSO$_4$), filtered and concentrated. Flash chromatography (silica, EtOAc then 10% MeOH/EtOAc) provided amide 9-3 as a white solid.

TLC R$_f$=0.48 (silica, 20% MeOH/EtOAc) $^1$H NMR (300 MHz, CDCl$_3$) δ8.60 (dd, J=5, 1 Hz, 2H), 7.46 (s, 5H) 7.25 (d, J=5 Hz, 2H), 7.04 (br t, 1H), 6.02 (br d, 1H), 5.22 (s, 2H), 4.55 (m, 1H), 4.37–4.18 (m, 3H), 3.90 (d, J=15 Hz, 1H), 3.79 (m, 2H), 3.50 (m, 2H), 2.81 (m, 2H), 2.50–2.30 (m, 2H), 2.20–1.82 (m, 4H), 1.78 (m, 1H), 1.40 (t, J=6 Hz, 3H).

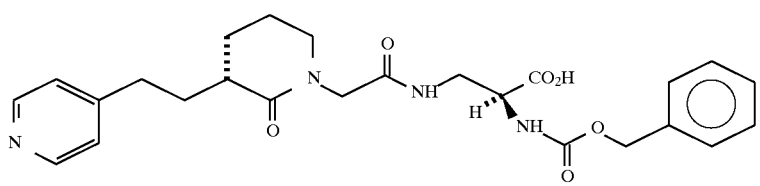

[3(R)-[2-(Pyridin-4-yl)ethyl]-2-piperidon-1-yl]acetyl-2(S)-benzyloxycarbonylamino-β-alanine (9-4)

Ester 9-3 (125 mg, 0.24 mmol) was dissolved in 3 mL 50% aqueous THF, and 1N LiOH (0.5 mL, 0.5 mmol) was added. After 2 h the reaction was concentrated. Flash chromatography (silica, 40:1:1 EtOH/H$_2$O/NH$_4$OH) provided acid (9-4) as a white solid.

TLC R$_f$=0.18 (silica, 40:1:1 EtOH/H$_2$O/NH$_4$OH)

1H NMR (400 MHz, D$_2$O ) δ8.32 (br d, J=6 Hz, 2H), 7.44 (br d, J=5 Hz, 2H), 7.24 (br s, 5H), 4.97 (d, J=12 Hz, 1H), 4.88 (d, J=13 Hz, 1H), 4.01 (m, 1H), 3.77 (s, 2H), 3.54 (m, 1H), 3.29 (m, 1H), 3.20–3.05 (m, 2H), 2.69 (m, 2H), 2.99 (m, 1H), 1.96 (m, 1H), 1.90–1.55 (m).

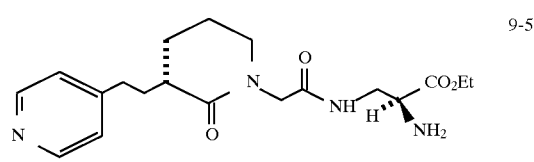

[3(R)-[2-(Pyridin-4-yl)ethyl]-2-piperidon-1-yl]acetyl-2(S)-amino-β-alanine ethyl ester (9-5)

Ester 9-3 (1.93 g, 3.78 mmol) was dissolved in 20 mL EtOH, 10% Pd/C (200 mg) was added, and the reaction was stirred under a balloon of H$_2$ for 2 d. After filtering through Celite, concentration provided amine 9-5 as a yellow oil.

TLC R$_f$0.8 (silica, 45:1:1 CH$_2$Cl$_2$/MeOH/HOAc)
$^1$H NMR (400 MHz, CDCl$_3$) δ8.49 (dd, J=4, 2 Hz, 2H), 7.16 (dd, J=5, 2 Hz, 2H), 7.10 (br t, 1H), 4.18 (q, J=7 Hz, 2H), 4.08 (AB d, J=15 Hz, 1H), 3.91 (AB d, J=15 Hz, 1H), 3.65 (m, 2H), 3.50–3.35 (m, 3H), 2.71 (m, 2H), 2.70–2.45 (br s, 2H), 2.41 (m, 1H), 2.26 (m, 1H), 2.08–1.75 (m, 4H), 1.65 (m, 1H), 1.28 (t, J=7 Hz, 3H).

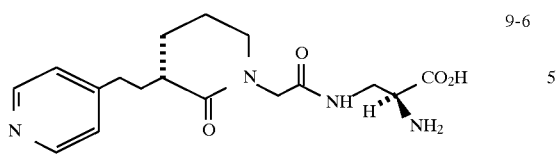

9-6

[3(R)-[2-(Pyridin-4-yl)ethyl]-2-piperidon-1-yl]acetyl-2(S)-amino-β-alanine (9-6)

Ester 9-5 (63 mg, 0.17 mmol) was combined with 1N LiOH (300 μL, 0.3 mmol) in 2 mL 50% aq. THF. After 2 h the reaction was concentrated and purified by flash chromatography (silica, 20:1:1, EtOH/H$_2$O/NH$_4$OH), providing acid 9-6 as a white solid.

TLC R$_f$=0.20 (silica, 20:1:1, EtOH/H$_2$O/NH$_4$OH)

$^1$H NMR (400 MHz, D$_2$O ) δ8.31 (d, J=6 Hz, 2H), 7.26 (d, J=6 Hz, 2H), 3.94 (AB m, 2H), 3.77 (dd, J=7, 4 Hz, 1H), 3.69 (dd, J=15, 4 Hz, 1H), 3.52 (dd, J=15, 7 Hz, 1H), 3.38–3.23 (m, 2H), 2.70–2.57 (m, 2H), 2.33 (m, 1H), 2.01 (m, 1H), 1.95–1.57 (m, 5H).

[3(R)-[2-(Pyridin-4-yl)ethyl]-2-piperidone-1-yl]-acetyl-2(S)-ethylsulfonylamino-β-alanine ethyl ester (9-7)

A stirred solution of amine 9-5 (600 mg, 1.59 mmol), pyridine (386 μL, 4.77 mmol) and CH$_2$Cl$_2$ (10 ml) at 0° C. was treated with ethanesulfonyl chloride (181 μL, 1.91 mmol). After 1 h, the cooling bath was removed and the solution was stirred at ambient temperature for 16 h. The reaction was diluted with EtOAc, washed with H$_2$O and brine, dried, concentrated and purified by flash chromatography (silica, 5% MeOH/EtOAc) providing 9-7 as a colorless oil.

TLC R$_f$=0.17 (silica, 5% MeOH/EtOAc)

$^1$H NMR (400 MHz, CDCl$_3$) δ8.48 (d, J=6 Hz, 2H), 7.15 (d, J=6 Hz, 2H), 6.97 (bt, 1H), 5.64 (d, J=9 Hz, 1H), 4.19 (m, 3H), 3.78 (m, 1H), 3.64 (m, 2H), 3.45 (m, 2H), 3.02 (m, 1H), 2.72 (bq, 2H), 2.41 (m, 1H), 2.28 (m, 1H), 1.91 (m, 4H), 1.66 (m, 1H), 1.35 (t, J=7 Hz, 3H), 1.26 (t, J=7 Hz, 3H).

[3(R)-[2-(Pyridin-4-yl)ethyl]-2-piperidone-1-yl]-acetyl-2(S)-ethylsulfonylamino-β-alanine (9-8)

Ester 9-7 (300 mg, 0.64 mmol) and 1N NaOH (2.0 mL, 2.0 mmol) were combined in EtOH (4 mL). After stirring at ambient temperature for 1 h, the reaction was concentrated and purified by flash chromatography (silica, 10:1:1 EtOH/NH$_4$OH/H$_2$O) providing 9-8 as a white solid.

TLC R$_f$=0.36 (silica, 10:1:1 EtOH/NH$_4$OH/H$_2$O)

$^1$H NMR (400 MHz, CD30D) δ8.40 (d, J=6 Hz, 2H), 7.35 (d, J=6 Hz, 2H), 4.06 (m, 1H), 3.98 (m, 2H), 3.67 (dd, J=9.4 Hz, 1H), 3.38 (m, 2H), 3.06 (qt, J=6, 2 Hz, 2H), 2.75 (m, 2H), 2.41 (m, 1H), 2.17 (m, 1H), 1.95 (m, 4H), 1.72 (m, 1H), 1.31 (t, J=7 Hz, 3H).

SCHEME 10

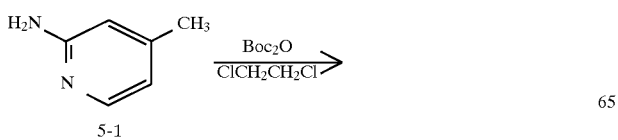

5-1

-continued
SCHEME 10

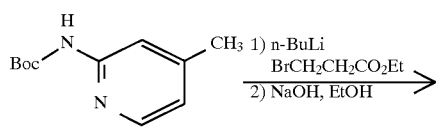

5-2

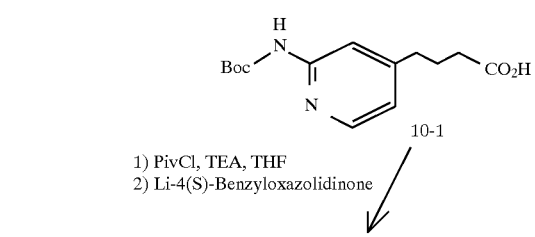

10-1

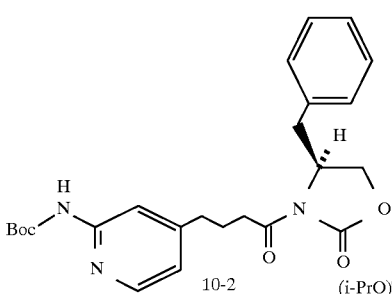

10-2

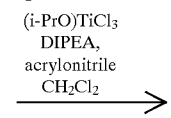

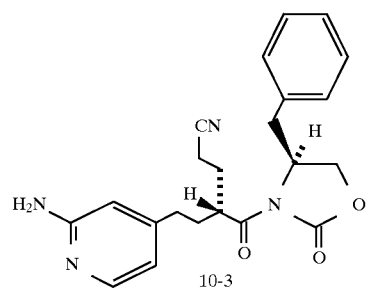

10-3

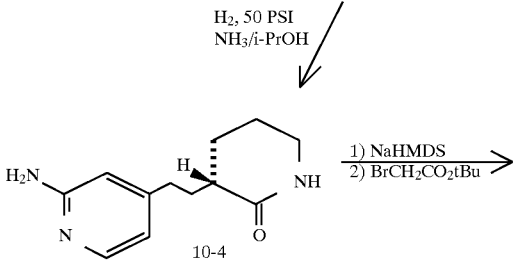

10-4

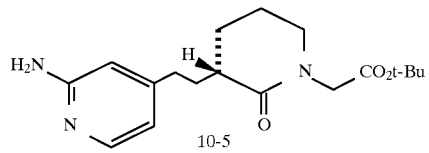

10-5

-continued
SCHEME 10

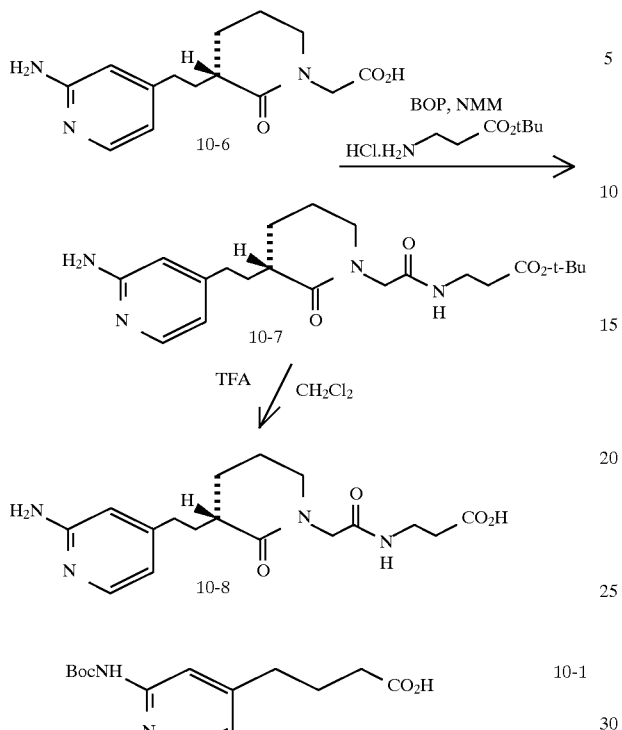

4-(2-N-Boc-Amino-4-pyridyl)butanoic acid (10-1)

The protected picoline 5-2 (90 g, 0.43 mol) was dissolved in 3 L THF under N$_2$, cooled to -78° C., and n-Buli (1.6M, 675 mL, 1.08 mol) was added during 30 min. The mixture was allowed to warm to RT for 1 h, then the resulting orange suspension was cooled to -78° C. Methyl 3-bromopropionate (79 g, 0.47 mol) was added during 2 min. After 15 min the cooling bath was removed and the mixture was allowed to warm to -20° C. at which point it was quenched with 60 mL HOAc in 250 mL THF. The solution was diluted with 2 L EtOAc, washed with water, sat. NaHCO$_3$, and brine, dried (MgSO$_4$). The aqueous layers were re-extracted with EtOAc (2×), and these organic layers were combined, washed with brine, and dried (MgSO$_4$). The combined organic layers were filtered, concentrated, and dissolved in 1.5 L EtOH and 1.5 L 1N NaOH (1.5 mol). After 1 h the reaction was concentrated by ⅓, diluted with 4 L EtOAc, the aqueous layer was removed. The pH of the aqueous layer was adjusted to 4–5 with 10% KHSO$_4$, then extracted with EtOAc (2×3 L). The EtOAc layers were washed with brine, dried (MgSO$_4$), filtered and concentrated, providing the acid 10-1 as a yellow oil.

TLC R$_f$ 0.65 (silica, 20:1:1 CH$_2$Cl$_2$/MeOH/HOAc).

$^1$H NMR (400 MHz, CD3OD) δ8.08 (d, J=5 Hz, 1H), 7.70 (s, 1H), 6.89 (d, J=5 Hz, 1H), 2.66 (t, J=8 Hz, 2H), 2.32 (t, J=7 Hz, 2H), 1.92 (quin, J=8 Hz, 2H), 1.52 (s, 9H).

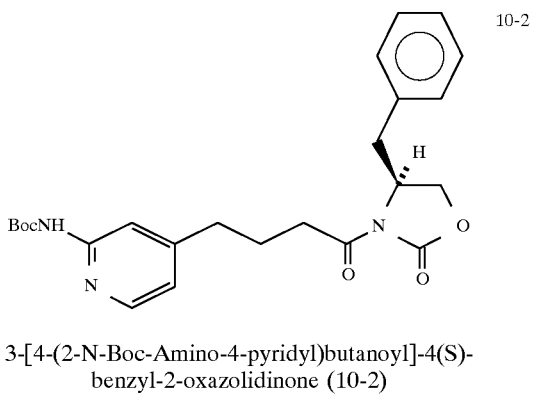

3-[4-(2-N-Boc-Amino-4-pyridyl)butanoyl]-4(S)-benzyl-2-oxazolidinone (10-2)

Acid 10-1 (667 mg, 2.38 mmol), and TEA (397 μL, 2.85 mmol) were combined in 12 mL THF, cooled to -78° C., and pivaloyl chloride (319 μg, 2.59 mmol) was added. After 10 min the reaction was warmed to 0° C. for 1 h, then cooled to -78° C. In a second flask, 4(S)-benzyl-2-oxazolidinone (464 mg, 2.62 mmol) was dissolved in 6 mL THF, cooled to -78° C., and n-Buli (1.6M, 1.64 mL, 2.62 mmol) was added. The second solution was added to the first, and the mixture was warmed to 0° C. for 1 h. The reaction was diluted with EtOAc, washed with water, sat. NaHCO$_3$10% KHSO$_4$, and brine, dried (MgSO$_4$), filtered and concentrated. Flash chromatography (silica, 20% EtOAc/hexanes) provided 10-2 as a white solid.

TLC R$_f$ 0.41 (silica, 40% EtOAc/hexanes).

$^1$H NMR (400 MHz, CDCl$_3$) δ8.17 (d, J=5 Hz, 1H), 8.12 (s, 1H), 7.83 (s, 1H), 7.36–7.24 (m, 3H), 7.21 (d, J=8 Hz, 2H), 6.83 (d, J=5 Hz, 1H), 4.67 (m, 1H), 4.20–4.10 (m, 2H), 3.30 (dd, J=13, 3 Hz, 1H), 3.05–2.90 (m, 2H), 2.78 (dd, J=13, 10 Hz, 1H), 2.73 (t, J=6 Hz, 2H), 2.06 (quin, J=8 Hz, 2H), 1.53 (s, 9H).

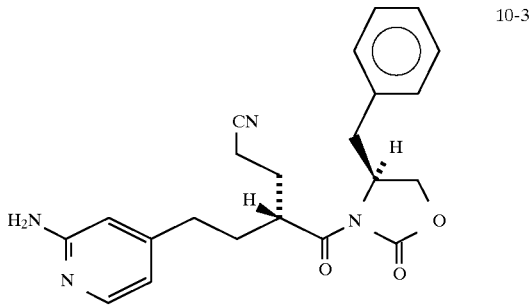

3-[4-(2-Amino-4-pyridyl)-2(R)-(2-cyanoethyl)butanoyl]-4(S)-benzyl-2-oxazolidinone (10-3)

Ti(i-PrO)$_4$ (2.19 mL, 7.37 mmol) was added to a solution of TiCl$_4$ (1M in CH$_2$Cl$_2$, 22.1 mL, 22.1 mmol) in 40 mL CH$_2$Cl$_2$ at 0° C. After 15 min, DIPEA (5.15 mL, 30 mmol) was added and the solution turned deep red. After stirring for 10 min, a solution of the oxazolidinone 10-2 (2.6 g, 5.92 mmol) in 10 mL CH$_2$Cl$_2$ was added, and after 1 h at 0° C., acrylonitrile (3.90 mL, 59 mmol) was added and the reaction was stirred at RT overnight. The reaction was diluted with EtOAc, washed with NaHCO$_3$ and brine, dried (MgSO$_4$), filtered and concentrated. Flash chromatography (silica, EtOAc then 2% MeOH/EtOAc) provided nitrile 10-3 as an orange gum.

TLC R$_f$ 0.12 (silica, EtOAc).

$^1$H NMR (400 MHz, CDCl$_3$) δ7.95 (d, J=5 Hz, 1H), 7.37–7.25 (m, 3H), 7.19 (d, J=8 Hz, 1H), 6.47 (d, J=5 Hz,

1H), 6.31 (s, 1H), 4.52 (m, 1H), 4.35 (s, 2H), 4.16 (m, 2H), 3.90 (m, 1H), 3.29 (dd, J=13, 3 Hz, 1H), 2.75 (dd, J=13, 10 Hz, 1H), 2.60–2.45 (m, 2H), 2.38 (t, J=8 Hz, 2H), 2.20–2.06 (m, 2H), 1.92 (, 1H), 1.80 (m, 1H).

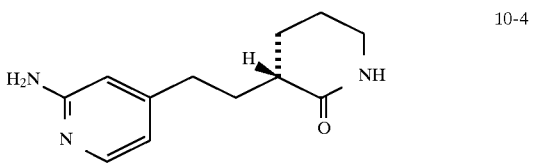

3(R)-[(2-Amino-4-pyridyl)ethyl]-2-piperidone (10-4)

Nitrile 10-3 (9.48 g, 24.2 mmol) was dissolved in 200 mL i-PrOH sat. with $NH_3$.5% Rh on alumina (10.69 g) was added, and the mixture was hydrogenated on a Parr shaker at 50 psi $H_2$ pressure. After 3 d, the reaction mixture was filtered through Celite, re-saturated with $NH_3$, treated with fresh 5% Rh on alumina (3.00 g), and hydrogenated at 50 psi for 1 d more. After filtering through Celite, the mixture was concentrated and purified by flash chromatography (silica, $CH_2Cl_2$, then 10%, 20%, then 30% $NH_3$ sat. $EtOH/CH_2Cl_2$) to provide the lactam 10-4 as a crystalline yellow solid.

TLC $R_f$ 0.48 (silica, 20% $NH_3$ sat. $EtOH/CH_2Cl_2$).
$^1H$ NMR (400 MHz, $CDCl_3$) δ7.94 (d, J=5 Hz, 1H), 6.53 (dd, J=5, 1 Hz, 1H), 6.39 (s, 1H), 5.91 (br s, 1H), 4.41 (br s, 2H), 3.31 (m, 2H), 2.70–2.50 (m, 2H), 2.35–2.10 (m, 2H), 1.98 (m, 1H), 1.87 (m, 1H), 1.80–1.65 (m, 2H), 1.56 (m, 1H).

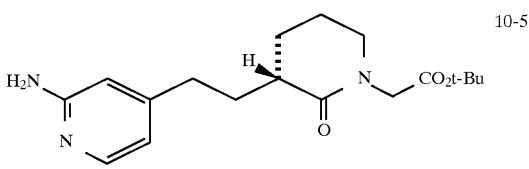

t-Butyl (3(R)-[(2-amino-4-pyridyl)ethyl]-2-piperidon-1-yl)acetate (10-5)

Lactam 10-4 (246 mg, 1.12 mmol) was dissolved in 32 mL THF, cooled to −78° C., and NaHMDS (1M, 1.35 mL, 1.35 mmol) was added. After 15 min t-butyl bromoacetate (218 μl, 1.35 mmol) was added to the stirring suspension, and after 1 h the reaction was quenched by addition of water. After warming to RT the mixture was extracted with EtOAc (3×), the combined organic layers were washed with water and brine, dried ($MgSO_4$), filtered and concentrated. Flash chromatography (silica, $CH_2Cl_2$, then 10% then 20% $NH_3$ sat. $EtOH/CH_2Cl_2$) provided ester 10-5.

TLC $R_f$ 0.54 (silica, 10% $NH_3$ sat. $EtOH/CH_2Cl_2$)
$^1H$ NMR (400 MHz, $CDCl_3$) δ7.93 (d, J=5 Hz, 1H), 6.51 (d, J=5 Hz, 1H), 6.38 (s, 1H), 4.42 (bs, 2H), 4.07 (d, J=17 Hz, 1H), 3.89 (d, J=17 Hz, 1H), 3.34 (m, 2H), 2.59 (m, 2H), 2.35 (m, 1H), 2.21 (m, 1H), 1.96 (m, 2H), 1.79 (m, 2H), 1.62 (m, 1H), 1.46 (s, 9H).

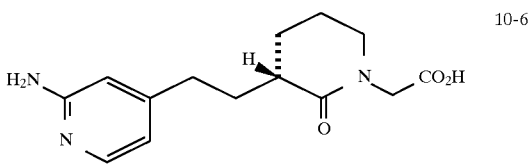

(3(R)-[(2-Amino-4-pyridyl)ethyl]-2-piperidon-1-yl) acetic acid hydrochloride (10-6)

A solution of 10-5 (240 mg, 0.72 mmol), trifluoroacetic acid (5 mL) and $CH_2Cl_2$ (5 mL) was stirred at ambient temperature for 30 min. The reaction mixture was then concentrated and the residual trifluoroacetic acid removed azeotropically with toluene. The oily solid was diluted with 1N HCl and then concentrated to give the hydrochloride salt 10-6.

TLC $R_f$ 0.1 (silica, 30% $NH_3$ sat. $EtOH/CH_2Cl_2$)
$^1H$-NMR (300 MHz, $D_2O$) δ7.68 (d, J=7 Hz, 1H), 6.84 (d, J=7 Hz, 1H), 6.81 (s, 1H), 4.15 (d, J=17 Hz, 1H), 4.04 (d, J=17 Hz, 1H), 3.42 (m, 2H), 2.73 (t, J=8 Hz, 2H), 2.45 (m, 1H), 1.89 (m, 6H).

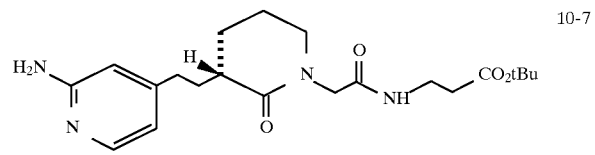

(3(R)-[(2-Amino-4-pyridyl)ethyl]-2-piperidon-1-yl) acetyl-β-alanine-tert-butyl ester (10-7)

To a stirred solution of 10-6 (115 mg, 0.364 mmol),β-alanine t-butyl ester hydrochloride (132 mg, 0.73 mmol), and NMM (140 μL, 1.27 mmol) in 3.6 mL DMF at ambient temperature was added BOP (241 mg, 0.55 mmol). After stirring overnight the mixture was concentrated, redissolved in EtOAc, washed with sat. $NaHCO_3$, water (3×), and brine, dried ($MgSO_4$), filtered and concentrated. Flash chromatography (silica, $CH_2CL_2$ then 5% then 10% $NH_3$ sat. $EtOH/CH_2Cl_2$) provided amide 10-7 as a clear oil.

TLC $R_f$ 0.65 (silica, 10% $NH_3$ sat. $EtOH/CH_2Cl_2$)
$^1H$-NMR (400 MHz, $CDCl_3$) δ7.93 (d, J=6 Hz, 1H), 6.76 (bs, 1H), 6.52 (d, J=6 Hz, 1H), 6.39 (s, 1H), 3.97 (dd, J=15, 6 Hz, 2H), 3.47 (q, J=6 Hz, 2H), 3.37 (m, 2H), 2.6 (m, 2H), 2.42 (t, J=6 Hz, 2H), 2.34 (m, 1H), 2.23 (m, 1H), 1.97 (m, 2H), 1.78 (m, 2H), 1.63 (m, 1H), 1.43 (s, 9H).

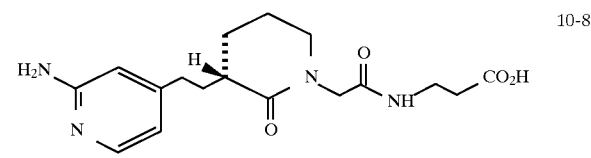

(3(R)-[(2-Amino-4-pyridyl)ethyl]-2-piperidon-1-yl) acetic-β-alanine (10-8)

A solution of ester 10-7 (76 mg, 0.187 mmol), trifluoroacetic acid (2 mL), and $CH_2Cl_2$ (2 mL) was stirred at ambient temperature for 20 minutes. The reaction mixture was then concentrated and the residual trifluoroacetic acid removed azeotropically with toluene. Flash chromatography (silica, 50% $EtOAc/10:1:1$ $EtOH/NH4/OH/H_2O$) afforded 10-8 as a white solid.

TLC $R_f$ 0.12 (silica, 50% $EtOAc/10:1:1$ $EtOH/NH_4OH/H_2O$)
$^1H$-MR (400 MHz, $D_2O$) δ7.17 (s, 1H), 6.83 (m, 2H), 4.00 (bs, 2H), 3.41 (bm, 4H), 2.73 (t, J=7 Hz, 2H), 2.46 (m, 1H), 2.4 (m, 2H), 1.89 (bm, 6H).

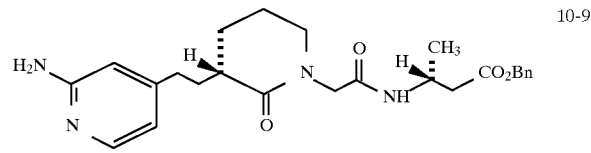

(3(R)-[(2-Amino-4-pyridyl)ethyl]-2-piperidon-1-yl) acetyl -3(R)-methyl-β-alanine benzyl ester (10-9)

A a stirred solution of 10-6 (130 mg, 0.415 mmol), 4-1 (160 mg, 0.83 mmol), and NMM (160 μL, 1.45 mmol) in 4 mL DMF at ambient temperature was added BOP (275 mg, 0.622 mmol). After stirring overnight, the mixture was concentrated, redissolved in EtOAc, washed with H₂O (3×), sat. NaHCO₃, brine, dried (MgSO₄), filtered, and concentrated. Flash chromatograph (silica, CH₂Cl₂ then 5% then 10% NH₃ sat. EtOH/CH₂Cl₂) provided amide 10-9 as a clear oil.

TLC $R_f$ 0.48 (silica, 10% NH₃ sat. EtOH/CH₂Cl₂)

¹H-NMR (400 MHz, CDCl₃) δ7.93 (d, J=5 Hz, 1H), 7.34 (m, 5H), 6.78 (d, J=8 Hz, 1H), 6.51 (d, J=5 Hz, 1H), 6.37 (s, 1H), 5.09 (dd, J=12, 3 Hz, 2H), 4.35 (bm, 3H), 4.04 (d, J=15 Hz, 2H), 3.83 (d, J=5 Hz, 2H), 3.34 (m, 2H), 2.57 (m, 4H), 2.35 (m, 1H), 2.21 (m, 1H), 1.95 (bm, 2H), 1.77 (m, 2H), 1.61 (m, 1H), 1.20 (d, J=7 Hz, 3H).

SCHEME 11

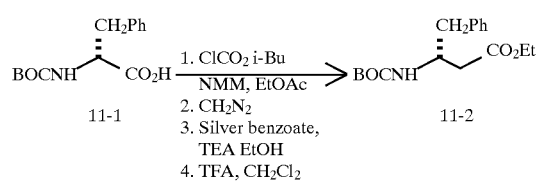

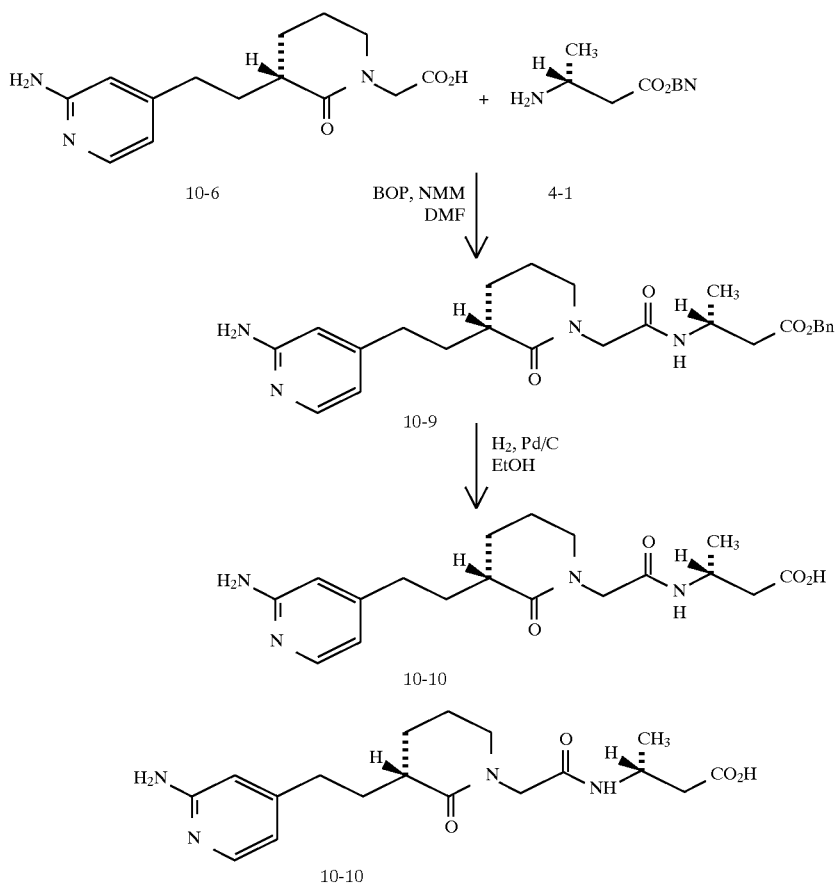

(3(R)-[(2-Amino-4-pyridyl)ethyl]-2-piperidon-1-yl) acetyl-3(R)-methyl-β-alanine (10-10)

Ester 10-9 (145 mg, 0.32 mmol) was dissolved in 3.5 mL EtOH, 10% Pd/C (100 mg) was added and the reaction was stirred under a balloon of H₂ for 6 hrs. The mixture was filtered through celite and concentrated to an oil. Flash chromatography (silica, 50% EtOAc/10:1:1 EtOH/NH₄OH/H₂O) provided 10-10 as a white solid.

TLC $R_f$ 0.27 (silica, 60% EtOAC/10:1:1 EtOH/H₂O/NH₄OH)

¹H-NMR (300 MHz, D₂O) δ7.72 (d, J=6 Hz, 1H), 6.83 (m, 2H), 4.17 (q, J=6.6 Hz, 1H), 3.99 (dd, J=7, 16 Hz, 2H), 3.41 (m, 2H), 2.73 (t, J=8 Hz, 2H), 2.37 (m, 3H), 1.90 (m, 5H), 1.17 (d, J=6.6 Hz, 3H).

-continued
SCHEME 11

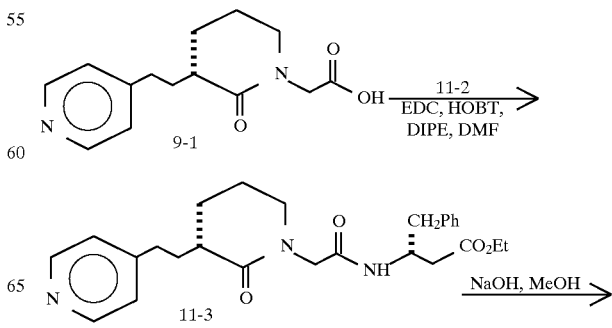

-continued
SCHEME 11

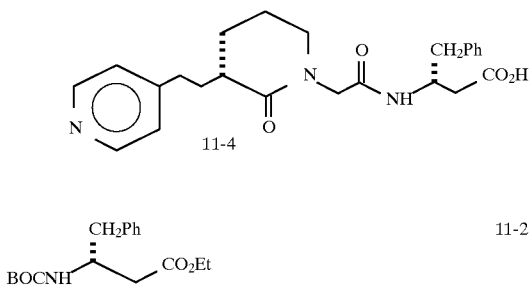

11-4

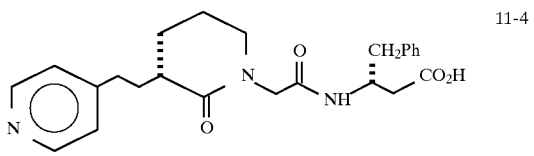

11-2

Ethyl N-Boc-3(R)-benzylβ-alanine trifluoroacetate salt (11-2)

To a cold (−10° C.) solution of N-Boc-D-Phenylalanine (796 mg, 3 mmol), 4-methylmorpholine (0.4 mL, 3.6 mmol) in ethyl acetate (35 mL), isobutyl chloroformate (0.47 mL, 3.6 mmol) was added. The resultant mixture was stirred at 0° C. for 1 h, washed with water, brine, dried over anhydrous magnesium sulfate, and filtered. The filtrate was cooled to 0° C., and was treated with an etheral solution of diazomethane (11 mmol). After stirring at 0° C. for 2 h, the cooling bath was removed and excess diazomethane was removed by purging with argon. The resultant solution was concentrated under vacuo. The yellow solid was then dissolved in absolute ethanol (20 mL), and the solution cooled to 0° C. Triethylamine (0.48 mL, 3.6 mmol) and silver benzoate (206 mg, 0.9 mmol) was added, and after a vigorous evolution of gas, the reaction mixture turned black. The resultant mixture was concentrated onto silica gel, and subjected to column chromatography on silica gel eluted with 25% ethyl acetate in hexane. Collection and concentration of appropriate fractions provided the ethyl ester as a white waxy solid.

To a solution of the above product (657 mg) in dichloromethane (10 mL), trifluoroacetic acid (4 mL) was added. The reaction mixture was stirred at room temperature for 2 h, and concentrated under vacuo to give 659 mg (88.2%) of the TFA salt, 11-2.

$^1$H-NMR (300 MHz, CDCl$_3$) δ7.3–7.1 (m, 5H), 5.0–4.5 (br s, 3H), 4.15 (q, J=7 Hz, 2H), 3.78 (br t, 1H), 3.17 (dd, J=14 & 7 Hz, 1H), 2.88 (dd, J=14 & 17 Hz, 1H), 2.69 (d, 6 Hz, 2H), 1.25 (t, J=7 Hz).

11-4

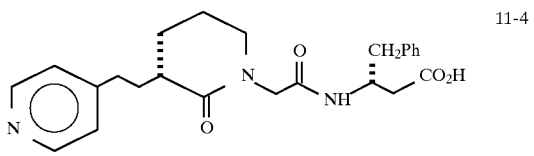

(3(R)-[2-(Pyridin-4-yl)ethyl]-2-piperidon-1-yl) acetyl-3(R)-benzyl-β-alanine (11-4)

To a solution of (R)-quininium [3(R)-[2-(pyridin-4-yl) ethyl]-2-piperidon-1-yl]acetate (9-1) (423 mg, 0.74 mmol), ethyl 3(R)-benzylβ-alanine trifluoroacetate salt 11-2 (260 mg, 0.72 mmol), HOBT (107 mg, 0.79 mmol) and diisopropylethylamine (440 μL, 2.5 mmol) DMF (8 mL) at rt, EDC (150 mg, 0.78 mmol) was added. After stirring overnight the mixture was concentrated, redissolved in EtOAc, washed with sat. NaHCO$_3$, water (3×), and brine, dried (MgSO$_4$), filtered and concentrated. Flash chromatography on silica gel eluting with 3% methanol in chloroform provided the amide ester 11-3.

To a solution 11-3 (126 mg, 0.28 mmol) in methanol (4 mL), 1M aq. NaOH (1 mL, 1 mmol) was added. The reaction mixture was stirred at rt for 4H (monitored by tlc), and pH adjusted to 7 by addition of trifluoroacetic acid. The mixture was concentrated and subjected to HPLC on a C-18 column eluting with an acetonitrile-water (0–50% gradient over 50 min). Collection and lyophilization of appropriate fractions provided 11-4.

$^1$H-NMR (300 MHz, CD$_3$OD) δ8.70 (d, J=6.6 Hz, 1H), 7.97 (d, J=6.6 Hz, 1H), 7.23 (m, 5H), 4.45 (m, 1H), 3.96 (m, 2H), 3.19 (m, 1H), 3.02 (m, 2H), 2.83 (m, 2H), 2.51 (m, 3H), 2.19 (m, 1H), 2.1–1.6 (m, 5H).

Analysis calculated for C$_{24}$H$_{29}$N$_3$O$_4$.1.54 TFA.0.48 H$_2$O C, 53.52; H, 5.22; N, 6.91 Found: C, 53.53; H, 5.23; N, 7.12

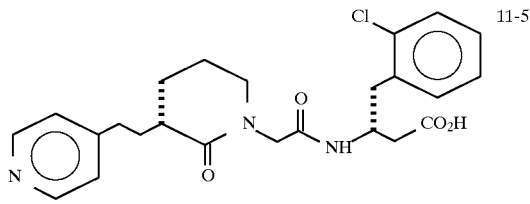

11-5

(3(R)-[2-(Pyridin-4-yl)ethyl]-2-piperidon-1-yl) acetyl-3(R)-2-chlorobenzyl-β-alanine (11-5)

Following procedures as described for 11-4, and substituting with N-Boc-D-2-chlorophenylalanine, [3(R)-(Pyridin-4-yl) ethyl]-2-piperidon-1-yl]acetyl-3(R)-2-chlorobenzyl-β-alanine (11-5) was prepared.

$^1$H-NMR (300 MHz, CD$_3$OD) δ8.71 (d, J=6.6 Hz, 1H), 7.98 (d, J=6.6 Hz, 1H), 7.23 (m, 4H), 4.60 (m, 1H), 3.94 (m, 2H), 2.55 (m, 3H), 2.18 (m, 1H), 2.1–1.6 (m, 5H).

Analysis calculated for C$_{24}$H$_{28}$ClN$_3$O$_4$.1.94 TFA.0.28 H$_2$O C, 48.94; H, 4.49; N, 6.14 Found: C, 48.94; H, 4.50; N, 6.31

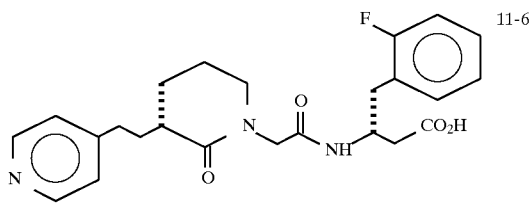

11-6

(3(R)-[2-(Pyridin-4-yl)ethyl]-2-piperidon-1-yl) acetyl-3(R)-2-fluorobenzyl-β-alanine (11-6)

Following procedures as described for 11-4, and substituting with N-Boc-D-2-fluorophenylalanine, [3(R)-[2-(Pyridin-4-yl) ethyl]-2-piperidon-1-yl]acetyl-3(R)-2-fluorobenzyl-β-alanine (11-6) was prepared.

$^1$H-NMR (300 MHz, CD$_3$OD) δ8.71 (d, J=6.6 Hz, 1H), 7.98 (d, J=6.6 Hz, 1H), 7.25 (m, 2H), 7.05 (m, 2H), 4.50 (m, 1H), 3.95 (s, 2H), 3.19 (m, 1H), 3.10–2.82 (m, 4H), 2.58–2.42 (m, 3H), 2.55 (m, 3H), 2.20 (m, 1H), 2.1–1.6 (m, 5H).

Analysis calculated for C$_{24}$H$_{28}$FN$_3$O$_4$.1.64 TFA.0.90 H$_2$O C, 50.82; H, 4.92; N, 6.52 Found: C, 50.81; H, 4.91; N, 6.71

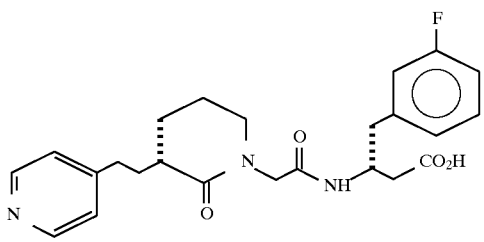
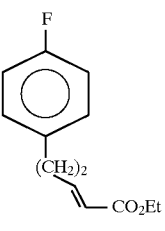

[3(R)-[2-(Pyridin-4-yl)ethyl]-2-piperidon-1-yl]
acetyl-3(R)-3-fluorobenzyl-β-alanine (11-7)

Following procedures as described for 11-4, and substituting with N-Boc-D-3-fluorophenylalanine, [3(R)-[2-(Pyridin-4-yl) ethyl]-2-piperidon-1-yl)acetyl-3(R)-3-fluorobenzyl-β-alanine 11-7 was prepared.

¹H-NMR (300 MHz, CD₃OD) δ8.71 (d, J=6.6 Hz, 1H), 7.98 (d, J=6.6 Hz, 1H), 7.28 (m, 1H), 7.1–6.9 (m, 3H), 4.45 (m, 1H), 3.95 (s, 2H), 3.19 (m, 1H), 3.10–2.82 (m, 4H), 2.58–2.42 (m, 3H), 2.55 (m, 3H), 2.20 (m, 1H), 2.1–1.6 (m, 5H).

Analysis calculated for C₂₄H₂₈FN₃O₄.1.64 TFA.0.62 H₂O C, 51.22; H, 4.87; N, 6.57 Found: C, 51.23; H, 4.86; N, 6.59

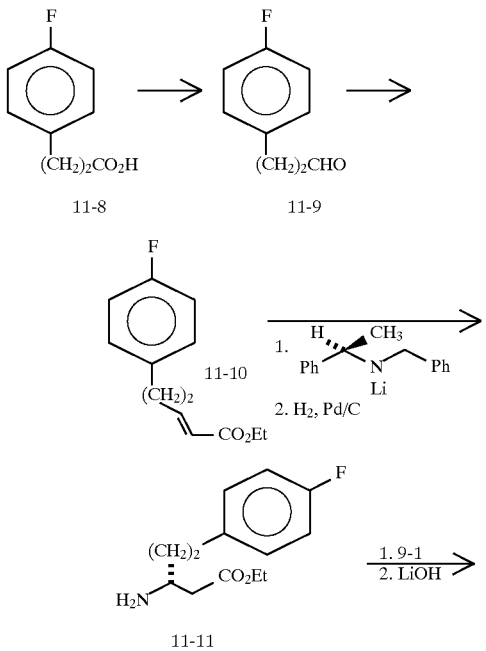

Ethyl 5-(4-fluorophenyl)-2(E)-pentenoate (11-10)

To a cold (0° C.) solution of 3-(4-fluorophenyl)propionic acid 11-8 (0.84 g, 5 mmol) in ethyl acetate (15 mL), NMM (1.15 mL, 10 mmol), and isobutylchloroformate (0.67 mL, 5 mmol) were added. After stirring for 30 min, N,O-dimethylhydroxylamine HCl (0.51 g, 5.2 mmol) was added, and the reaction mixture was stirred at rt overnight. The resultant mixture was successively washed with water, aq. HCl (0.2M), brine, and dried over anhydrous magnesium sulfate. The solution was filtered and concentrated under vacuo to give the desired amide as a clear colorless oil.

To a cold (−55° C.) suspension of LAH (192 mg, 5 mmol) in anhydrous ether (20 mL), a solution of the above amide (1 g, 4.8 mmol) in anhydrous ether was added with the temperature of the reaction kept below −50° C. After addition was completed, the reaction mixture was allowed to warm to 5° C., and then cooled back to −35° C. A saturated aq. solution of potassium hydrogen sulfate (6 mL) was added. The resultant mixture was stirred at rt for 1 h, and filtered through a pad of Celite. The filtrate was washed with aq HCl (0.2M), brine, dried over magnesium sulfate, and filtered. Concentration of the filtrate under vacuo provided the aldehyde, 11-9.

To a solution of the above aldehyde (0.67 g, 4.4 mmol) in methylene chloride (15 mL), (carbethoxymethylene)triphenylphosphorane (2.29 g, 6.5 mmol) was added, and the reaction mixture was stirred at rt overnight. The resultant mixture was concentrated onto silica gel and subjected to column chromatography on silica gel eluting with 2:5 ethyl acetate in hexane. Collection and concentration of appropriate fractions provided 0.7 g of the α,β-unsaturated ester, 11-10.

¹H-NMR (300 MHz, CDCl₃) δ7.14 (m, 2H), 6.98 (m, 3H), 5.82 (dt, J=15.6 & 7 Hz, 1H), 4.18 (q, J=7.1 Hz, 2H), 2.73 (t, J=7 Hz), 2.51 (q, J=7 Hz), 1.28 (t, J=7.1 Hz, 3H).

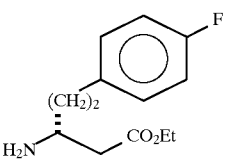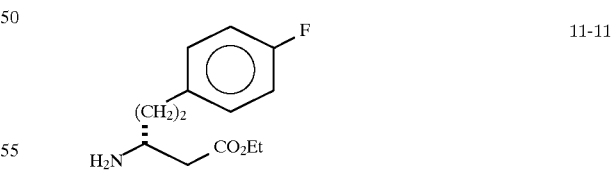

Ethyl 3(R)-4-fluorophenylethylβ-alanine (11-11)

To a cooled (0° C.) solution of (R)-(+)-α-methylbenzyl benzyl amine (1.24 g, 5.87 mmol) in anhydrous THF (65 mL), a solution of n-BuLi in hexane (2.5M, 2.4 mL, 6 mmol) was added. The resultant bright red solution was stirred at 0° C. for 20 min, and cooled to −78° C. A solution of ethyl 5-(4-fluorophenyl)-2(E)-pentenoate 11-10 (0.7 g, 3.15 mmol) in THF (12 mL) was added dropwise over a period of 15 min. The resultant yellow solution was stirred at −78° C. for 15 min, and was quenched with 6.5 mL saturated aq.

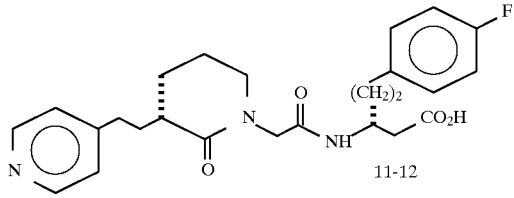

ammonium chloride. The ethereal solution was washed with brine, dried over anhydrous sodium sulfate, filtered, and concentrated under vacuo. The residue was subjected to column chromatography on silica gel eluting with 15% ethyl acetate in hexane. Collection and concentration of appropriate fractions provided the desired bisbenzyl alanine as a clear colorless oil.

A mixture of the bisbenzyl alanine (300 mg, 0.69 mmol), glacial acetic acid (0.2 mL, 3.5 mmol), 44 mg of 10% palladium on charcoal, and methanol (50 mL) was subjected to an atmosphere of hydrogen gas at 50 psi on a Parr hydrogenator for 17 h. The resultant mixture was filtered through a pad of Celite and concentrated under vacuo to provide quantitatively ethyl 3(R)-4-fluorophenylethylβ-alanine 11-11 as an acetate salt.

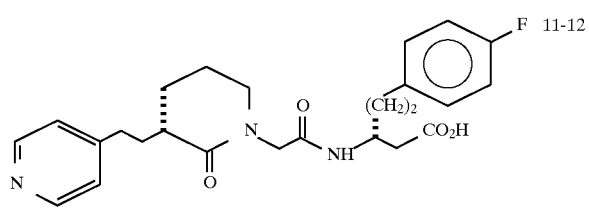

[3(R)-[2-(Pyridin-4-yl)ethyl]-2-piperidon-1-yl)] acetyl-3(R)-4-fluorophenyl ethyl-β-alanine (11-12)

Following procedures as described for 11-4, and substituting with ethyl 3(R)-4-fluorophenylethylβ-alanine 11-11, [3(R)-[2-(Pyridin-4-yl)ethyl]-2-piperidin-1-yl]acetyl-3(R)-4-fluorophenylethyl-β-alanine (11-12) was prepared.

$^1$H-NMR (300 MHz, CD$_3$OD) δ8.65 (d, J=6.3 Hz, 1H), 8.01 (d, 8.6 Hz, 1H), 7.92 (d, J=6.3 Hz, 1H), 7.19 (m, 2H), 6.93 (m, 2H), 4.22 (m, 1H), 4.19 (d, J=16 Hz, 1H), 3.83 (d, J=16 Hz, 1H), 3.49 (m, 1H), 3.35 (m, 1H), 3.01 (m, 2H), 2.72–2.45 (m, 5H), 2.22–1.73 (m, 9H).

Analysis calculated for C$_{25}$H$_{30}$FN$_3$O$_4$.1.23 TFA.0.95 H$_2$O C, 53.81; H, 5.45; N, 6.86 Found: C, 53.81; H, 5.45; N, 6.82

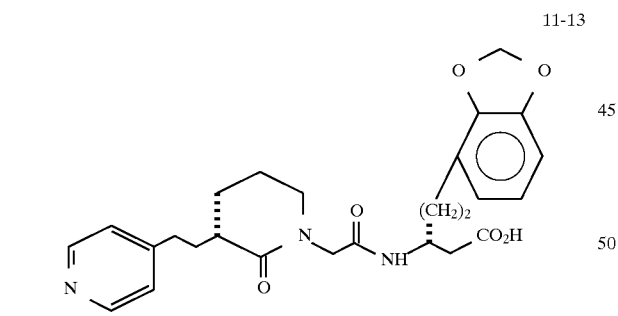

[3(R)-[2-(Pyridin-4-yl)ethyl]-2-piperidon-1-yl) acetyl-3(R)-3,4-methylenedioxyphenylethyl-(11-13)

Following procedures substantially similar to those described for 11-4 and 11-12, and substituting with 3-(3,4-methylenedioxyphenyl)propionic acid, [3(R)-[2-(Pyridin-4-yl)ethyl]-2-piperidon-1-yl]acetyl-3(R)-3,4-methylenedioxyphenylethyl-β-alanine (11-13) was prepared.

$^1$H-NMR (300 MHz, CD$_3$OD) δ8.65 (d, J=6.6 Hz, 1H), 8.01 (d, 8.6 Hz, 1H), 7.94 (d, J=6.6 Hz, 1H), 6.69 (br s, 1H), 6.65 (br s, 2H), 5.85 (s, 2H), 4.22 (m, 1H), 4.21 (d, J=16 Hz, 1H), 3.81 (d, J=16 Hz, 1H), 3.50 (m, 1H), 3.02 (m, 2H), 2.7–2.4 (m, 5H), 2.22–1.73 (m, 9H).

Analysis calculated for C$_{26}$H$_{31}$N$_3$O6.1.30 TFA.0.76 H$_2$O C, 53.39; H, 5.30; N, 6.53 Found: C, 53.38; H, 5.29; N, 6.60

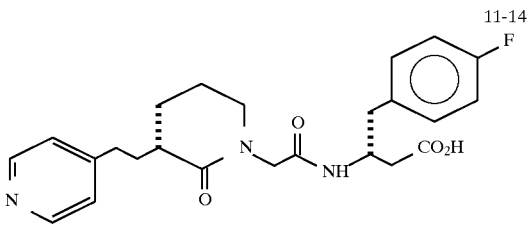

[3(R)-[2-(Pyridin-4-yl)ethyl]-2-piperidon-1-yl) acetyl-4-fluorobenzyl-β-alanine (11-14)

Following procedures substantially similar to those described for 11-4, and substituting with N-Boc-D-4-fluorophenylalanine, 11-14 was prepared.

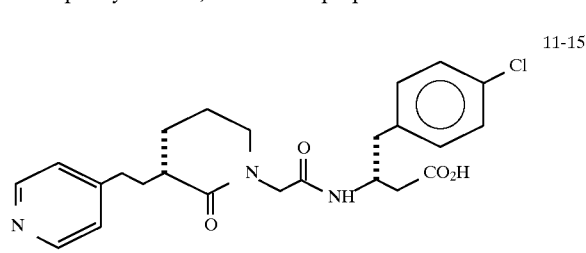

[3(R)-[2-(Pyridin-4-yl)ethyl]-2-piperidon-1-yl) acetyl-4-chlorobenzyl-β-alanine (11-15)

Following procedures substantially similar to those described for 11-4, and substituting with N-Boc-3(R)-4-chlorophenylalanine, 11-15 was prepared.

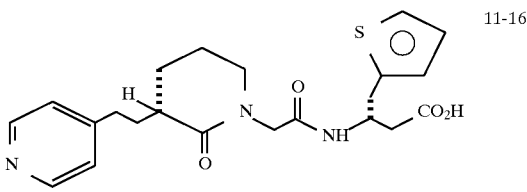

[3(R)-[2-(Pyridin-4-yl)ethyl]-2-piperidon-1-yl) acetyl-3(R)-3-(2-thienyl methyl)-β-alanine (11-16)

Following procedures substantially similar to those described for 11-4, and substituting with N-Boc-3(R)-(2-thienylmethyl)-β-alanine, 11-16 was prepared.

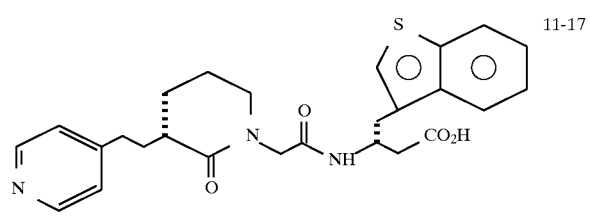

[3(R)-[2-(Pyridin-4-yl)ethyl]-2-piperidon-1-yl) acetyl-3(R)-3-benzylthienyl)-β-alanine (11-17)

Following procedures substantially similar to those described for 11-4, and substituting with N-Boc-3(R)-(3-benzothienyl)-β-alanine, 11-17 was prepared.

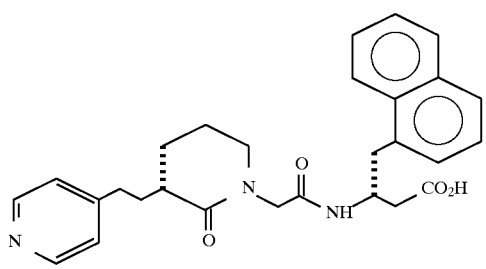

[3(R)-[2-(Pyridin-4-yl)ethyl]-2-piperidon-1-yl]
acetyl-3(R)-(1-naphthyl)-β-alanine (11-18)

Following procedures substantially similar to those described for 11-4, and substituting with N-Boc-3(R)-(1-naphthyl)-β-alanine, 11-18 was prepared.

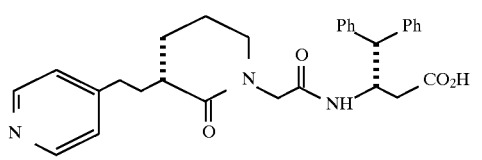

[3(R)-[2-(Pyridin-4-yl)ethyl]-2-piperidon-1-yl]
acetyl-3(R)-(1,1-diphenylmethyl)-β-alanine (11-19)

Following procedures substantially similar to those used for 11-4, and substituting with N-Boc-3(R)-(1,1-diphenylmethyl)-β-alanine, 11-19 was prepared.

SCHEME 12

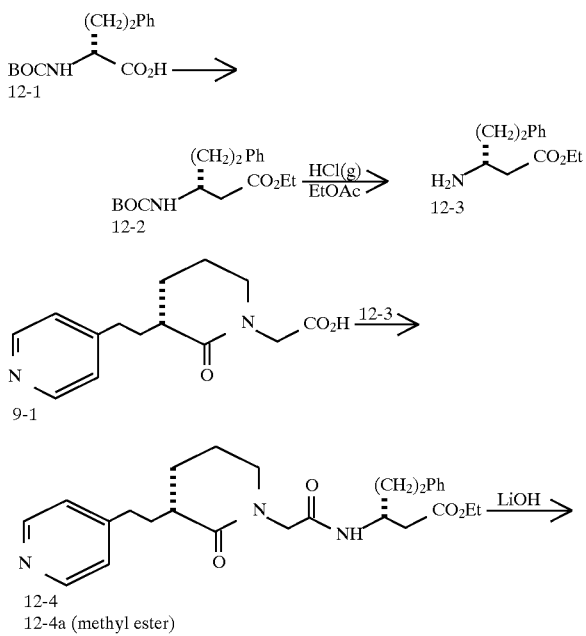

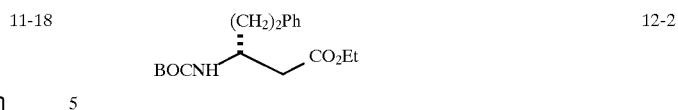

Ethyl N-Boc 3(R)-[2-(phenyl)ethyl]-β-alanine (12-2)

Following procedures substantially similar to those used for 4-4, and substituting with N-BOC-D-homophenylalanine, 12-2 was prepared.

¹H-NMR (300 MHz, CDCl₃) δ7.25 (m, 5H), 6.43 (d, J=7.2 Hz, 1H), 4.23 (m, 1H), 4.05 (q, J=8 Hz, 2H), 2.72 (m, 2H), 2.50 (d,d, J=5, 15 Hz, 1H), 2.43 (d,d, J=15, 7 Hz, 1H), 1.73 (m, 2H), 1.23 (t, J=8 Hz, 3H).

Ethyl 3(R)-[2-(phenyl)ethyl]-β-alanine hydrochloride (12-3)

Treatment of 12-2 in EtOAc with HCl gas at −78° as described for 4-5 gave 12-3.

¹H-NMR (300 MHz, CD₃OD) δ7.25 (m, 5H), 4.15 (q, J=8 Hz, 2H), 3.24 (m, 1H), 2.72 (m, 2H), 2.51 (d,d, J=5,15 Hz, 1H), 2.42 (d,d, J=7.3, 15 Hz, 1H), 1.73 (m, 2H), 1.23 (t, J=8 Hz, 3H).

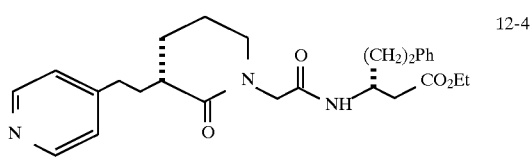

[3(R-(−)-[2-(Pyridin-4-yl)ethyl]-2-piperidon-1-yl)
acetyl-3(R)-[2-(phenyl) ethyl]-β-alanine ethyl ester (12-4)

Pyridine acid 9-1 (320 mg, 1.20 mmol) and, Ethyl 3(R)-[2-(Phenyl) ethyl]-β-alanine hydrochloride 12-3 (300 mg, 1.38 mmol, prepared from N-Boc-D-homophenylalanine by the route previously described for ethyl 3(R)-methyl-β-alanine hydrochloride) were dissolved 4 ml of anhydrous DMF along with HOBT (162 mg, 1.20 mmol), and EDC (230 mg, 1.2 mmol) and Et₃N (176 μl, 1.27 mmol). After stirring at room temperature for 14 h, the reaction mixture was diluted with ethyl acetate (100 ml) and washed successively with H₂O (4×100 ml), sat. NaHCO₃ and brine (100 ml each) then dried over NaSO₄, filtered and evaporated. Flash chromatography of the residue afforded 12-4 as colorless glass.

¹H-NMR (300 MHz, CDCl₃) δ8.46 (d, J=6.0 Hz, 2H), 7.25 (m, 5H), 7.18 (d, J=6.0 Hz, 2H), 6.98 (d, J=8.5 Hz, 1H), 4.30 (m, 1H), 4.16–4.05 (m, 2H), 3.41 (m, 2H), 2.95–2.50 (m, 6H), 2.33 (m, 1H), 2.08–1.83 (m, 5H), 1.20 (t, J=8 Hz, 3H).

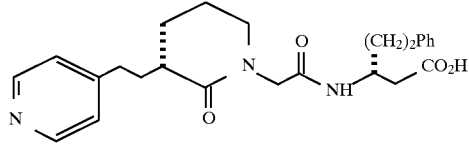

[3(R-(-)-[2-(Pyridin-4-yl)ethyl]-2-piperidon-1-yl)
acetyl-3(R)-[2-(phenyl) ethyl-]-β-alanine
trifluoroacetate (12-5)

12-4 was hydrolyzed with 1N LiOH in aqueous methanol and isolated by preparative reverse phase hplc to afford the acid 12-5 as its TFA salt.

$^1$H-NMR (300 MHz, $D_2O$) δ8.46 (d, J=6.0 Hz, 2H), 7.65 (d, J=6.0 Hz, 2H), 7.15 (m, 5H), 4.04 (m, 1H), 3.82 (d, J=17.1 Hz, 1H), 3.74 (d, J=17.1 Hz, 1H), 3.21 (m, 2H), 2.80 (m, 2H), 2.55–2.26 (m, 4H), 2.33 (m, 1H), 2.08–1.83 (m, 6H).

Following procedures substantially similar to those used for 12-5, the following compounds were prepared.

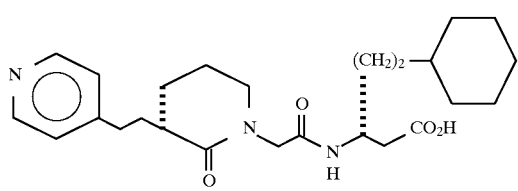

3(R)-[2-(Pyridin-4-yl)ethyl]-2-piperidon-1-yl)]
acetyl-3(R)-[2-(cyclohexyl) ethyl]-β-alanine (12-6)

$^1$H-NMR (300 MHz, $D_2O$) δ8.42 (d, J=6.0 Hz, 2H), 7.65 (d, J=6.0 Hz, 2H), 3.93 (m, 1H), 3.81 (m, 2H), 3.21 (m, 2H), 2.80 (m, 2H), 2.46 (m, 3H), 2.01 (m, 1H), 1.80–1.20 (m, 12H), 1.01 (m, 6H), 6.23 (m, 2H).

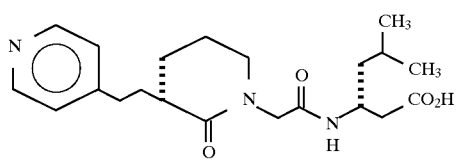

3(R)-[2-(Pyridin-4-yl)ethyl]-2-piperidon-1-yl]acetyl-
3(R)-[2-(methylpropyl]-β-alanine (12-7)

$^1$H-NMR (300 MHz, $D_2O$) δ8.48 (d, J=6 Hz, 2H), 7.76 (d, J=2.6 Hz, 2H), 4.57 (m, 1H), 3.81 (m, 2H), 3.25 (m, 2H), 2.85 (t, J=8.3 Hz, 2H), 2.42 (d,d, J=5, 15 Hz, 1H), 2.23 (m, 3H), 2.00 (m, 1H), 1.83 (m, 2H), 1.61 (m, 2H), 1.43 (m, 2H), 1.18 (m, 1H), 0.73 (m, 6H).

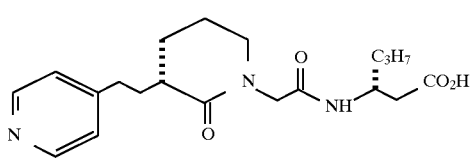

3(R)-[2-(Pyridin-4-yl)ethyl]-2-piperidon-1-yl)acetyl-
3(R)-propyl]-β-alanine 12-8)

$^1$H-NMR (300 MHz, $D_2O$) δ8.45 (d, J=6.3 Hz, 2H), 7.76 (d, J=6.3 Hz, 2H), 4.04 (m, 1H), 3.84 (m, 2H), 3.84 (m, 2H), 3.21 (m, 3H), 2.82 (t, J=7.8 Hz, 2H), 2.41 (d,d, J=5, 5 Hz, 1H), 2.23 (m, 3H), 2.01 (m, 1H), 1.83 (m, 2H), 1.65 (m, 2H), 1.36 (m, 2H), 1.11 (m, 2H), 0.69 (t, J=7.8 Hz, 3H).

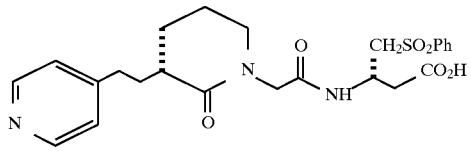

3-[2-(Pyridin-4-yl)ethyl]-2-piperidon-1-yl)acetyl-3-
phenylsulfonylmethyl)-β-alanine (12-9)

1H NMR (300 MHz, DMSO-$d_6$) δ8.72 (d, J=5.8 Hz, 2H), 7.96–7.6 (m, 8H), 4.34 (m, 1H), 3.61 (m, 2H), 3.53 (t, J=2.75 Hz, 2H), 3.15 (m, 2H), 2.85 (t, J=7.5 Hz, 2H), 2.51 (m, 3H), 2.26 (m, 1H), 2.15 (m, 1H), 1.93 (m, 1H), 1.80 (m, 1H), 1.73 (m, H), 1.52 (m, 1H).

SCHEME 13

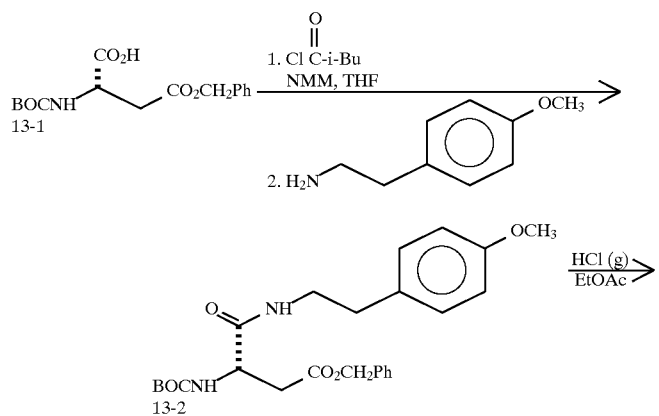

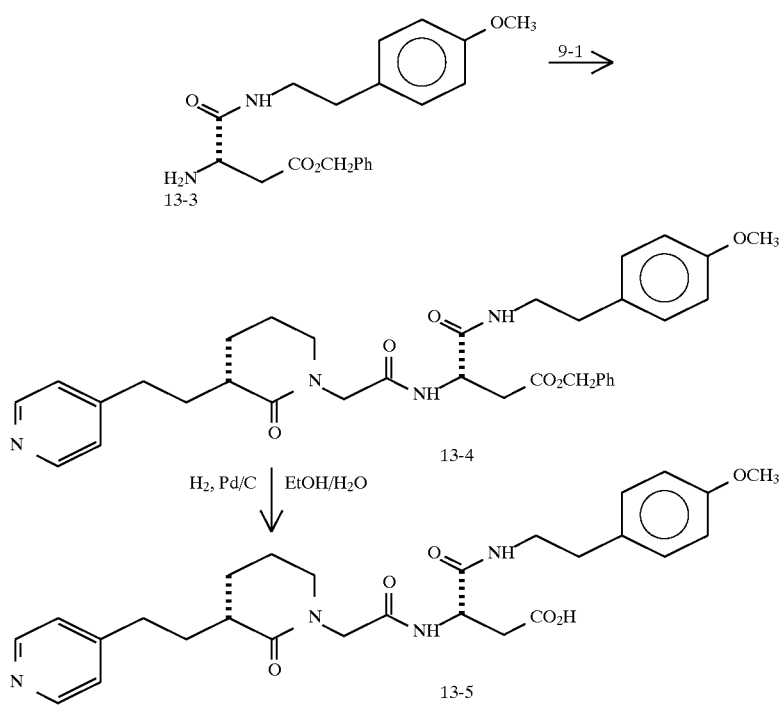

N-Boc-L-Aspartyl-α-[2-(4-methoxyphenyl)ethylamino]-β-benzyl ester (13-2)

Isobutyl chloroformate (1.36 ml, 10 mmol) was added to a −15° solution of commercially available N-Boc-L-aspartic acidβ-benzyl ester (2.33 g, 10 mmol), and NMM (1.08 ml, 0 mmol), in THF (50 ml). The resulting mixture was stirred at −15° for 30 min then a solution of 4-methoxyphenethyl amine (1.51 g, 10 mmol) in 5 ml of THF was added dropwise and the mixture warmed to room temperature. After 2.5 h, the precipitated NMM hydrochloride was removed by filtration and the resulting solution was evaporated. The yellow residue was dissolved in ethyl acetate (100 ml) and washed with 10% $KHSO_4$, sat. $NaHCO_3$, and brine (50 ml each) to give 13-2 which was purified by recrystallization form ethyl acetate/hexanes (1:4).

$^1$H-NMR (300 MHz, $CDCl_3$) δ7.38 (m, 5H), 7.15 (d, J=8.5 Hz, 2H), 6.85 (d, J=8.5 Hz, 2H), 6.53 (t, J=4.9 Hz, 1H), 5.62 (d, J=8 Hz, 1H), 5.15 (m, 2H), 4.48 (m, 2H), 3.81 (s, 3H), 3.51 (m, 2H), 3.18 (d,d J=1.3 Hz, 6 Hz, 1H), 2.79 (t, J=7 Hz, 2H), 2.65 (d,d J=1.9 Hz, 6 Hz, 1H), 1.40 (s, 9H).

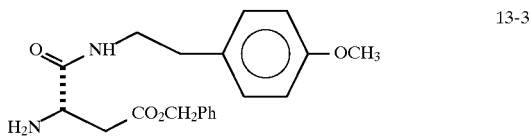

L-Aspartyl-α-[2-(4-methoxyphenyl)ethylamino]-β-benzyl ester (13-3)

A solution of 13-2 in ethyl acetate was deprotected and treated with anydrous HCl gas at 0° to afford 13-3 as its hydrochloride salt.

$^1$H-NMR (300 MHz, DMSO-$d_6$) δ8.61 (t, J=4.9 Hz, 1H), 8.31 (br s, 3H), 7.38 (m, 5H), 7.15 (d, J=8.5 Hz, 2H), 6.83 (d, J=8.5 Hz, 2H), 5.16 (m, 2H), 4.08 (m, 1H), 3.71 (s, 3H), 3.21 (m, 2H), 2.86 (m, 2H), 3.63 (t, J=7.3 Hz, 2H).

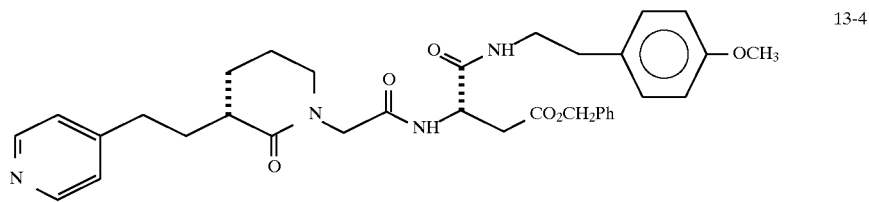

3-(R)-(−)-[2-(Pyridin-4-yl)ethyl]-2-piperidon-1-yl]acetyl-(S)-aspartylα-[2-(4)-methoxyphenyl)ethyl]amide benzyl ester (13-4)

Amine 13-3 was coupled to pyridine acid 9-1 as described for 6-4 to afford 13-4 after chromatography on silica gel (10% $CH_3OH$/ethyl acetate).

¹H-NMR (300 MHz, CDCl₃) δ8.45 (d, J=6 Hz, 2H), 7.38 (m, 5H), 7.31 (d, J=7.0 Hz, 1H), 7.18 (d, J=6 Hz, 2H), 7.14 (d, J=8.5 Hz, 2H), 7.01 (t, J=4.9 Hz, 1H), 6.80 (d, J=8.5 Hz, 2H), 5.15 (d, J=12 Hz, 1H), 5.08 (d, J=12 Hz, 1H), 4.81 (m, 1H), 3.88 (m, 2H), 3.78 (s, 3H), 3.6–3.15 (m, 6H), 2.8–2.6 (m, 6H).

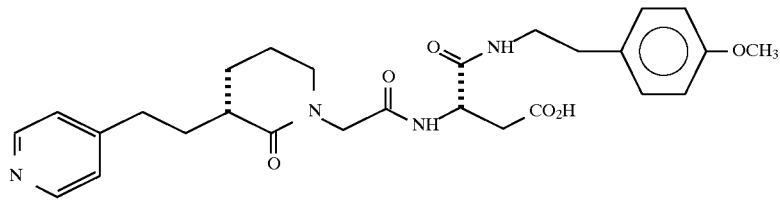

3-(R)-[2-(Pyridin-4-yl)ethyl]-2-piperidon-1-yl] acetyl-aspartyl α-[2-(4) methoxyphenyl)ethyl]amide (13-5)

Benzyl ester 13-4 was dissolved in 50 ml of 50% aqueous ethanol and treated with 10% Pd/C (15 mg). The mixture was stirred under a H₂ atmosphere for 12 h, then filtered through celite and concentrated to give 13-5 as a white crystalline solid. Mp=203°–204°.

¹ H-NMR (300 MHz, D₂O) δ8.45 (d, J=6 Hz, 2H), 7.25 (d, J=6 Hz, 2H), 7.14 (d, J=8.5 Hz, 2H), 6.80 (d, J=8.5 Hz, 2H), 4.36 (m, 1H), 3.88 (m, 2H), 3.76 (s, 3H), 3.5–3.15 (m, 6H), 2.8–2.6 (m, 6H).

Following procedures substantially similar to those used for 13-5, the following compounds were prepared.

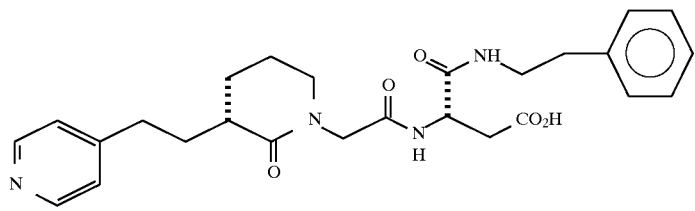

3-(R)-[2-(Pyridin-4-yl)ethyl]-2-piperidon-1-yl] acetyl-aspartyl-α-[2-phenyl)ethyl]amide (13-6)

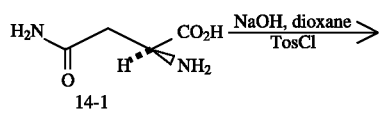

3-(R)-[2-(Pyridin-4-yl)ethyl]-2-piperdinon-1-yl] acetyl-aspartyl-α-[bis-2-phenyl)ethyl]amide (13-7)

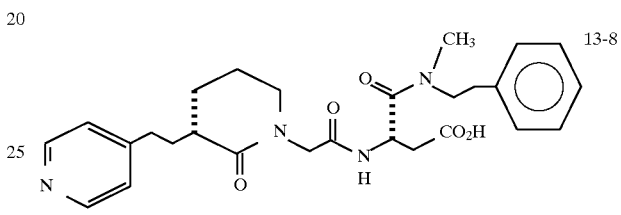

3-(R)-[2-(Pyridin-4-yl)ethyl]-2-piperidon-1-yl] acetyl-aspartyl α-[N-methyl-N-2(phenyl)ethyl] amide (13-8)

SCHEME 14

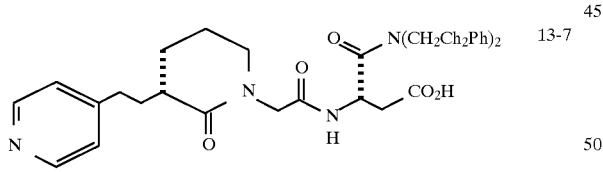

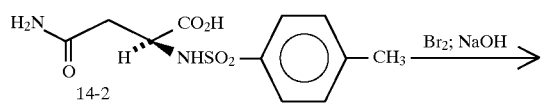

-continued
SCHEME 14
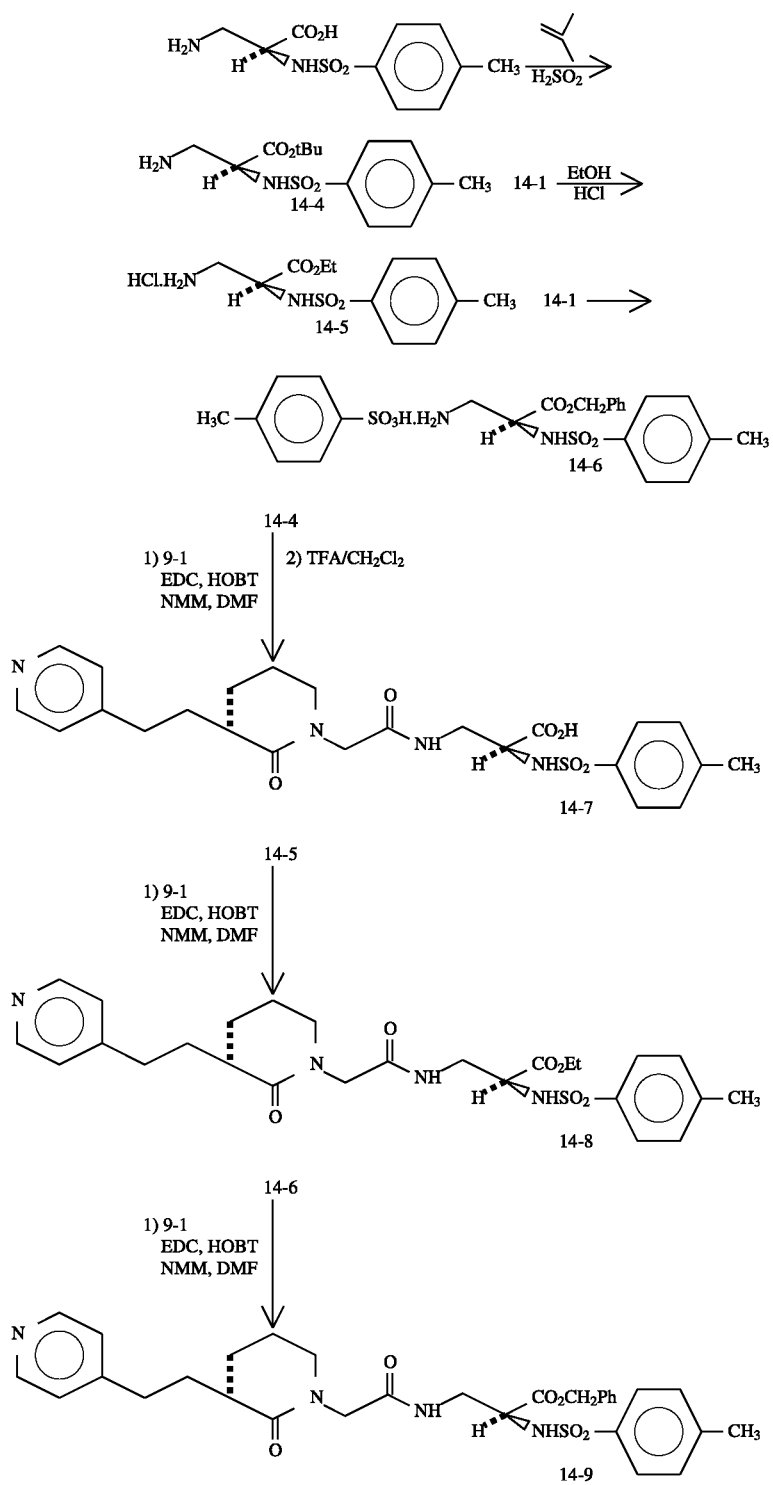
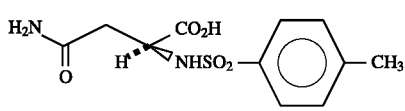
N-p-Toluenesulfonyl-L-asparagine (14-2)
L-Asparagine (10.0 g, 75.7 mmol) was placed in a 500 mL round bottom flask equipped with a magnetic stir bar and an addition funnel. 1N Sodium hydroxide (170 mL, 166.5 mmol) was added along with 50 mL dioxane. p-Toluenesulfonyl chloride (15.88 g, 83.27 mmol) dissolved in dioxane (50 mL) was added to the reaction mixture with vigorous stirring. The reaction mixture was then stirred for 2 h at room temperature, cooled to 0° C., and acidified to pH 2–3 with hydrochloric acid (conc.). The desired product 14-2 formed as a white crystalline solid (20.3 g, 94%) that was collected by filtration.

TLC $R_f$=0.55 (10:0.1 $CH_3OH:NH_4OH$); $^1H$ NMR (DMSO-$d_6$) δ7.91 (d, J=8.79 Hz, 1H), 7.64 (d, 8.06 Hz, 2H), 7.32 (s, d (overlapping), J=8.06 Hz, 3H), 6.87 (s, br, 1H), 4.03 (m, 1H), 3.32 (s, $H_2O$), 2.49 (m, 1H), 2.43 (d, d, J=7.08, 15.38 Hz, 1H), 2.35 (s, 3H), 2.21 (d, d, J=6.11, 15.38 Hz, 1H).

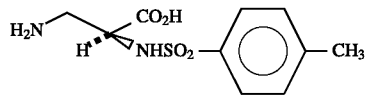

2(S)-(p-Toluenesulfonylamino)-3-aminopropionic acid (14-3)

Bromine (5.03 mL, 97.5 mmol) was added to a chilled solution (−15° C.) of sodium hydroxide (21 g, 525 mmol) in water (300 mL) at such a rate as to keep the temperature below 0° C. The solution was mixed for 10 min, then a cold (0° C.) solution of N-p-toluenesulfonyl-L-asparagine sulfonyl-L-asparagine (14-2) (21.5 g, 75.0 mmol) in 40 mL of 10% NaOH was added in a single portion to the sodium hypobromite solution. This mixture was stirred with cooling for 20 min, then placed in an oil bath and heated at 80°–90° C. for 40 min. The solution was then cooled in an ice bath and adjusted to pH 7 by adding hydrochloric acid (conc.) dropwise. The resulting white solid was isolated by vacuum filtration then dried in a vacuum oven to afford 14-3 (14.2 g, 73.6%.)

TLC $R_f$=0.40 (10:0.1 $CH_3OH:NH_4OH$); $^1H$ NMR (DMSO-$d_6$) δ8.2–7.2 (br, 2H, (NH, COOH)), 7.70 (d, J=8.18 Hz, 2H), 7.38 (8.18 Hz, 2H), 3.7–3.0 (br, 2H, ($NH_2$, $H_2O$)), 3.12 (q, J=4.76 Hz, 1H), 2.99 (d, d, J=4.64, 11.96 Hz, 1H), 2.79 (d, d, J=9.52, 11.96 Hz, 1H), 2.36 (s, 3H).

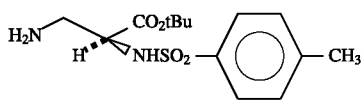

tert.-Butyl 2(S)-(p-toluenesulfonylamino)-3-aminopropionic acid (14-4)

Acid 14-3 (5.0 g, 19.4 mmol) was suspended in dioxane (100 ml) in a 1-L pressure bottle. The bottle was cooled to −15° and isobutylene (100 ml) was condenced into the dioxane. Concentrated $H_2SO_4$ (5 ml) was added and the bottle sealed and stirred at room temperature for 36 h. The bottle was opened and the excess isobutylene carefully vented. The solution was diluted with ethyl acetate (200 ml) and washed with 1N NaOH (200 ml). The organic layer was dried ($Na_2SO_4$), filtered and evaporated to give 14-4 as a white crystaline solid.

$^1H$ NMR (CDCl$_3$) δ7.68 (d, J=8.18 Hz, 2H), 7.35 (J=8.18 Hz, 2H), 3.85 (m, 1H), 2.99 (m, 2H), 2.32 (s, 3H), 1.38 (s, 9H).

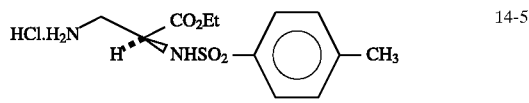

Ethyl 2(S)-(p-toluenesulfonylamino)-3-aminopropionic hydrochloride (14-5)

14-3 (5.0 g, 19.4 mmol) was dissolved in 50 ml anhydrous ethanol. HCl gas was introduced at a rate sufficient to produce a gentle reflux. After 30 min the gas introduction was halted and the solution heated at reflux for 2.5 h, then evaporated and the residue crystalized from ethanol ether to afford 14-5 as a white crystaline solid.

$^1H$ NMR (300 MHz, CD$_3$OD) δ7.71 (d, J=8.1 Hz, 2H), 7.35 (d, J=8.1 Hz, 2H), 4.18 (m, 2H), 3.91 (m, 1H), 2.96 (m, 2H), 2.31 (s, 3H), 0.89 (t, J=7.8 Hz, 3H).

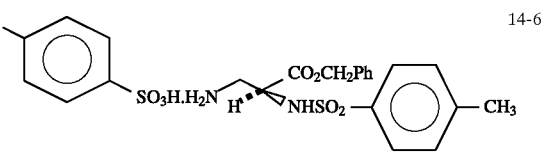

2(S)-(p-Toluenesulfonylamino)-3-aminopropionic acid benzyl ester toluene sulfonate (14-6)

14-3 (5.0 g, 19.4 mmol) was suspended in 150 ml anhydrous benzene along with benzyl alcohol (10 ml, 97 mmol), and p-toluene sulfonic acid mono hydrate (3.87 g, 20.4 mmol). The mixture was refluxed until the theoretical amount of water had collected in a Dean-Stark trap (8.5 h). The resulting solution was cooled and 100 ml anhydrous ether added giving 14-6 as a white solid. $^1H$ NMR (300 MHz, CD$_3$OD) δ7.81 (d, J=8.5 Hz, 2H), 7.71 (d, J=8.5 Hz, 2H), 7.43 (d, J=8.5 Hz, 2H), 7.31 (d, J=8.5 Hz, 2H), 7.28 (m, 5H); 4.98 (m, 2H), 3.91 (m, 1H), 2.89 (m, 2H), 2.35 (s, 3H), 2.31 (s, 2H).

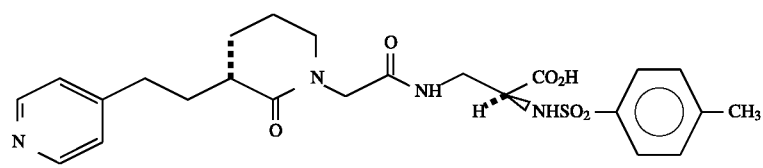

3-(R-(−)-[2-(Pyridin-4-yl)ethyl]-2-piperdinon-1-yl]acetyl-2(S)-(p-toluenesulfonylamino)-3-aminopropionic acid (14-7)

Pyridine acid 9-1 was coupled to amine 14-4 using EDC and HOBt. The product was purified by flash chromatography, then the tert. butyl ester removed by treatment with TFA/CH$_2$Cl$_2$ (1:4). The resulting TFA salt 14-7 was isolated by preparative hplc.

$^1$H NMR (300 MHz, D$_2$O) δ8.45 (d, J=6 Hz, 2H), 7.63 (d, J=7.5 Hz, 2H), 7.14 (d, J=7.5 Hz, 2H), 7.18 (d, J=6Hz, 2H), 4.15 (d, J=17 Hz, 1H 3.95 (d, J=17 Hz, 1H), 3.86 (m, 1H), 3.6–3.2 (m, 6H), 2.8 (m, 2H), 2.4–2.28 (m, 2H), 2.27 (s, 3H), 2.1–1.8 (m, 6H).

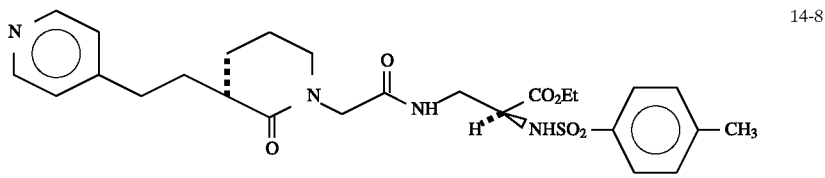

14-8

Ethyl-3-(R)-(−)-[2-(pyridin-4-yl)ethyl]-2-piperdinon-1-yl]acetyl-2(S)-(p-toluene sulfonylamino)-3-aminopropionic acid (14-8)

Prepared from 9-1 and 14-5 as described per 14-7.

$^1$H NMR (300 MHz, D$_2$O) δ8.44 (d, J=6.3Hz, 2H), 7.76 (d, J=6.3 Hz, 2H), 7.53 (d, J=7.5 Hz, 2H), 7.25 (d, J=7.5 Hz, 2H), 3.95 (t, J=6.8 Hz, 1H), 3.76 (m, 2H), 3.63 (m, 2H), 3.40 (d,d, J=4,14 Hz, 1H), 3.25 (d,d, J=5, 14 Hz, 1H), 3.15 (m, 2H), 2.83 (t, J=7.6 Hz, 2H), 2.30 (m, 1H), 2.23 (s, 3H), 2.01 (m, 1H), 1.9–1.48 (m, 5H), 0.85 (t, J=7.5 Hz, 3H).

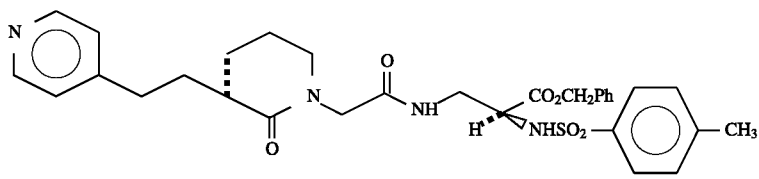

14-9

3-(R)-(−)-[2-(Pyridin-4-yl)ethyl]-2-piperon-1-yl] acetate-2(S)-(p-toluenesulfonylamino)-3-aminopropionic acid benzyl ester (14-9)

Prepared from 9-1 and 14-6 as described above.

$^1$H NMR (300 MHz, D$_2$O) δ8.38 (d, J=6.3 Hz, 2H), 7.68 (d, J=6.3 Hz, 2H), 7.48 (d, 7.5 Hz, 2H), 7.28 (m, 7H), 4.89 (m, 2H), 3.95 (m, 1H), 3.78 (m, 2H), 3.63 (m, 2H), 3.40 (m, 1N), 3.35 (m, 1H), 3.15 (m, 2H), 2.83 (m, 2H), 2.28 (m, 1H), 2.21 (s, 2H), 2.01 (m, 1H), 1.83–1.5 (m, 5H).

SCHEME 15

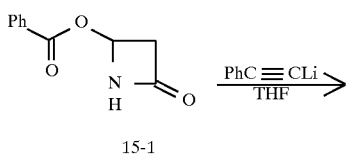

-continued
SCHEME 15

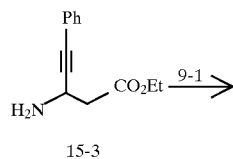

-continued
SCHEME 15

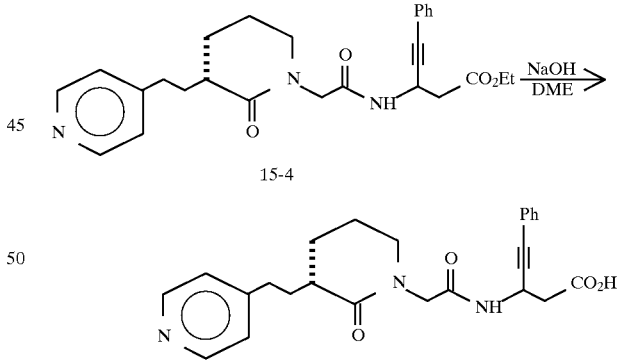

3(R,S)-Phenylethynylazetidinone (15-2)

To a 500 mL, three necked round bottomed flask with a stirring bar, low temperature thermometer, argon inlet and a septum was added dry THF (100 mL) and ethynylbenzene (60 mmol, 6.1 mL). This solution was cooled to −78° C. and n-butyllithium (60 mmol, 24 mL of a 2.5M solution in hexane) was added with a syringe at such a rate that the temperature was maintained below −50° C. When the addition was complete, the solution was aged 30 min then a solution of 3(R,S)-benzoylazetidinone (15 mmol, 2.87 g) in THF (50 mL) was added slowly with a syringe, maintaining the temperature below −60° C. The resulting solution was aged 1 h at −78° C. then warmed to 0°C. The reaction was quenched at 0°C. by addition of saturated, aqueous NH$_4$Cl solution. The mixture was diluted with EtOAc and the layers were separated. The organic phase was washed with H$_2$O and brine. Drying (MgSO4), filtration and removal of the solvents in vacuo gave 3(R,S)-phenylethynylazetidinone (15-2) as a crystalline solid, which was used in Step B without further purification.

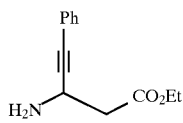

Ethyl 3-amino-5-phenyl-4-pentynoate (15-3)

To a 25 mL round bottomed flask equipped with a stirring bar and a stopper was added 3-phenylethynylazetidinone (15-2) (10.5 mmol, 1.80 g) and ethanolic HCl (100 mL of a 2.5M solution). This solution was stirred at ambient temperature for 18 h. The ethanolic HCl was removed in vacuo and the residue was dissolved in a minimal amount of H$_2$O. This solution was made basic with NaHCO$_3$ solution and extracted with EtOAc. The combined EtOAc extracts were washed with brine, dried (Na$_2$SO$_4$), filtered, and concentrated in vacuo. The residue was chromatographed on silica gel (100 g) using ammonia saturated CHCl$_3$ as eluant to afford 15-3.

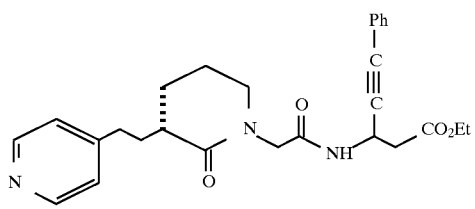

Ethyl 3(R,S)-[3(R)-[2-(pyridin-4-yl)ethyl]-2-piperidone-1-yl]acetamido-3-phenylethynylpropanoate (15-4)

To a 100 mL round bottomed flask equipped with a stirring bar and an argon inlet was added ethyl 3(R,S)-amino-5-phenyl-4-pentynoate (10.2 mmol, 2.22 g), N-[3(R)-[2-pyridin-4-yl)ethyl]-2-piperidon-1-yl]acetic acid (9-1) (10.2 mmol, 2.68 g) ethyl-3-(N,N-dimethylamino) propyl-carbodiimide hydrochloride (10.2 mmol, 2.04 g), N-hydroxy-benzotriazole hydrate (10.2 mmol, 1.44 g) and DMF (15 mL). When all of the solids had dissolved, triethylamine (20.0 mmol, 2.79 mL) was added. The resulting mixture was stirred at ambient temperature for 18.5 h. The DMF was removed in vacuo and the residue was dissolved in EtOAc (200 mL). This solution was washed with aqueous NaHCO$_3$ solution, H$_2$O and brine. Drying (MgSO$_4$), filtration, and removal of the solvent in vacuo, gave 4.3 g of an oil. This material was chromatographed on silica gel (100 g) using 5% 2-propanol in CHCl$_3$ as eluant to give 15-4 as an oil.

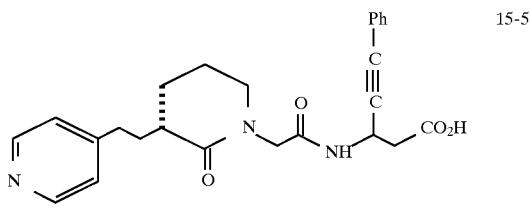

3(R,S)-[3(R)-[2-(Pyridin-4-yl)ethyl]-2-piperidone-1-yl]acetamido-3-phenylethynylpropanoic acid (15-5)

To a 200 mL round bottomed flask equipped with an argon inlet and a stirring bar was added ethyl 3(R,S)-[3(R)-[2-(pyridin-4-yl)ethyl]-2-piperidone-1-yl]acetamido-3-phenylethynylpropanoate (15-4) (8.23 mmol, 3.80 g), DME (60 mL), and aqueous sodium hydroxide (30 mmol, 30 mL of a 1N solution). This mixture was stirred at ambient temperature for 24 h. The reaction was neutralized with 1N HCl and the solvents were removed in vacuo. The residue was triturated with a 1:1 mixture of hot CH$_3$CN/acetone and filtered, The filtrate was concentrated in vacuo. This residue was chromatographed on silica gel (100 g) using 12:10:1:1 EtOAc:EtOH:H$_2$O:NH$_4$OH as eluant to give 15-5 as the ammonium salt.

$^1$H NMR (DMSO-d$_6$) δ1.55 (m, 1H), 1.70 (m, 2H), 1.78 (m, 1H), 1.82 (m, 1H), 2.08 (m, 1H) 2.23 (m, 1H), 2.50 (m, 1H), 2.54 (m, 2H), 2.65 (m, 2H), 3.27 (m, 2H), 3.91 (ab Q, 2H, J=12, 16 Hz), 5.09 (m, 1H), 6.70 (br s, 1H), 7.22 (d, 2H, J=6 Hz), 7.35 (s, 5H), 8.50 (d, 2H, J=6 Hz), 8.66 (br d, 1H, J=8 Hz).

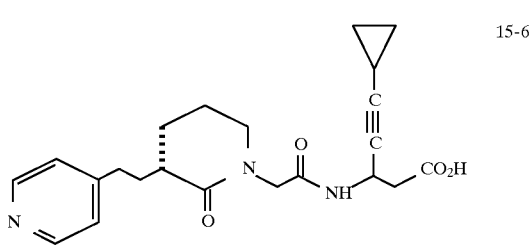

3(R,S)-[3(R)-[2-(Pyridin-4-yl)ethyl]-2-piperidone-1-yl]acetamido-3-cyclopropylethynylpropanoic acid (15-6)

In manner similar to that described for 15-5, substituting ethynylcyclopropane for ethynylbenzene, 3(R,S)-[3(R)-[2-(pyridin-4-yl)ethyl]-2-piperidone-1-yl]acetamido-3-cyclopropylethynylpropanoic acid 15-6 was prepared.

$^1$H NMR (D$_2$O) δ0.48 (m, 2H), 0.62 (m, 2H), 1.08 (m, 1H), 1.61 (m, 2H), 1.83 (m, 2H), 2.03 (m, 2H), 2.34 (m, 1H), 2.62 (d, 2H, J=6.7 Hz), 2.87 (t, 2H, J=8.1 Hz), 3.22 (m, 2H), 3.86 (m, 2H), 4.75 (t, 1H, J=6.6 Hz, 7.80 (d, 2H, J=6 Hz), 8.48 (d, 2H, J=6 Hz).

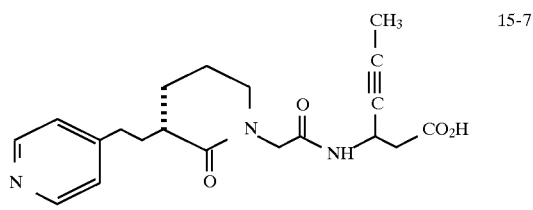

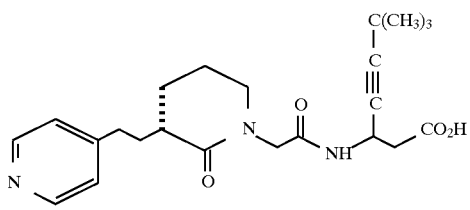

3(R,S)-[3(R)-[2-(Pyridin-4-yl)ethyl]-2-piperidone-1-yl]acetamido-3-(1-propynyl)propanoic acid (15-7)

3(R,S)-[3(R)-[2-(Pyridin-4-yl)ethyl]-2-piperidone-1-yl]acetamido-3-(3,3,-dimethyl-1-butynyl)propanoic acid (15-8)

In manner similar to that described for 15-5, substituting propyne for ethynylbenzene 3(R,S)-[3(R)-[2-(pyridin-4-yl)ethyl]-2-piperidone- 1-yl]acetamido-3-(1-propynyl)propanoic acid 15-7 was prepared.

In manner similar to that described for 15-5, substituting 3,3-dimethyl-1-butyne for ethynylbenzene 3(R,S)-[3(R)-[2-(pyridin-4-yl)ethyl]-2-piperidone-1-yl]acetamido-3-(3,3-dimethyl-1-butynyl)-propanoic acid (15-8) was prepared.

$^1$H NMR (D$_2$O) δ1.59–1.75 (m, 5H), 1.90 (m, 3H), 2.08 (m, 1H), 2.40 (m, 1H), 2.69 (d, 2H, J=6.6 Hz), 2.93 (t, 2H, J=8.1 Hz), 3.31 (m, 2H), 3.93 (m, 2H), 4.81 (m, 1H), 7.85 (d, 2H, J=6.6 Hz), 8.54 (m, 2H).

$^1$H NMR (D$_2$O) δ1.07 (m, 9H), 1.69 (m, 2H), 1.89 (m, 3H), 2.09 (m, 1H), 2.40 (br s, 1H), 2.68 (m, 2H), 2.92 (m, 2H), 3.30 (m, 2H), 3.92 (m, 2H), 4.83 (t, 1H, J=6.6 Hz), 7.85 (m, 2H), 8.54 (m, 2H).

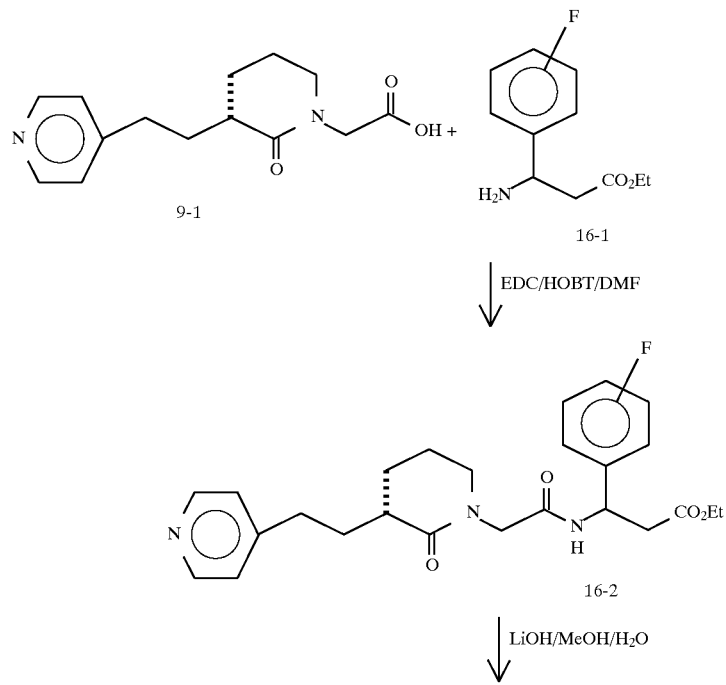

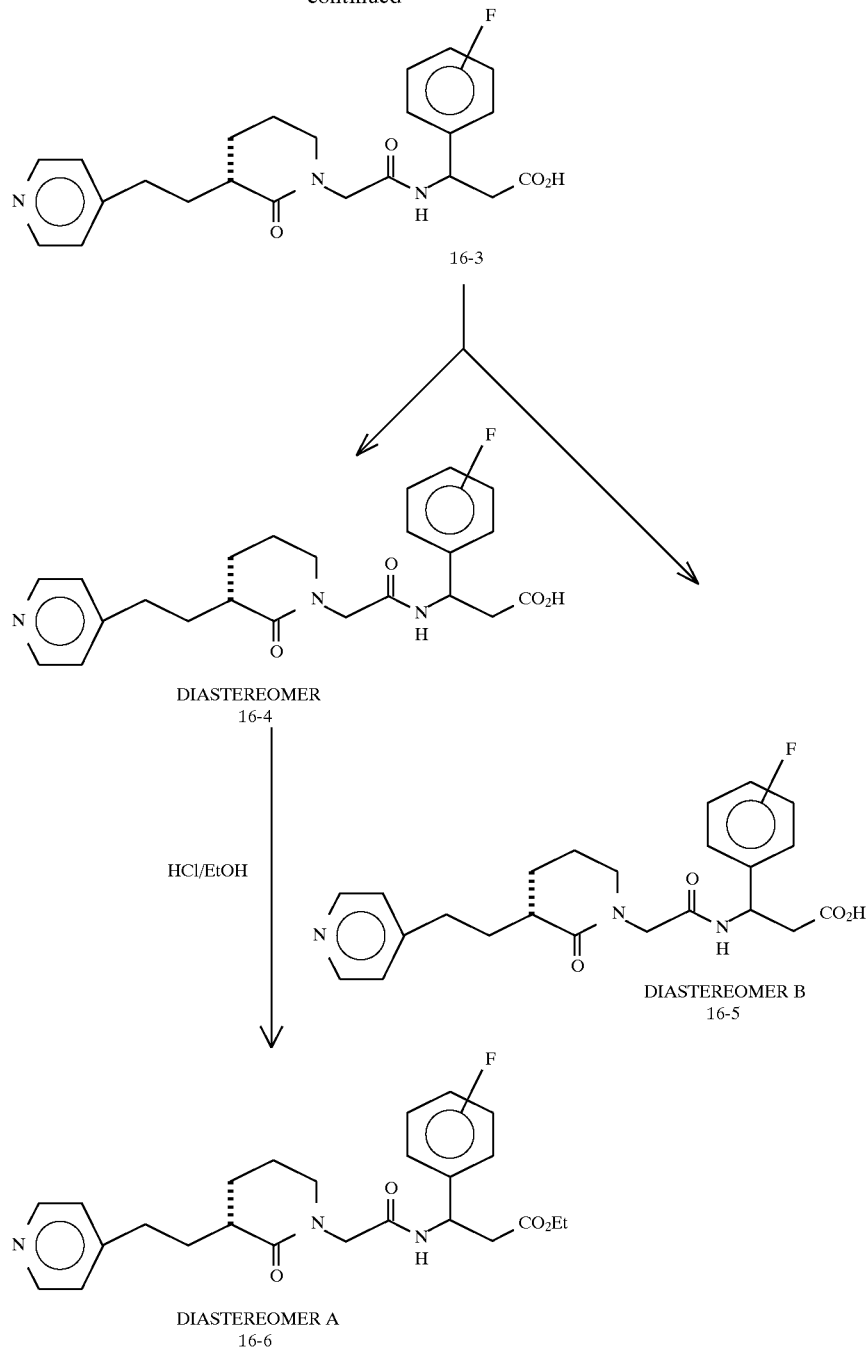

3(R,S)-(2-Fluorophenyl)-β-alanine ethyl ester hydrochloride (16-1a)

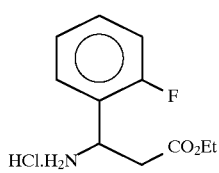

Malonic acid (1.45 g, 13.9 mmol) was dissolved in absolute EtOH (50 mL) and NH$_4$OAc (1.21 g, 15.7 mmol) was added. After 5 minutes at room temperature, 2-fluorobenzaldehyde (1.5 g, 12.1 mmol) was added and the mixture heated to reflux for 18 hours under argon. The solution was cooled and the precipitate was collected by vacuum filtration, washed with EtOH and air dried to give a white powder. HCl gas was bubbled through a solution of the precipitate in EtOH for 5 minutes then the mixture was stoppered for 1 hour. Removal of the solvent afforded the title compound as a white solid.

$^1$H NMR (CD$_3$OD) δ7.60 (t, 1H), 7.50 (m, 1H), 7.25 (m, 2H), 5.00 (t, 1H), 4.15 (q, 2H), 3.15 (m, 2H), 1.20 (t, 3H).

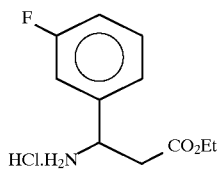

3(R,S)-(3-Fluorophenyl)-β-alanine ethyl ester hydrochloride (16-1b)

Following the procedure described for Example 16-1a, but using 3-fluorobenzaldehyde as starting material, the title compound was obtained as a solid.

¹H NMR δ7.50 (m, 1H), 7.25 (m, 3H), 4.75 (t, 1H), 4.15 (q, 2H), 3.05 (m, 2H), 1.20 (t, 3H).

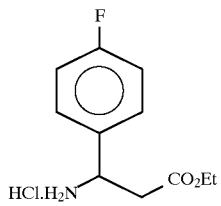

3(R,S)-(4-Fluorophenyl)-β-alanine ethyl ester hydrochloride (16-1c)

Following the procedure described for Example 16-1a, but using 4-fluorobenzaldehyde as staring material, the title compound was obtained as a solid.

¹H NMR δ7.50 (m, 2H), 7.20 (t, 2H), 4.75 (t, 1H), 4.15 (q, 2H), 3.05 (m, 2H), 1.20 (t, 3H).

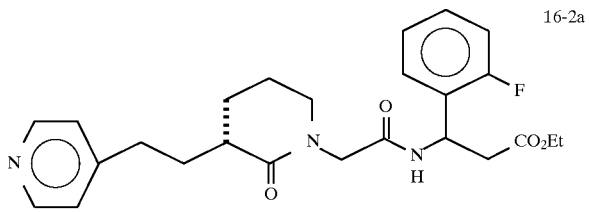

N-[3(R)-[2-(4-Pyridyl)ethyl]-2-piperidone-1-yl]acetyl-3(R,S)-(2-fluorophenyl)-β-alanine ethyl ester (16-2a)

3(R)-[2-(4-Pyridyl)ethyl]-2-piperidone-1-yl]acetic acid (9-1) and 3(R,S)-(2-fluorophenyl)-β-alanine ethyl ester hydrochloride (16-1a) were coupled using standard peptide procedures (EDC/HOBT) to afford the title compound as the trifluoroacetate salt after purification by reverse phase HPLC (Delta-Pak™ C-18 column; ACN/H₂O+0.1% TFA gradient) and lyophilization.

Analysis calculated for $C_{25}H_{30}N_3O_4F_1$.2.25 TFA.0.20 $H_2O$ C, 49.51; H, 4.60; N, 5.87 Found: C, 49.49; H, 4.57; N, 6.00

FAB MS m/z 456 (M+1)

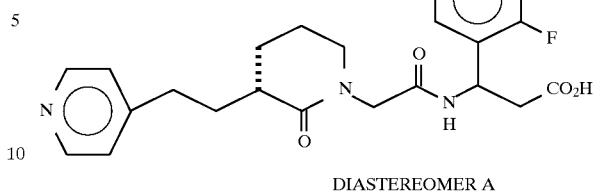

DIASTEREOMER A

N-[3(R)-[2-(4-Pyridyl)ethyl]-2-piperidone-1-yl]acetyl-3-(2-fluorophenyl)-β-alanine: Diastereomer A (16-4a)

The ester 16-2a was hydrolyzed using aqueous LiOH in methanol and the solvent then removed. Purification of the crude product using reverse phase HPLC (Delta-Pak™ C18 column; ACN/H₂O+0.1% TFA gradient) and collecting the first eluted material afforded the title compound as the trifluoroacetate salt after lyophilization.

Analysis calculated for $C_{23}H_{26}N_3O_4F_1$.1.75 TFA.0.40 $H_2O$ C, 50.19; H, 4.54; N, 6.63 Found: C, 50.17; H, 4.50; N, 6.90

FAB MS m/z 428 (m+1)

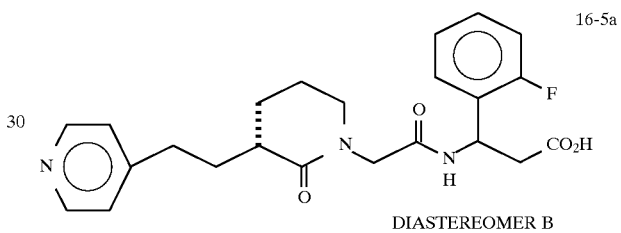

DIASTEREOMER B

N-[3(R)-[2-(1-Pyridyl)ethyl-2-piperidone-1-yl] acetyl-3-(2-fluorophenyl)-β-alanine: Diastereomer B (16-5a)

The ester 16-2a was hydrolysed using aqueous LiOH in methanol and the solvent was then removed. Purification of the crude product using reverse phase HPLC (Delta-Pak™ C-18 column; ACN/H₂O+0.1% TFA gradient) and collecting the second eluted material afforded the title compound as the trifluoroacetate salt after lyophilisation.

Analysis calculated for $C_{23}H_{26}N_3O_4F_1$.1.80 TFA C, 50.50; H, 4.43; N, 6.64 Found: C, 50.49; H, 4:40; N, 6.87

FAB MS m/z 428 (M+1)

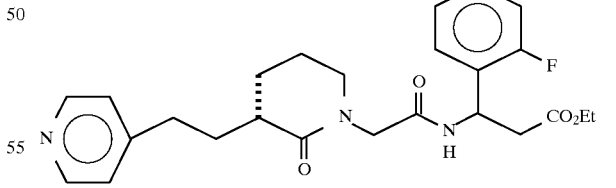

DIASTEREOMER A

N-[3(R)-[2-(4-Pyridyl)ethyl]-2-piperidone-1-yl] acetyl-3-(2-fluoro-phenyl-β-alanine ethyl ester: Diastereomer A (16-6a)

The acid 16-4a was dissolved in absolute EtOH and HCl gas was bubbled through the solution for 5 minutes. The solvent was then removed. Purification of the crude product using reverse phase HPLC (Delta-Pak™ C-18 column; ACN/H₂O+0.1% TFA gradient) afforded the title compound as the trifluoroacetate salt after lyophilization.

¹H NMR δ8.68 (d, 2H), 7.93 (d, 2H), 7.40 (t, 1H), 7.30 (m, 1H), 7.15 (m, 2H), 5.60 (t, 1H), 4.19 (d, 1H), 4.08 (q, 2H), 3.91 (d, 2H), 3.45 (m, ¹H), 3.35 (m, 1H), 3.00 (m, 2H), 2.84 (d, 2H), 2.45 (m, 1H), 1.96 (m, 6H), 1.18 (t, 3H).

Analysis calculated for C₂₅H₃₀N₃O₄F₁.1.62 TFA .1.10 H₂O C, 51.39; H, 5.16; N, 6.37 Found: C, 51.39; H, 5.16; N, 6.38

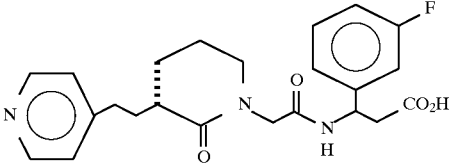

DIASTEREOMER A

N-[3(R)-[2-(4-Pyridyl)ethyl)-2-piperidone-1-yl] acetyl-3-(3-fluorophenyl)-β-alanine: Diastereomer A (16-4b)

3(R)-[2-(4-Pyridyl)ethyl]-2-piperidone-1-yl)]acetic acid (9-1) and 3(R,S)-(3-fluorophenyl)-β-alanine ethyl ester hydrochloride (16-1b) were coupled using standard peptide procedures (EDC/HOBT). The ethyl ester product was hydrolysed and purified using the procedure of 16-4a to give the title compound as the trifluoroacetate salt.

Analysis calculated for C₂₃H₂₆N₃O₄F₁.1.90 TFA.1.05 H₂O C, 48.55; H, 4.56; N, 6.34 Found: C, 48.54; H, 4.51; N, 6.55

FAB MS m/z 428 (M+1).

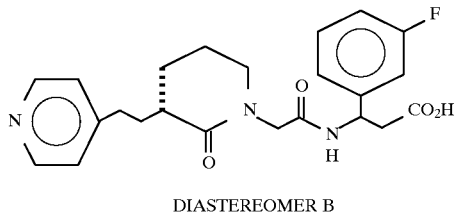

DIASTEREOMER B

N-[3(R)-[2-(4-Pyridyl)ethyl)-2-piperidone-1-yl] acetyl-3-(3-fluorophenyl)-β-alanine: Diastereomer B (16-5b)

3(R)-[2-(4-Pyridyl)ethyl]-2-piperidone-1-yl]acetic acid (2-1) and 3(R,S)-(3-fluorophenyl)-β-alanine ethyl ester hydrochloride were coupled using standard peptide procedures (EDC/HOBT). The ethyl ester product was hydrolyzed and purified using the procedure of 16-5a to give the title compound as the trifluoroacetate salt.

Analysis calculated for C₂₃H₂₆N₃O₄F₁.1.75 TFA.0.85 H₂O C, 49.55; H, 4.62; N, 6.54 Found: C, 49.54; H, 4.64; N, 6.85

FAB MS m/z 428 (M+1)

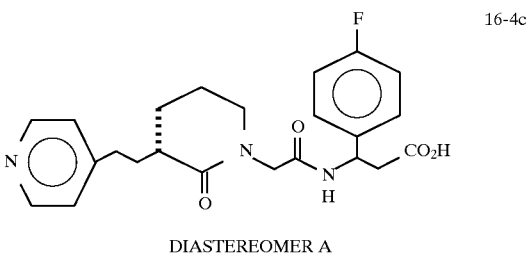

DIASTEREOMER A

N-[3(R)-[2-(4-Pyridyl)ethyl)-2-piperidone-1-yl] acetyl-3-(4-fluorophenyl)-β-alanine: Diastereomer A (16-4c)

3(R)-[2-(4-Pyridyl)ethyl]-2-piperidone-1-yl]acetic acid (9-1) and 3(R,S)-(4-fluorophenyl)-β-alanine ethyl ester hydrochloride 16-1c were coupled using standard peptide procedures (EDC/HOBT). The ethyl ester product was hydrolysed and purified using the procedure of 16-4a to give the title compound as the trifluoroacetate salt.

Analysis calculated for C₂₃H₂₆N₃O₄F₁.1.60 TFA.0.75 H₂O C, 50.48; H, 4.71; N, 6.74 Found: C, 50.46; H, 4.66; N, 6.85

FAB MS m/z 428 (M+1)

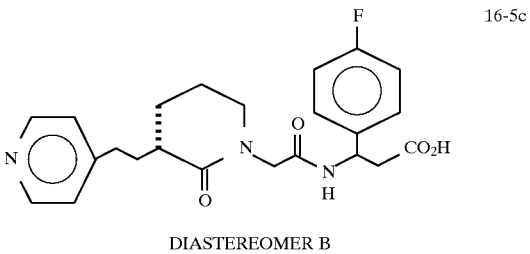

DIASTEREOMER B

N-[3(R)-[2-(4-Pyridyl)ethyl)-2-piperidone-1-yl] acetyl-3-(4-fluorophenyl)-β-alanine: Diastereomer B (16-5c)

3(R)-[2-(4-Pyridyl)ethyl]-2-piperidone-1-yl]acetic acid (9-1) and 3(R,S)-(4-fluorophenyl)-β-alanine ethyl ester hydrochloride were coupled using standard peptide procedures (EDC/HOBT). The ethyl ester product was hydrolyzed and purified using the procedure of 16-5a to give the title compound as the trifluoroacetate salt.

Analysis calculated for C₂₃H₂₆N₃O₄F₁.1.55 TFA.1.50 H₂O C, 49.66; H, 4.88; N, 6.66 Found: C, 49.59; H, 4.52; N, 7.05 FAB MS m/z 428 (M+1)

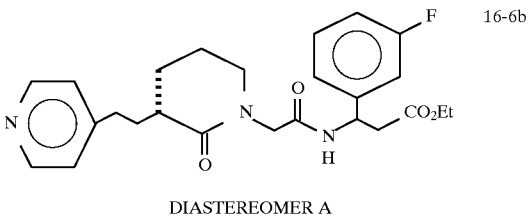

DIASTEREOMER A

N-[3(R)-[2-(4-Pyridyl)ethyl)-2-piperidone-1-yl] acetyl-3-(3-fluorophenyl)-β-alanine ethyl ester: Diastereomer A (16-6b)

Following the procedure of 16-6a, the acid of Example 16-4b was converted into the title compound.

Analysis calculated for $C_{25}H_{30}N_3O_4F_1 \cdot 2.20$ TFA$\cdot 1.25$ CH$_3$CN C, 50.57; H, 4.78; N, 7.86 Found: C, 50.58; H, 5.02; N, 7.88

FAB MS m/z 456 (M+1)

SCHEME 17

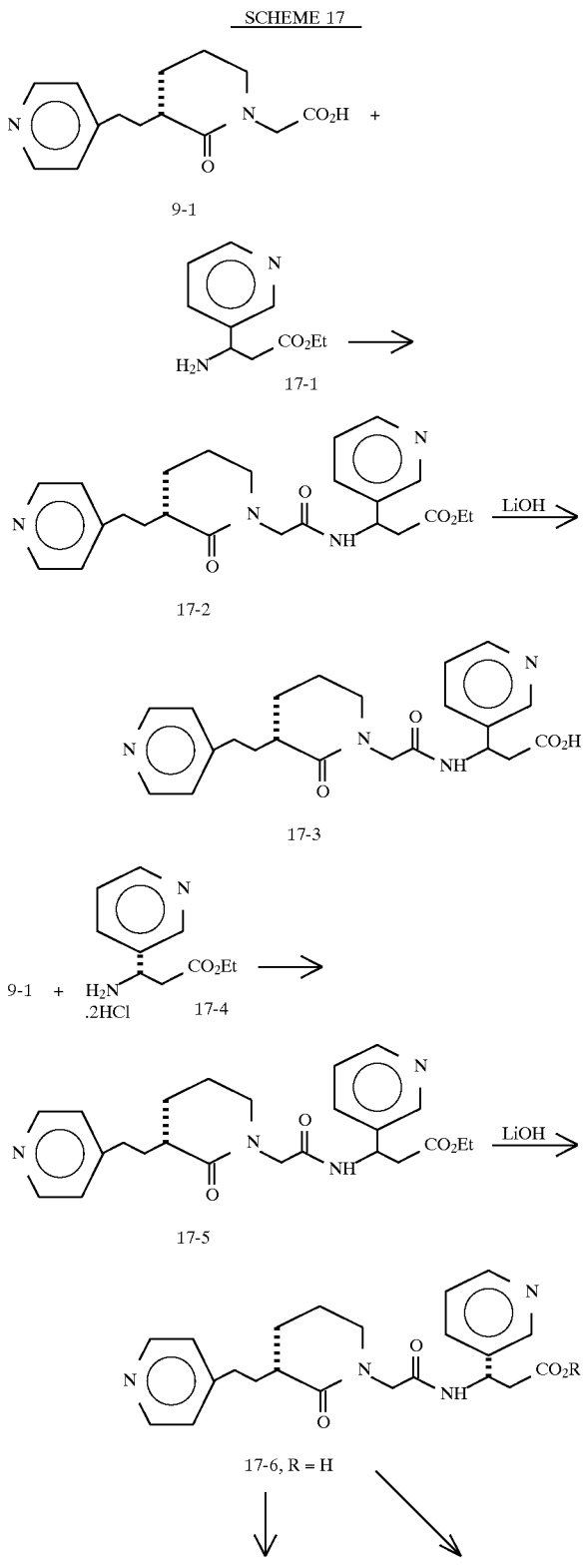

-continued
SCHEME 17

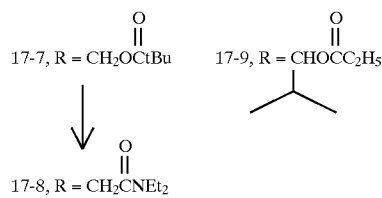

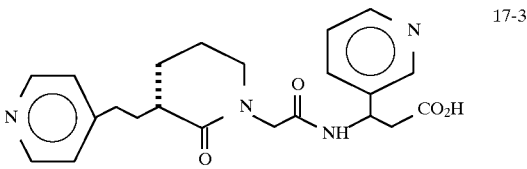

N-[3(R)-[2-(4-Pyridyl)ethyl]-2-piperidone-1-yl] acetyl-3(R,S)-(3-pyridyl)-β-alanine ethyl ester dihydrochloride (17-2)

To a stirred solution of 9-1 (0.393 g, 1.5 mmole), 17-1 (0.401 g, 1.5 mmole), and HOBT (0.228 g, 1.65 mmole), in dry DMF (20 ml) was added NMM (0.607 g, 6 mmole) and EDC (0.345 g, 1.8 mmole). After 24 hrs. of stirring, the solvent was removed, the residue taken up in H$_2$O (25 ml) and extracted with EtOAc. The organic layer was washed with saturated NaHCO$_3$, brine, dried (Na$_2$SO$_4$), concentrated and the residue purified by reverse phase HPLC (Delta-Pak™ C-18 column; CH$_3$CN/H$_2$O to 1% TFA gradient). Further treatment with ion-exchange resin (Bio-Rad AG 3-X4 resin, Cl$^{31}$ form) and lyophilization provided the desired ethyl ester dihydrochloride (17-2).

Analysis calculated for $C_{24}H_{30}N_4O_4+2HCl+H_2O+1/4$ EtOAc C, 54.44; H, 6.58; N, 10.16 Found: C, 54.35; H, 6.47; N, 9.90

$^1$H NMR (300 MHz, D$_2$O) δ0.92–1.12 (3H, m), 1.44–2.06 (6H, m), 2.20–2.35 (1H, m), 2.72–2.98 (4H, m), 3.09–3.65 (3H, m), 3.80–4.06 (4$^+$H, m), 5.28–5.39 (1H, m), 7.66–7.90 (3H, m), 8.34–8.68 (5H, m).

N-[3(R)-[2-(4-Pyridyl)ethyl]-2-piperidone-1-yl] acetyl-3(R,S)-3-pyridyl)-β-alanine (17-3)

The free base of 17-2 (1.2 mmole) was treated with LiOH·H$_2$O (0.151 g, 3.6 mmole) in THF/MeOH/H$_2$O (1:1:1) (20 ml) for 24 hrs. The solvent was removed and the residue was dissolved in H$_2$O and this was purified by reverse phase HPLC (Delta-Pak™ C-18 column; CH$_3$CN/ H$_2$O+0.1% TFA gradient). Lyophilization provided the bis-TFA salt of the title compound.

Analysis calculated for $C_{22}H_{26}N_4O_4+2.5$ CF$_3$COOH C, 46.62; H, 4.13; N, 8.06 Found: C, 26.25; H, 4.20; N, 8.44

$^1$H NMR (300 MHz, CD30D) 6 1.66–2.18 (6H, m), 2.36–2.52 (1H, m), 2.90–3.12 (4H, m), 3.32–3.54 (2H, m), 3.92–4.20 (2H, m), 5.38–5.52 (1H, m), 7.90–8.07 (3H, m), 8.54–8.64 (1H, d), 8.66–8.80 (3H, m), 8.90 (1H, s).

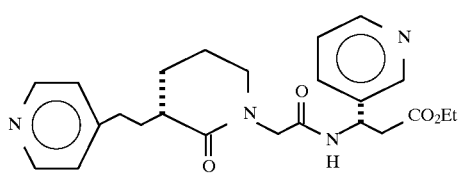

N-[3-R-[2-(4-Pyridyl)ethyl]-2-piperidone-1-yl]acetyl-3(S)-(3-pyridyl)-β-alanine ethyl ester (17-5)

The title compound 17-5 was prepared in a similar fashion to 17-2 starting with 3(S)-(3-Pyridyl)-β-alanine ethyl ester dihydrochloride. 17-4 (Rico et al., *J. Org. Chem.,* 1993, 58, 7648) FAB MS m/z 439 (M+1).

$^1$H NMR (dihydrochloride) (300 MHz, $CD_3OD$) δ1.17–1.29 (3H, t), 1.64–2.28 (6H, m) 2.45–2.52 (1H, m), 2.95–3.10 (4H, m) 3.30–3.54 (2H, m), 3.92–4.22 (4H, m), 5.40–5.54 (1H, m), 7.94–8.12 (3H, m), 8.64–8.96 (5H, m).

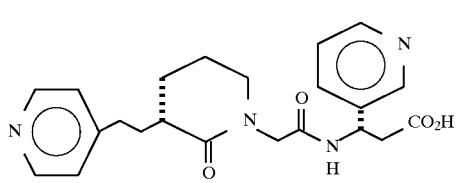

N-[3(R)-[2-(4-Pyridyl)ethyl]-2-piperidone-1-yl]acetyl-3(S)-(3-pyridyl)-β-alanine (17-6)

The compound was prepared in a similar fashion to 17-3 and was purified by reverse phase HPLC (Delta-Pak™ C-18 column; $CH_3CN/H_2O$ to 0.1% TFA gradient) and lyophilization to provide the bis-TFA salt 17-6.

Analysis calculated for $C_{22}H_{26}N_4O_4$+2.5 $CF_3COOH$ +$H_2O$ C, 45.45; H, 4.31; N, 7.85 Found: C, 45.59; H, 4.03; N, 7.81

$^1$H NMR (300 MHz, $CD_3OD$) δ1.65–2.26 (6H, m), 2.38–2.52 (1H, m), 2.92–3.09 (4H, m), 3.30–3.54 (2H, m), 3.90–4.21 (2H, dd), 5.38–5.55 (1H, m), 7.90–8.09 (3H), 8.52–8.60 (1H, d), 8.66–8.91 (4H, m).

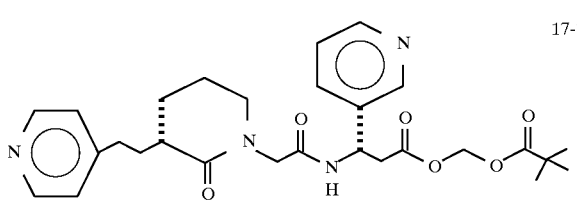

N-[3(R)-[2-(4-Pyridyl)ethyl]-2-piperidone-1-yl]acetyl-3(S)-(3-pyridyl)-β-alanine pivaloyloxymethyl ester (17-7)

To a solution of 17-6 dihydrochloride (0.100 g, 0.207 mmole) in dried DMF (5 ml) is added Cs2CO3 (0.130 g, 0.4 mmole). The resulting mixture was stirred at r.t. for 5 min, chloromethyl pivaloate (0.151 g, 1.0 mmole) was added dropwise and the mixture was stirred for an additional hour at r.t. The reaction was then diluted with $H_2O$ (25 ml) and extracted with EtOAc. The organic layer was washed with brine, dried ($Na_2SO_4$), concentrated and the residue purified by reverse phase HPLC (Delta-Pak™ C-18 column; $CH_3CN/H_2O$+0.1% TFA gradient) and lyophilization to provide 17-7.

$^1$H NMR (300 MHz, $D_2O$) δ6 0.98 (9H, S) 1.45–2.05 (6H, m), 2.20–2.35 (1H, m), 2.74–2.88 (2H, t), 2.96–3.08 (2H, d), 3.10–3.34 (2H, m), 3.80–4.02 (2H, q) 5.30–5.42 (1H, m), 5.58 (2H, s), 7.68–7.78 (2H, d), 7.86–7.96 (1H, m), 8.40–8.50 (3H, m), 8.52–8.60 (1H, d), 8.66 (1H, s).

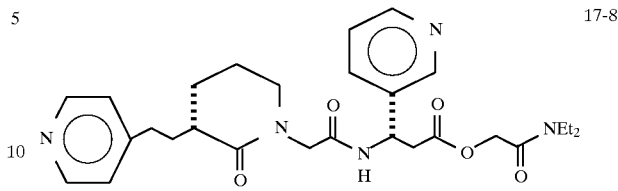

N-[3(R)-[2-(4-Pyridyl)ethyl]-2-piperidone-1-yl]acetyl-3-(S)-(3-pyridyl)-β-alanine N,N-diethyl carbamoylmethyl ester dihydrochloride (17-8)

To a solution of 17-7 dihydrochloride (0.145 g, 0.3 mmole) in dried DMF (5 ml) is added $Cs_2CO_3$ (1.95 g, 0.6 mmole). The resulting mixture is stirred at r.t. for 5 min, 2-chloro-N,N-diethylacetamide (0.090 g, 0.6 mmole) is added dropwise and the mixture is stirred overnight. The reaction was then diluted with $CH_3CN$ (50 m), the inorganics filtered and the filtrate concentrated to a viscous residue. Flash chromatography over silica gel ($CHCl_3$-MeOH 92.5=7.5) provided pure free base, $R_f$=0.52 ($CHCl_3$/MeOH, 9:1). Treatment of the free base in EtOAc with HCl/Ether provided the dihydrochloride salt 17-8.

Analysis calculated for $C_{28}H_{37}N_5O_5$+2.5 HCl+2 $H_2O$ C, 51.67; H, 6.74; N, 10.76 Found: C, 51.97; H, 6.65; N, 10.26

$^1$H NMR ($CD_3OD$) δ0.82–0.92 (3H, b), 0.92–1.06 (3H, t), 1.45–2.04 (6H, m), 2.22–2.36 (1H, m), 2.72–2.85 (2H, t), 3.00–3.42 (8H, m), 3.80–4.00 (2H, q) 4.70 (2H, s), 5.28–5.40 (1H, t), 7.68–7.84 (3H, m), 8.28–8.38 (1H, d), 8.40–8.46 (2H, d), 8.46–8.54 (1H, d), 8.80 (1H, s).

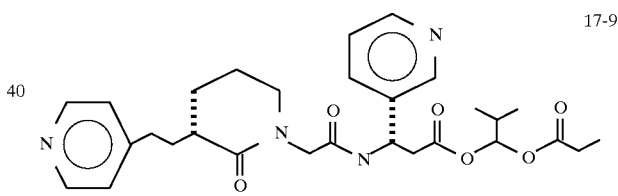

N-[3(R)-[2-(4-Pyridyl)ethyl]2-piperidone-1-yl]acetyl-3(S)-(3-pyridyl)-β-alanine dihydrochloride (17-9)

To a stirred solution of 17-6 (0.290 g, 0.6 mmole) in dried DMF(10 ml) was added $Cs_2CO_3$ (0.391 g, 1.2 mmole). The resulting mixture was stirred at r.t. for 5 min, (0.494 g, 3.0 mmole), NaI (0.090 g, 0.6 mmol) added and the mixture heated at 50° for 7 h. The reaction was diluted with $CH_3CN$ (100 ml), the inorganics filtered and the filtrate concentrated to a viscous residue. Flash chromatography over silica gel ($CHCl_3$-MeOH, 95:5) provided pure free base, $R_f$=0.24 ($CHCl_3$/MeOH, 95:5). Treatment of the free base is EtOAc with HCl/Ether at 0° C. provides the dihydrochloride salt 17-9.

Analysis calculated for $C_{29}H_{38}N_4O_6$+2.5HCl+$H_2O$ C, 53.77; H, 6.61; N, 8.65 Found: C, 54.05; H, 6.47; N, 8.39

$^1$H NMR ($CD_3OD$) δ0.86–1.00 (6H, m), 1.04–1.15 (3H, m), 1.64–2.54 (10H, m), 2.95–3.18 (4H, m) 3.30–3.55 (2H, m), 3.90–4.20 (2H, m), 5.40–5.56 (1H, m), 6.54–6.60 (1H, m), 7.94–8.1 (3H, m), 8.58–8.95 (5–6H, m).

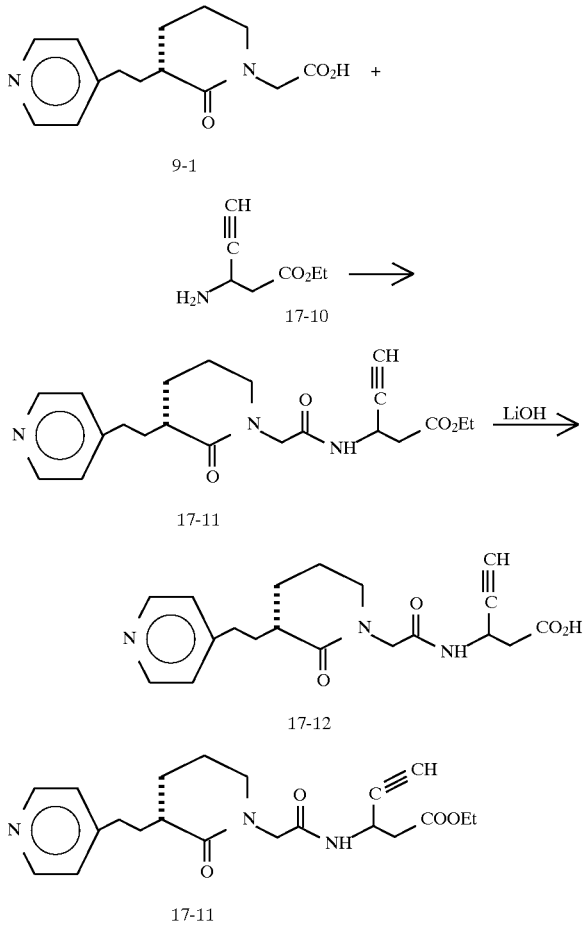

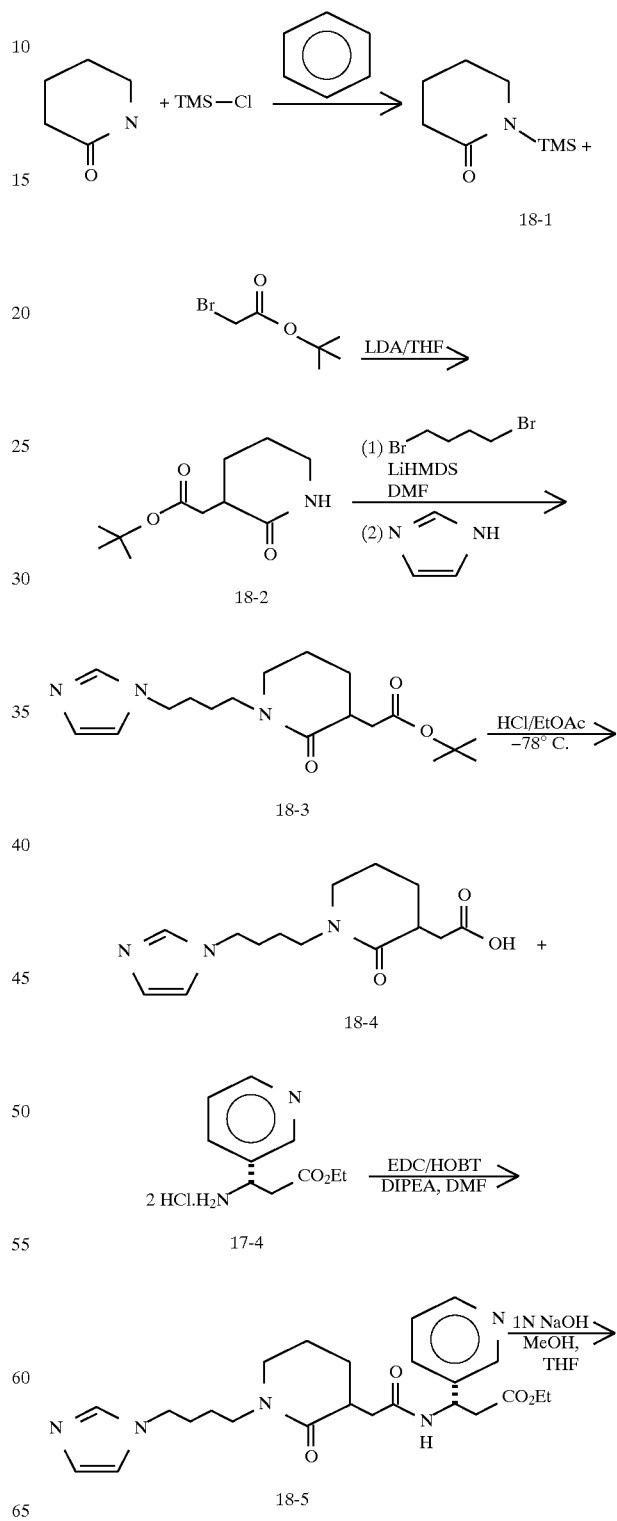

N-[3(R)-[2-(4-Pyridyl)ethyl-2-piperidone-1-yl] acetyl-3(R,S)-(3-ethynyl)-β-alanine ethyl ester (17-11)

The title compound 17-11 was prepared in a similar fashion to compound 17-2, using 9-1 and 17-10 (described in EP 542708). Flash chromatography over silical gel (CHCl₃/MeOH, 97:3) provided pure free base, $R_f$=0.35 (CHCl₃/MeOH, 95:5).

¹H NMR (CDCl₃) δ1.19–1.33 (3H, m), 1.60–2.0 (5H, m), 2.17–2.47 (3H, m), 2.60–2.82 (4H, m), 3.32–3.51 (2H, m), 3.86–4.24 (4H, m), 5.02–5.12 (1H, m), 7.08–7.24 (3H, m), 8.45–8.54 (2H, d).

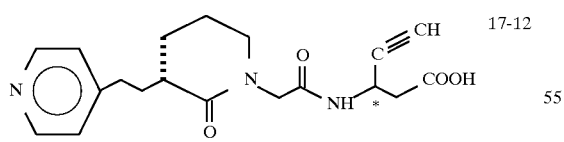

N-[3(R)-[2-(4-Pyridyl)ethyl]-2-piperidone-1-yl] acetyl-3(R,S)-(3-ethynyl)-β-alanine (17-12)

The title compound 17-12 was prepared in a similar fashion to compound 17-3. The residual material was purified by reverse phase HPLC (Delta-Pak™ C-18 column; CH₃CN/H₂O+0.1%) TFA gradient and lyophilization provided the TFA salt of the faster moving diastereomer of the title compound.

FAB MS m/z 358 (M+1).

¹H NMR (CD₃OD) δ1.68–2.30 (6H, m), 2.40–2.54 (1H, m), 2.64–2.80 (3H, m), 2.96–3.14 (2H, bt), 3.28–3.54 (2H, m), 3.88–4.18 (2H, dd), 4.95–5.06 (1H, m), 7.94–8.05 (2H, d), 8.67–8.80 (2H, d).

-continued
SCHEME 18

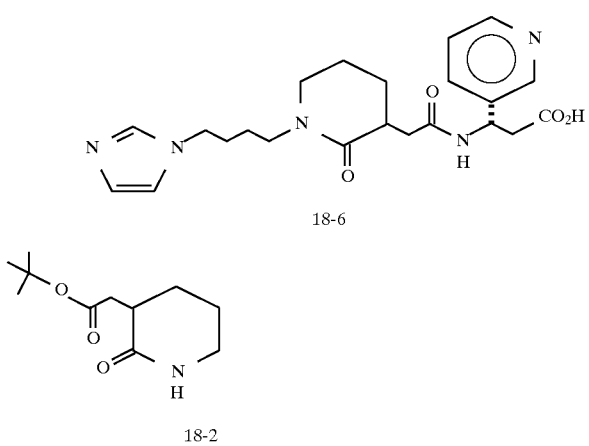

(2-Piperidone-3-yl)acetic acid tert. butyl ester (18-2)

N-Trimethylsilyl-2-pyridone (Hua et al., *J. Org. Chem.*, 1990, 55, 3682) (20 g, 0.12 mol) (18-1) dissolved in THF (400 mL) was cooled to −78° C. under argon and treated with LDA (1.5M hexane; 86 mL, 0.13 mol). After 30 minutes, the solution was warmed up to −45° C. for 30 minutes then cooled back to −78° C. at which time tert butyl bromoacetate (22.5 mL, 0.15 mol) was acidified. The mixture was warmed to room temperature and stirred for 2.5 hours before being poured into 1N HCl/EtOAc. After extraction with EtOAc (×3), the organic phase was washed with brine, dried (MgSO₄) and evaporated to give an oil.

Purification by silica gel chromatography (20% acetone in EtOAc) afforded the title compound as a pale yellow solid (9.6 g).

$R_f$=0.32 (silica gel; 15% acetone in EtOAc).

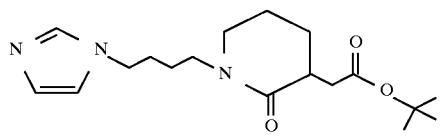

{1-[4-(1-Imidazole)butyl]-2-piperidone-3-yl}acetic acid tert butyl ester (18-3)

To a stirred solution of 18-2 (1.33 g, 6.25 mmol) in THF (30 mL) at −70° C. was added LiHMDS (1.1 eq, 1.0M=6 mL solution in THF). The mixture was warmed to −40° C. over 45 minutes, then cooled to −70° C., and 1,4-dibromobutane (2.0 eq=1.5 mL) was added. The reaction was warmed to 60° C. After 20 hours, imidazole (4.0 eq=1.7 g) was added and the mixture stirred at r.t. for 4 hours. DMF was removed in vacuo and the residue was taken up in EtOAc, washed 2× with H₂O, sat. NaHCO₃, brine, dried (MgSO₄) and concentrated to give an orange oil. Column chromatography (3% MeOH/CH₂Cl₂→5% MeOH/CH₂Cl₂) gave 300 mg 18-3 as an oil. $R_f$=0.53 (SiO₂, 10% MeOH/CH₂Cl₂).

¹H NMR (CDCl₃) δ1.43 (9H, s), 1.48–1.57 (2H, m), 1.59–1.68 (1H, m), 1.73–1.80 (2H, m), 1.82–2.01 (2H, m), 1.92–2.02 (1H, m), 2.46–2.57 (1H, m), 2.60–2.68 (1H, m), 2.70–2.79 (1H, m), 3.14–3.30 (2H, m), 3.30–3.46 (2H, m), 3.98 (2H, t), 6.93 (1H, s), 7.05 (1H, s), 7.50 (1H, s).

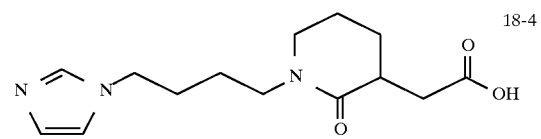

{1-[4-(1-Imidazole)butyl]-2-piperidone-3-yl}acetic acid 18-4

The t-butyl ester (200 mg, 0.62 mmol) (18-3) was converted to the acid using HCl/EtOAc at −78° C. The crude product was purified using reverse phase HPLC (Delta-Pak C-18 column, CH₃CN/H₂O with 0.1% TFA gradient). 140 mg of the title compound 18-4 was obtained as the trifluoracetate salt.

TLC $R_f$=0.45 (SiO₂, 10–0.5.0.5 EtOH.NH₄OH.H₂O)

¹H NMR (CD₃OD) δ1.55–1.70 (2H, m), 1.70–2.01 (6H, m), 2.58–2.79 (3H, m), 3.21–3.46 (3H, m), 3.54–3.67 (1H, m), 4.24–4.38 (2H, m), 7.55 (1H, s), 7.68 (1H, s), 8.92 (1H, s).

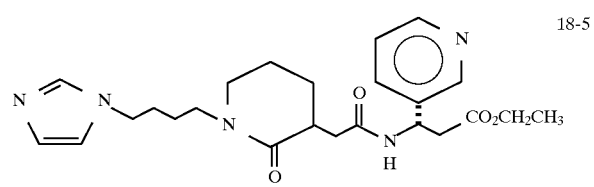

N-[1-[4-(1-Imidazole)butyl]-2-piperidone-3-yl]acetyl-3(S)-(3-pyridyl)-β-alanine ethyl ester (18-5)

The acid 17-4 (140 mg, 0.5 mmol) was coupled to 18-4 (1 eq., 115 mg) under standard EDC/HOBT conditions. Solvent was removed in vacuo. The crude product was purified by column chromatography (SiO₂, 60% EtOAc in hexane→100% EtOAc) to give the desired product 18-5 as a solid.

TLC $R_f$=0.21 (SiO₂, 60% EtOAc in hexane)

¹H NMR (CDCl₃) δ1.15 (3H, t), 1.37–1.52 (6H, m), 1.67–1.80 (2H, m), 2.59–2.75 (2H, m), 2.82–2.93 (2H, m), 3.05–3.14 (1H, m), 3.16–3.25 (1H, m), 3.29–3.34 (1H, m), 3.61–3.73 (2H, m) 3.94–4.15 (4H, m), 5.39–5.51 (1H, m), 6.93 (1H, m), 7.06 (1H, s), 7.61–7.76 (2H, m), 7.89 (1H, d), 7.98 (1H, d), 8.47 (1H, m), 8.56–8.64 (1H, dd).

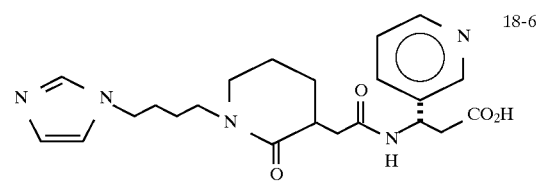

N-[1-[4-(1-Imidazol)butyl]-2-piperidone-3-yl]acetyl-3(S)-(3-pyridyl)-β-alanine (18-6)

To a stirred solution of 18-5 (120 mg, 0.26 mmol) in MeOH/THF (2 ml/3 ml) was added 1N NaOH (3.09 eq, 0.78 mL). The reaction was allowed to stir at r.t. for 4 hours. Solvent was removed in vacuo, and the crude product was purified by reverse phase HPLC (Delta-Pak™ C-18 column, CH₃CN/H₂O with 0.1% TFA gradient) to give 18-6 as the trifluoroacetate salt.

TLC $R_f$=0.48 (SiO₂, 10–0.5–0.5 EtOH.NH₂OH.H₂O)

¹H NMR (CD₃OD) δ1.37 (1H, m), 1.49–1.70 (3H, m), 1.72–1.96 (5H, m), 2.49–2.76 (4H, m), 2.90–3.30 (2H, m), 3.34–3.44 (2H, m), 4.21–4.36 (2H, m), 5.40 (1H, t), 7.52 (1H, s), 7.63 (1H, s), 7.76–7.83 (1H, m), 8.28–8.38 (1H, m), 8.61 (1H, d), 8.88 (1H, dd), 8.93 (1H, d). Å
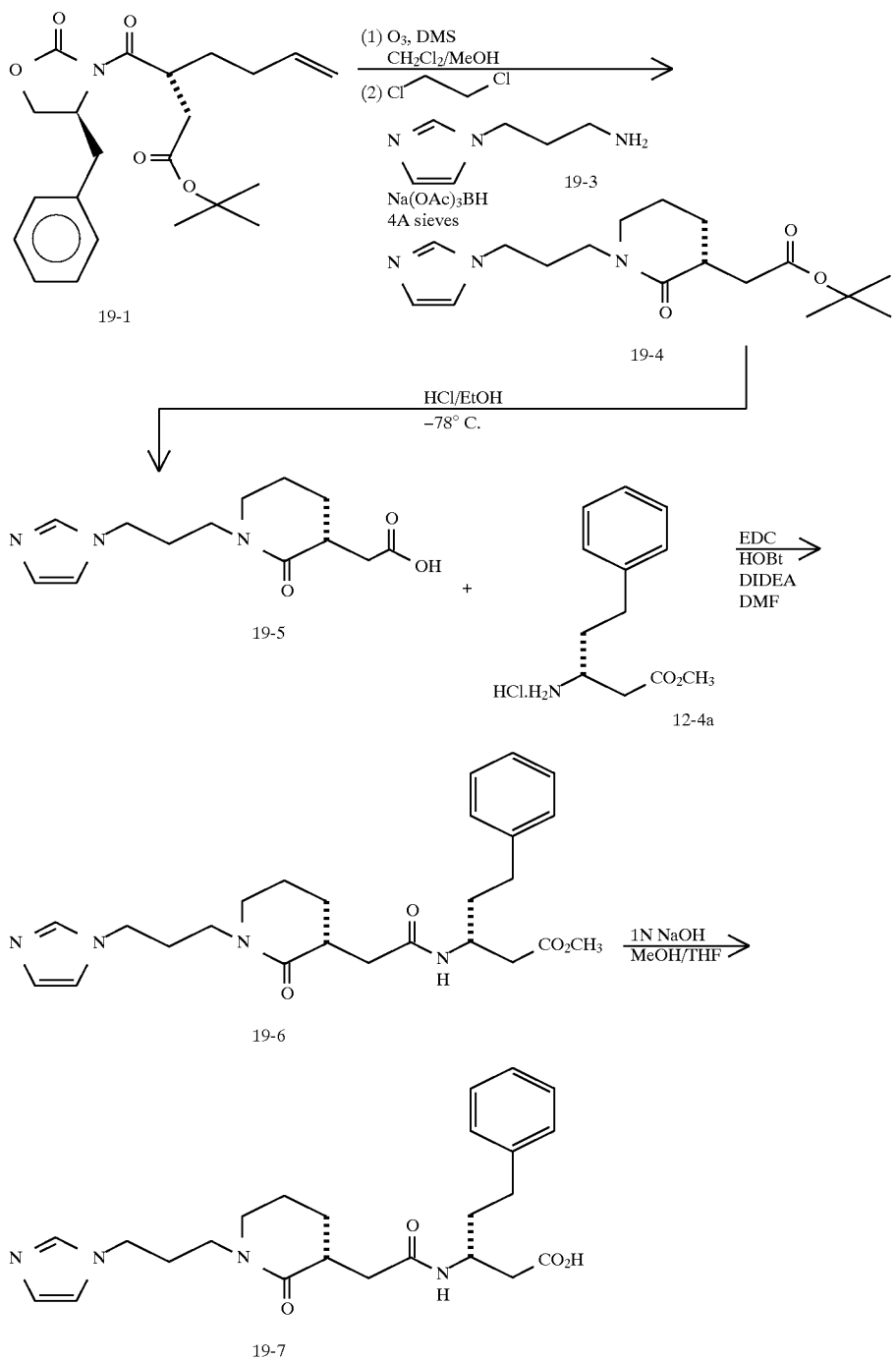
SCHEME 19

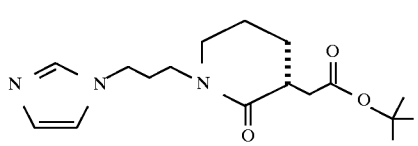

[1-(3-1-Imidazole)propyl)-2-piperidone-3(R)-yl] acetate tert-butyl ester (19-4)

Through a stirred solution of 19-1 (16 g, 41.34 mmol) in CH$_2$Cl$_2$—MeOH (200 mL, 1:1) at 78° C. was bubbled Ozone (g) until a blue color persisted. After stirring 10 min at −78° C., Argon was passed through reaction to remove excess ozone. DMS (2 eq, 0.27 mL) was added, followed by removal of the cooling bath. After 1 h at r.t., solvent was removed in vacuo; the residue taken up in EtOAc, washed with H$_2$O (5×), dried (MgSO$_4$) and concentrated in vacuo to give crude aldehyde (II), 17.2 g, as an oil.

1-(3-Aminopropyl)-imidazole (4.13 mmol, 0.49 mL) was dissolved in dichloroethane (15 mL) and adjusted to pH~6 using HOAc and Et$_3$N. 4 Å ground and dried sieves were added. The reaction mixture was cooled to 0° C. and a solution of the aldehyde (II) (1.72 g, 1.0 eq) was added dropwise. The reaction was warmed to r.t., and after 20 hours was filtered over celite. The filtrate was concentrated in vacuo, and the residue partitioned between H$_2$O and EtOAc. The organic phase was washed with saturated NaHCO$_3$, brine, dried (MgSO$_4$) and concentrated in vacuo to yield the crude product. Column Chromatography (5% MeOH on EtOAc) gave 19-4 as an oil.

TLC R$_f$=0.38 (10% MeOH in CHCl$_3$ sat. with NH$_3$)

$^1$H NMR (CDCl$_3$) δ1.42 (9H, s), 1.64–1.87 (3H, m), 1.88–1.97 (2H, m) 2.33–2.46 (1H, m), 2.52–2.63 (2H, m), 2.74–2.86 (1H, m), 3.13–3.26 (2H, m), 3.34–3.47 (1H, m), 3.68–3.81 (1H, m), 4.04–4.16 (2H, m), 7.17 (1H, s), 7.27 (1H, s), 8.31 (1H, s).

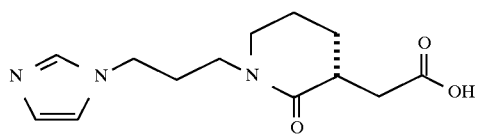

[1-(3-(1-Imidazole)propyl)-2-piperidone-3(R)-yl] acetic acid (19-5)

The t-butyl ester (I) (380 mg, 1.18 mmol) was converted to the acid using HCl/EtOAc at −78° C. The solvent was removed in vacuo to give 19-5 as a white solid.

$^1$H NMR (CD$_3$OD) δ1.71–1.89 (2H, m), 1.91–2.02 (2H, m), 2.16 (2H, m), 2.56–2.67 (2H, m), 2.77–2.88 (1H, m), 3.14–3.26 (2H, m), 3.40–3.52 (1H, m), 3.59–3.62 (1H, m), 4.27 (2H, t), 7.56 (1H, m), 7.71 (1H, m), 8.91 (1H, s).

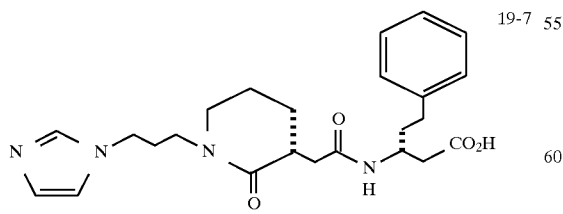

N-[1-(3-(1-Imidazole)propyl)-2-piperidone-3(R)-yl] acetyl-3(R)-(2-phenethyl)-β-alanine (19-7)

The acid (150 mg, 0.57 mmol) was coupled to 3(R)-(2-phenethyl)-β-alanine methyl ester hydrochloride (12-4a) using standard peptide procedures (EDC/HOBT). The methyl ester product 19-6 was hydrolyzed using 1N NaOH in MeOH/THF. The crude product was purified using reverse phase HPLC [Delta-Pak™ C-18 column, CH$_3$CN/ H$_2$O with 0.1% TFA gradient). The title compound 19-7 was collected as the trifluoroacetate salt.

TLC R$_f$=0.63 (silica, 10:0.5:0.5 EtOH–NH$_4$OH–H$_2$O)

$^1$H NMR (CD$_3$OD) δ1.67–1.86 (6H, m), 1.86–1.99 (2H, m) 2.08–2.21 (2H, m), 2.51–2.71 (5H, m), 2.74–2.85 (1H, m), 3.09–3.20 (1H, m), 3.40–3.52 (1H, m), 3.66–3.80 (1H, m), 4.14–4.30 (1H, m), 4.30 (2H, t), 7.05–7.26 (5H, m), 7.50 (1H, s), 7.68 (1H, s), 8.93 (1H, s).

SCHEME 20

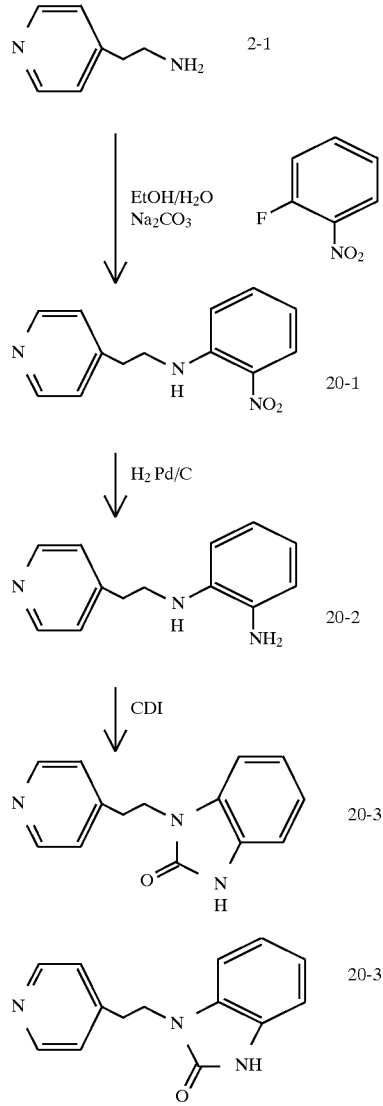

SCHEME 20 -continued

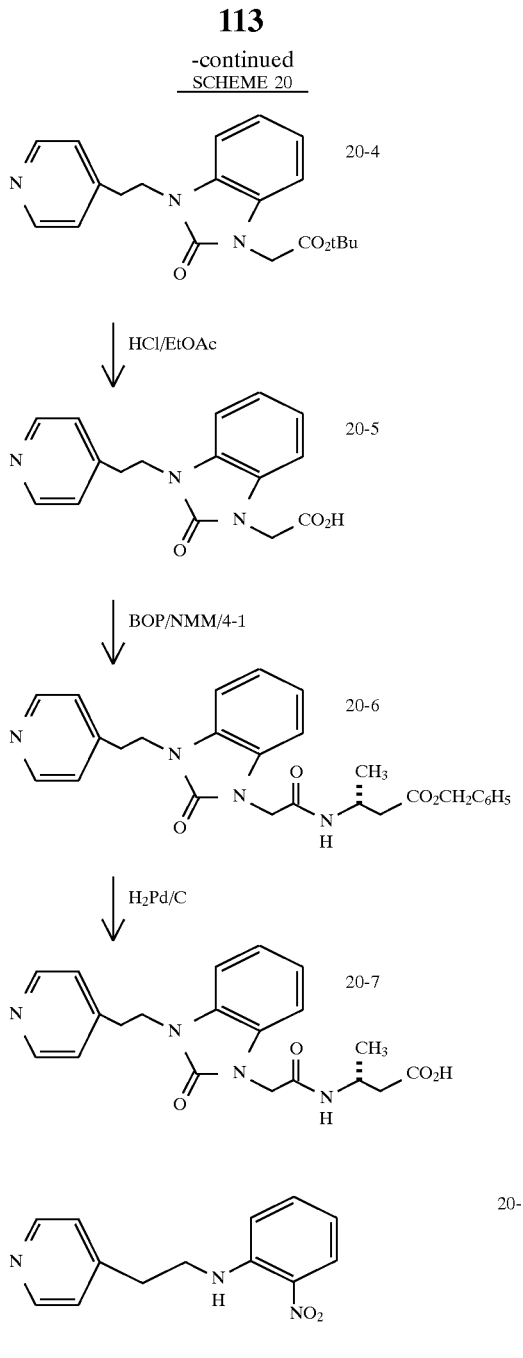

2-[2-(4-Pyridyl)ethyl]amino-nitrobenzene (20-1)

A solution of 2-1 (6 g, 49.1 mmol) and o-fluoronitrobenzene (Aldrich, 5.2 mL, 49.1 mmol) in 59 mL of water was treated with $Na_2CO_3$ (15.6 g, 0.147 mol), diluted with 160 mL 1:1 $EtOH/H_2O$ and heated to 60° C. for 18 h. The homogenous solution was diluted with 10% $KHSO_4$ until the solution was pH 2–3, ether was added and the layers were separated. The aqueous layer was washed twice more with ether, then basified with NaOH to pH 10 and extracted with $CHCl_3$. The $CHCl_3$ layers were combined, washed with brine and evaporated to give 20-1 as a brown solid.

$R_f$ (5% $MeOH/CHCl_3$ saturated with $NH_3$) 0.75

$^1H$ NMR (400 MHz, $CDCl_3$) δ8.56 (2s, 2H), 8.18 (d, 1H), 8.05 (bs, 1H), 7.45 (t, 1H), 7.2 (2s, 2H), 6.85 (d, 1H), 6.78 (t, 1H), 3.6 (m, 2H), 3.02 (m, 2H).

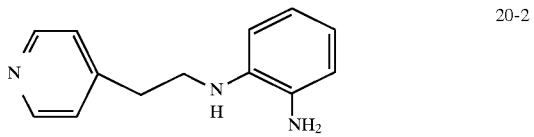

2-[2(4-Pyridyl)ethyl]aminoaniline (20-2)

A solution of 20-1 (5.56 g, 22.8 mmol) in methanol (200 mL) was treated with 10% Pd/C (1.6 g) and hydrogen gas at balloon pressure for 3.5 h, at which time the solution, which had originally been yellow, was colorless. The reaction was filtered through Solka Floc, the cake washed with methanol and the filtrate evaporated to give 20-2 as an air-sensitive, pale brown oil.

$R_f$ (5% $MeOH/CHCl_3$ saturated with $NH_3$) 0.65.

$^1H$ NMR (400 MHz, $CDCl_3$) δ8.52 (2s, 2H), 7.16 (2s, 2H), 6.83 (m, 1H), 6.7 (m, 3H), 3.42 (t, 2H), 2.95 (t, 2H).

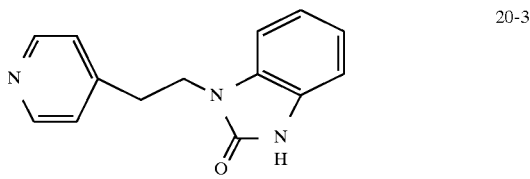

N-[2-(4-Pyridyl)ethyl]benzimidazolone (20-3)

A solution of 20-2 (4.61 g, 21.6 mmol) in THF (115 mL) under argon was treated with carbonyldiimidazole (17.6 g, 108.6 mmol) and heated to 60° C. for 3 h. The reaction was cooled to room temperature and stirred for 18 h, diluted with 100 mL water, stirred for 30 minutes, concentrated under vacuum and the residue was absorbed to silica gel and chromatographed (75% acetone/hexanes to 100% acetone gradient) to give 20-3 as a mixture with imidazole. The crude product was re-chromatographed in 10% isopropranol/$CH_2Cl_2$ to give pure 20-3 as a yellow, oily solid.

$R_f$ (5% $MeOH/CHCl_3$ saturated with $NH_3$) 0.34.

$^1H$ NMR (400 MHz, $CD_3OD$) δ8.33 (2s, 2H), 7.24 (2s, 2H), 7.0 (m, 4H), 4.15 (t, 2H), 3.08 (t, 2H).

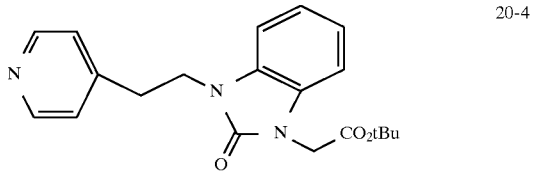

N-[2-(4-Pyridyl)ethyl]-N'-(2-t-butyl acetyl)-benzimidazolone (20-4)

A solution of 20-3 (3.55 g, 14.8 mmol) in DMF (50 mL) was treated dropwise with $NaN(TMS)_2$ (16.3 mL, 1.0M in THF), the solution was stirred for 45 minutes, then treated with t-butyl bromoacetate (2.7 mL, 17 mmol) and stirred for 30 minutes. The reaction was quenched with $H_2O$ and the solvents were removed in vacuo. The residue was chromatographed (silica gel, 50% acetone/Hexanes) to give 20-4 as a oily, yellow solid.

$R_f$ (60% Acetone/Hexanes) 0.43.

$^1H$ NMR (400 MHz, $CDCl_3$) δ8.46 (m, 2H), 7.14 (m, 2H), 7.05 (m, 2H), 6.85 (m, 2H), 4.5 (s, 2H), 4.14 (t, 2H), 3.05

(t, 2H), 1.45 (s, 9H).

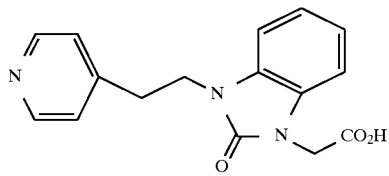

20-5

N-[2-(4-Pyridyl)ethyl]-N'-(2-acetyl)-benzimidazolone (20-5)

A suspension of 20-4 (4.5 g, 12.7 mmol) in EtOAc (30 mL) was cooled to −78° C. and saturated with HCl gas. The resulting homogenous solution was warmed to 0° C. for 2 h, then to room temperature for 2 h. A white precipitate formed. The reaction was concentrated to give 20-5 as a white solid.

$^1$H NMR (400 MHz, D$_2$O) δ8.4 (2s, 2H), 7.63 (2s, 2H), 7.1–7.0 (m, 4H), 4.48 (s, 2H), 4.18 (t, 2H), 3.28 (t, 2H).

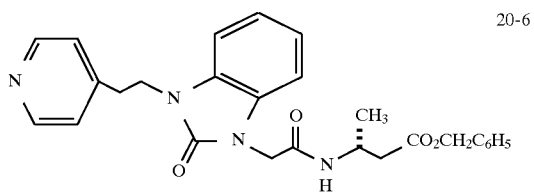

20-6

[N'-[N-[2-(Pyridine-4-yl)ethylbenzimidazolone]acetamido]-3-(3(R)-methyl)propanoic acid benzyl ester (20-6)

A solution of 20-5 (0.75 g, 2.2 mmol) and 4-1 (0.6 g, 2.5 mmol) in acetonitrile (15 mL) was treated with BOP reagent (1.79 g, 4.0 mmol) and NMM (1.5 mL, 14 mmol) and stirred for 18 h. The reaction was concentrated and the residue was dissolved in EtOAc, washed with NaHCO$_3$, dried over Na$_2$SO$_4$, filtered and evaporated. The residue was chromatographed (silic gel, 75% Acetone/Hexanes to 100% acetone gradient) to give 20-6 as a clear oil.

R$_f$ (70% Acetone/Hexanes) 0.37.

$^1$H NMR (400 MHz, CDCl$_3$) δ8.46 (2s, 2H), 7.3 (m, 4H), 7.13 (2s, 2H), 7.06 (m, 2H), 6.96 (m, 1H), 6.86 (m, 1H), 6.7 (d, 1H), 4.98 (s, 2H), 4.43 (ABq, 2H), 4.4–4.3 (m, 1H), 4.11 (t, 2H), 3.04 (t, 2H), 2.5 (m, 2H), 1.15 (d, 3H).

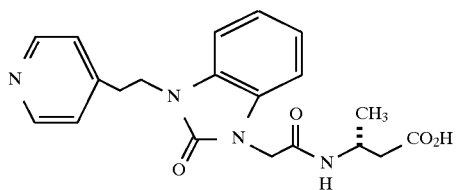

20-7

[N'-[N-[2-(Pyridine-4-yl)ethy]benzimidazolone]acetamido]-3-(3(R)-methyl)propanoic acid (20-7)

A solution of 20-6 (0.4 g, 0.85 mmol) in CH$_3$OH (5 mL) was treated with 10% Pd/C (0.1 g) and placed under a hydrogen-filled balloon. After 2 h the reaction was filtered through a Solka-Floc and the cake rinsed with 9:1:1 EtOH/H$_2$O/NH$_4$OH. The filtrate was concentrated and residue was chromatographed 49:1:1 EtOH/H$_2$O/NH$_4$OH to give 20-7 as a white solid.

R$_f$ (49:1:1 EtOH/H$_2$O/NH$_4$OH)0.29.

$^1$H NMR (400 MHz, D$_2$O+NaOD) δ8.12 (2s, 2H), 7.0 (m, 4H), 6.92 (d, 1H), 6.87 (d, 1H), 4.39 (s, 2H), 4.05 (m, 3H), 2.95 (t, 2H), 2.31 (dd, 1H), 2.18 (dd, 1H), 1.05 (d, 3H).

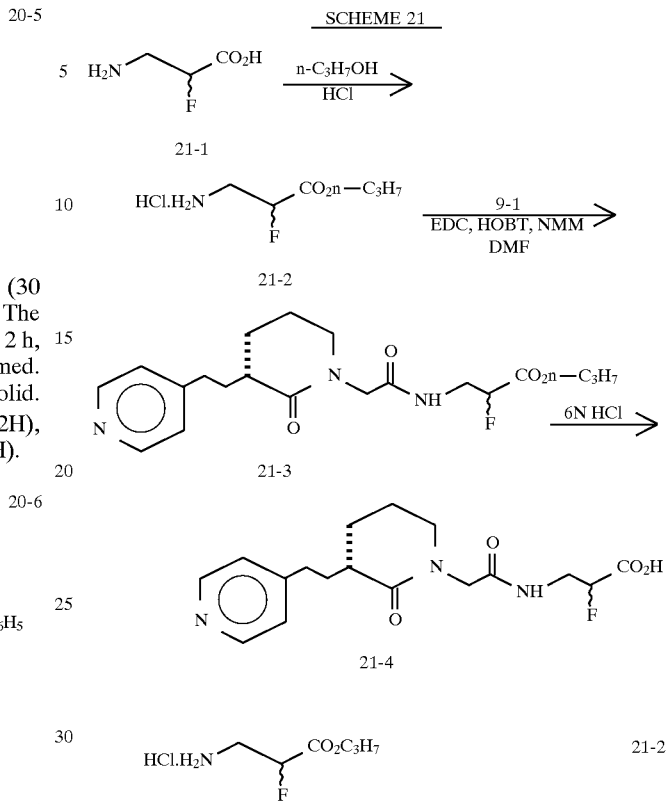

(D,L)-n-Propyl alpha-fluoro-beta-alanine (21-2)

A suspension of 21-1 (American Tokyo Kasei, 0.5 g, 3.5 mmol) in n-propanol (10 mL was cooled to 0° C. and saturated with HCl gas. The reaction was stirred for 18 h, then re-cooled to 0° C. and resaturated with HCl gas and stirred for a further 18 h. The reaction was concentrated to give 21-2 as a white solid.

R$_f$ (9:1:1 EtOH/H$_2$O/NH$_4$OH) 0.51.

$^1$H NMR (400 MHz, CD$_3$OD) δ5.38 (dd, 0.5H), 5.25 (dd, 0.5H), 4.2 (m, 2H), 3.6–3.4 (m, 2H), 1.7 (m, 2H), 0.98 (5, 3H).

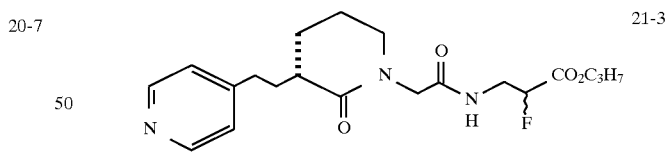

21-3

[[3(R)-(2-(Pyridin-4-yl)ethyl)-2-piperidon-1-yl]acetamido]-3-(2(R,S)-fluoro)propanoic acid propyl ester (21-3)

A solution of 9-1 (2.52 g, 3.9 mmol) and ((D,L)-Propyl alpha-fluoro-beta-alanine) (0.602 g, 3.24 mmol) in DMF (15 mL) was treated with HOBT (0.49 g, 3.6 mmol), EDC (0.73 g, 3.8 mmol) and NMM (2.3 mL, 21 mmol) and stirred at room temperature for 18 h. The solvent was removed in vacuo and the residue was chromatographed (silica gel, 100% acetone), treated with trifluoracetic acid and lyophilized to give 21-3 as a white solid.

R$_f$ (100% acetone)0.5.

$^1$H NMR (400 MHz, CD$_3$OD) δ8.6 (2s, 2H), 7.88 (2s, 2H), 5.02 (m, 0.5H), 4.9 (m, 0.5H), 4.03 (m, 2H), 3.9 (m,

2H), 3.6 (m, 2H), 3.45–3.2 (m, 2H), 2.93 (m, 2H), 2.45 (m, 1H), 2.1 (m, 1H), 2.0–1.7 (m, 4H), 1.6 (m, 3H), 0.85 (t, 3H).

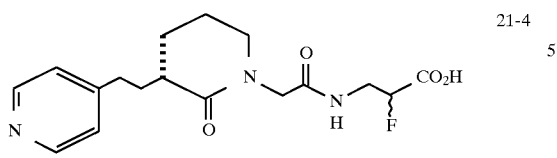

21-4

[[3(R)-(2-(Pyridin-4-yl)ethyl)-2-piperidon-1-yl] acetamido]-3-(2(R,S)-fluoro)propanoic acid (21-4)

A solution of 21-3 (0.45 g, 1.1 mmol) in dioxane (2 mL), was treated with 6N HCl (20 mL) and stirred for 18 h. The solution was concentrated and the residue chromatographed (9:1:1 EtOH/H$_2$O/NH$_4$OH, followed by 98:1:1 EtOH/H$_2$O/NH$_4$OH) to give 21-4 as a white solid.

$R_f$ (9:1:1 EtOH/H$_2$OH)0.57

$^1$H NMR (400 MHz, D$_2$O ) δ8.3 (2s, 2H), 7.8 (2s, 2H), 4.8 (dd, 0.5H), 4.68 (dd, 0.5H), 3.9 (m, 1H), 3.8 (d, 1H), 3.6 (d, 1H), 3.6–3.4 (m, 1H), 3.4–3.3 (m, 2H), 2.67 (m, 2H), 1.8 (m, 1H), 2.0 (m, 1H), 1.9–1.5 (m, 6H).

EXAMPLE 22

Tablet Preparation

Tablets containing 25.0, 50.0, and 100.0 mg., respectively, of the active compound (3(R)-[(2-Amino-4-pyridyl)ethyl]-2-piperidon-1-yl)acetic-β-alanine are prepared as illustrated below:

| TABLE FOR DOSES CONTAINING FROM 25–100 MG OF THE ACTIVE COMPOUND | | | |
|---|---|---|---|
| | Amount-mg | | |
| Active Compound | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 23

Intravenous formulations

An intravenous dosage form of the above-indicated active compound is prepared as follows:

| | |
|---|---|
| Active Compound | 0.5–10.0 mg |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

EXAMPLE 24

Intravenous formulation

A pharmaceutical composition was prepared at room temperature using (3(R)-[(2-Amino-4-pyridyl)ethyl]-2-piperidon-1-yl)acetic-β-alanine, a citrate buffer, and sodium chloride, to obtain a concentration of of 0.25 mg/ml.

800 grams of water was introduced into a standard pharmaceutical mixing vessel. 0.25 grams of (3(R)-[(2-Amino-4-pyridyl)ethyl]-2-piperidon-1-yl)acetic-β-alanine was dissolved in the water. 2.7 grams sodium citrate and 0.16 grams citric acid were added to obtain a finished citrate concentration of 10 mM. 8 grams of sodium chloride was added. 200 grams of water was then added to achieve the desired final concentrations of ingredients. The resulting aqueous formulation had the following concentrations:

| Ingredient | Amount |
|---|---|
| (3(R)-[(2-Amino-4-pyridyl)ethyl]-2-piperidon-1-yl)acetic-β-alanine | 0.25 mg/ml |
| citrate buffer | 10 mM |
| sodium chloride | 8 mg/ml |

The finished concentrated formulation is stored in a standard USP Type I borosilicate glass container at 30–40 degrees C. Prior to compound administration, the concentrated formulation is diluted in a 4:1 ratio resulting in a finished concentration of 0.05 mg/ml and transferred to an infusion bag.

Therapeutic Treatment

Compounds of the invention may be administered to patients where inhibition of human or mammalian platelet aggregation or adhesion is desired.

Compounds of the invention are useful in inhibiting platelet aggregation and thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

What is claimed is:

1. A compound having the formula

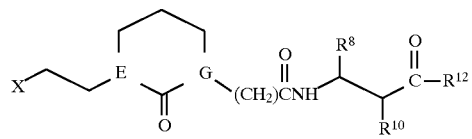

or a pharmaceutically acceptable salt thereof, wherein
X is
an aromatic heterocyclic ring selected from the group consisting of:

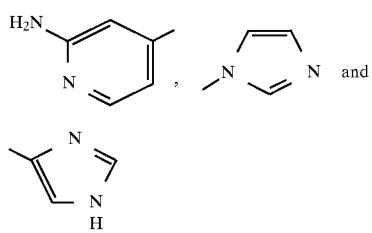

E is —CH— or —N—;
G is —CH— or —N—;
R⁸ is
  hydrogen,
  $C_{1-8}$ alkyl,
  aryl,
  aryl $C_{1-6}$ alkyl,
  hydroxy $C_{1-6}$ alkyl,
  $C_{1-6}$ alkylsulfonyl,
  $C_{1-6}$ alkylsulfonyl $C_{1-6}$ alkyl,
  aryl sulfonyl $C_{1-6}$ alkyl,
  aryl sulfonyl,
  aryl $C_{1-6}$ alkylsulfonyl, or
  aryl $C_{1-6}$ alkylsulfonyl $C_{1-6}$ alkyl;
$R^{10}$ is
  hydrogen
  —NHCOR²,
  —NH₂,
  —NH₂SO₂R², or
  —OH;
$R^{12}$ is
  —OR²,
  —OCH₂OCOR², or
  —OCH₂OCON(R²)₂; and
R² is
  hydrogen,
  halogen,
  $C_{1-10}$ alkyl,
  $C_{3-8}$ cycloalkyl,
  aryl,
  aryl $C_{1-8}$ alkyl,
  amino,
  amino $C_{1-8}$ alkyl,
  $C_{1-3}$ acylamino,
  $C_{1-3}$ acylamino $C_{1-8}$ alkyl,
  $C_{1-6}$ alkylamino,
  $C_{1-6}$ alkylamino $C_{1-8}$ alkyl,
  $C_{1-6}$ dialkylamino,
  $C_{1-6}$ dialkylamino $C_{1-8}$ alkyl,
  $C_{1-4}$ alkoxy,
  $C_{1-4}$ alkoxy $C_{1-6}$ alkyl,
  carboxy,
  carboxy $_{1-6}$ alkyl,
  $C_{1-3}$ alkoxycarbonyl,
  $C_{1-3}$ alkoxycarbonyl $C_{1-6}$ alkyl,
  carboxy $C_{1-6}$ alkyloxy,
  hydroxy, and
  hydroxy $C_{1-6}$ alkyl.

2. A compound of claim 1 having the formula:

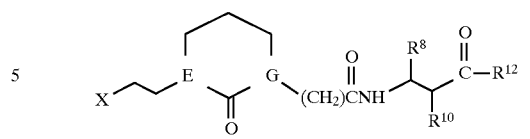

and pharmaceutically acceptable salts thereof, wherein
$R^8$ is

—hydrogen,
  —CH₃,
  —C≡CH,
  —C₆H₅,

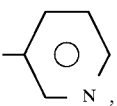

—CH₂CH₂—C₆H₅,
  —CH₂—C₆H₅,

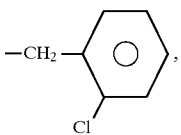

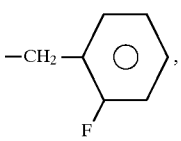

—CH₂OH,

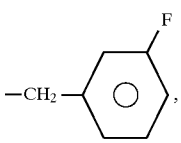

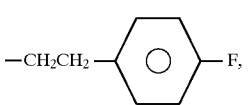

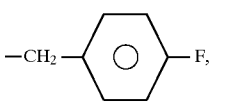

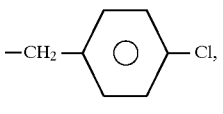

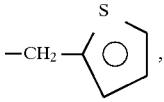

—CH₂—CH(CH₃)₂,
  —CH₂CH₂CH₃,
  —CH₂SO₂—C₆H₅,

-continued

—C≡C—C₆H₅,

—C≡CCH₃,

—C≡C—C(CH₃)₃,

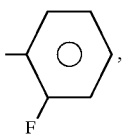

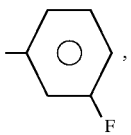

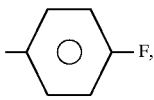

—C≡CC₃H₅;

and
R² is
-hydrogen
—CH₂C₆H₅,
—CH₂C(O)N(CH₂CH₃)₂,
—CH₂C(O)N(CH₃)C₆H₁₃,
—CH₂CH₃,
—C(CH₃)₃,
—CH(CH₃)₂OC(O)CH₂CH₃,

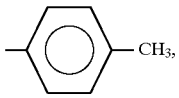

or
—CH₂CH₂CH₃.

3. A composition for inhibiting the binding of fibrinogen to blood platelets in a mammal, comprising an antifibrinogenic binding effective amount of a compound of claim 1 and a pharmaceutically acceptable carrier.

4. A composition for inhibiting the aggregation of blood platelets in a mammal, by blocking fibrinogen from acting at its receptor site, comprising an antifibrinogenic binding effective amount of a compound of claim 1 and a pharmaceutically acceptable carrier.

5. A method for inhibiting the binding of fibrinogen to blood platelets in a mammal, comprising treating the mammal in need thereof with a composition of claim 3.

6. A method for inhibiting the aggregation of blood platelets in a mammal, by blocking fibrinogen from acting at its receptor site, comprising treating the mammal in need thereof a composition of claim 4.

7. A composition for inhibiting the binding of fibrinogen to blood platelets, in a mammal, comprising an antifibrinogenic binding effective amount of a compound of claim 2 and a pharmaceutically acceptable carrier.

8. A composition for inhibiting the aggregation of blood platelets, in a mammal, by blocking fibrinogen from acting at its receptor site, comprising an antifibrinogenic binding effective amount of a compound of claim 2 and a pharmaceutically acceptable carrier.

9. A method for inhibiting the binding of fibrinogen to blood platelets in a mammal, by blocking fibrinogen from acting at its receptor site, comprising treating the mammal in need thereof a composition of claim 7.

10. A method for inhibiting the aggregation of blood platelets in a mammal, by blocking fibrinogen from acting at its receptor site, comprising treating the mammal in need thereof a composition of claim 8.

11. A compound of claim 2 selected from the group consisting of:
[3(R)-[1-(2-(2-Aminopyridin-4-yl)ethyl)-2-piperidon-3-yl] acetamido]-3-(3-(S)-(pyridin-3-yl))propanoic acid ethyl ester,
[3(R)-[1-(2-(2-Aminopyridin-4-yl)ethyl)-2-piperidon-3-yl] acetamido]-3-(3(S)-pyridin-3-yl))propanoic acid,
(3(R)-[(2-Amino-4-pyridyl)ethyl]-2-piperidon-1-yl)acetyl-β-alanine-tert-butyl ester,
(3(R)-[(2-Amino-4-pyridyl)ethyl]-2-piperidon-1-yl)acetic-β-alanine,
(3(R)-[(2-Amino-4-pyridyl)ethyl]-2-piperidon-1-yl)acetyl-3 (R)-methyl-β-alanine benzyl ester,
(3(R)-[(2-Amino-4-pyridyl)ethyl]-2-piperidon-1-yl)acetyl-3 (R)-methyl-β-alanine,
or a pharmaceutically acceptable salt thereof.

12. A compound having the formula

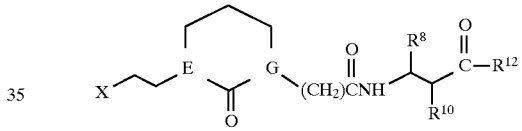

or a pharmaceutically acceptable salt thereof, wherein
X is
an aromatic heterocyclic ring selected from the group consisting of:

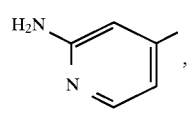

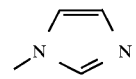

and

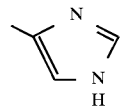

E is —CH— or —N—;
G is —CH— or —N—;
R⁸ is

—CH—C₆H₅,
|
OH

-continued

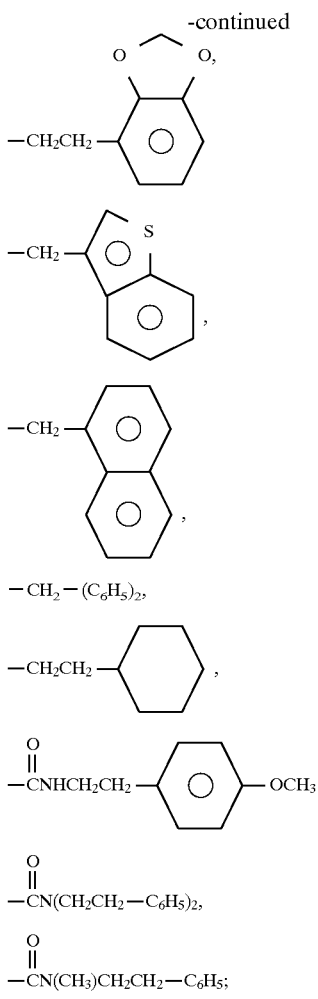

$R^{10}$ is
hydrogen,
—NHCOR$^2$,
—NH$_2$,
—NH$_2$SO$_2$R$^2$, or
—OH;

$R^{12}$ is
—OR$_2$,
—OCH$_2$OCOR$^2$, or
—OCH$_2$OCON(R$^2$)$_2$; and $R^2$ is
hydrogen,
halogen,
C$_{1-10}$ alkyl,
C$_{3-8}$ cycloalkyl,
aryl,
aryl C$_{1-8}$ alkyl,
amino,
amino C$_{1-8}$ alkyl,
C$_{1-3}$ acylamino,
C$_{1-3}$ acylamino C$_{1-8}$ alkyl,
C$_{1-6}$ alkylamino,
C$_{1-6}$ alkylamino C$_{1-8}$ alkyl,
C$_{1-6}$ dialkylamino,
C$_{1-6}$ dialkylamino C$_{1-8}$ alkyl,
C$_{1-4}$ alkoxy,
C$_{1-4}$ alkoxy C$_{1-6}$ alkyl,
carboxy,
carboxy $_{1-6}$ alkyl,
C$_{1-3}$ alkoxycarbonyl,
C$_{1-3}$ alkoxycarbonyl C$_{1-6}$ alkyl,
carboxy C$_{1-6}$ alkyloxy,
hydroxy, and
hydroxy C$_{1-6}$ alkyl.

13. A compound selected from the group consisting of
N-[1-[4-(1-Imidazole)butyl]-2-piperidone-3-yl]acetyl-3(S)-(3-pyridyl)-β-alanine ethyl ester,
N-[1-[4-(1-imidazol)butyl]-2-piperidone-3-yl]acetyl-3(S)-(3-pyridyl)-β-alanine, and
N-[1-(3-(1-Imidazole)propyl)-2-piperidone-3(R)-yl]acetyl-3(R)-(2-phenethyl)-β-alanine
or a pharmaceutically acceptable salt thereof.

* * * * *